(12) United States Patent
Novak et al.

(10) Patent No.: US 12,319,680 B2
(45) Date of Patent: Jun. 3, 2025

(54) COMPOUNDS

(71) Applicant: Step Pharma S.A.S., Paris (FR)

(72) Inventors: Andrew Novak, Nottingham (GB); Joseph Wrigglesworth, Nottingham (GB)

(73) Assignee: Step Pharma S.A.S., Paris (FR)

( * ) Notice: Subject to any disclaimer, the term of this patent is extended or adjusted under 35 U.S.C. 154(b) by 0 days.

(21) Appl. No.: 17/962,938

(22) Filed: Oct. 10, 2022

(65) Prior Publication Data

US 2023/0183229 A1 Jun. 15, 2023

Related U.S. Application Data

(63) Continuation of application No. 16/767,379, filed as application No. PCT/EP2018/083140 on Nov. 30, 2018, now Pat. No. 11,505,547.

(30) Foreign Application Priority Data

| Nov. 30, 2017 | (EP) | 17204796 |
| Mar. 23, 2018 | (EP) | 18163766 |
| Jun. 4, 2018 | (EP) | 18175823 |

(51) Int. Cl.
| C07D 417/12 | (2006.01) |
| C07D 277/52 | (2006.01) |
| C07D 417/14 | (2006.01) |

(52) U.S. Cl.
CPC ......... *C07D 417/12* (2013.01); *C07D 277/52* (2013.01); *C07D 417/14* (2013.01)

(58) Field of Classification Search
CPC ... C07D 417/12; C07D 277/52; C07D 417/14
See application file for complete search history.

(56) References Cited

U.S. PATENT DOCUMENTS

| 6,048,884 | A | 4/2000 | Maruyama et al. |
| 9,181,235 | B2 * | 11/2015 | Cheng .................. C07D 403/12 |
| 2003/0176476 | A1 | 9/2003 | Barf et al. |
| 2008/0139557 | A1 | 6/2008 | Blomgren et al. |
| 2016/0152583 | A1 | 6/2016 | Arisawa et al. |
| 2021/0002269 | A1 | 1/2021 | Quddus et al. |
| 2021/0024507 | A1 | 1/2021 | Quddus et al. |
| 2021/0387965 | A1 | 12/2021 | Quddus et al. |

FOREIGN PATENT DOCUMENTS

| CN | 104262071 A | 1/2015 |
| EP | 1659113 A1 | 5/2006 |
| EP | 2292603 A1 | 3/2011 |
| GB | 1555007 | 11/1979 |
| GB | 1555007 A | 11/1979 |
| GB | 1575803 | 10/1980 |
| WO | WO 2006/010751 A1 | 2/2006 |
| WO | WO 2009/075874 A1 | 6/2009 |
| WO | WO 2012/082817 A1 | 6/2012 |
| WO | WO 2014/090715 A1 | 6/2014 |
| WO | WO 2014/170435 A2 | 10/2014 |
| WO | WO 2016/055786 A1 | 4/2016 |
| WO | WO 2019/106146 A1 | 6/2019 |
| WO | WO 2019/106156 A1 | 6/2019 |
| WO | WO 2019/179652 A1 | 9/2019 |
| WO | WO 2019/180244 A1 | 9/2019 |
| WO | WO 2020/083975 A1 | 4/2020 |
| WO | WO 2020/053402 A2 | 12/2020 |
| WO | WO 2020/245664 A1 | 12/2020 |
| WO | WO 2020/245665 A1 | 12/2020 |
| WO | WO 2021/053403 A1 | 3/2021 |
| WO | WO 2022/087634 A1 | 4/2022 |
| WO | WO 2023/205475 A1 | 10/2023 |

OTHER PUBLICATIONS

Klapars et al., "Copper-Catalyzed Halogen Exchange in Aryl Halides: An Aromatic Finkelstein Reaction," Journal of the American Chemical Society, American Chemical Society, 124: 14844-14845 (2002).
Ananthakrishnanadar et al., "The Effects of Substituents on the Rate of Saponification of Biphenyl-4-carboxylates," Journal of the Chemical Society, Perkin Transactions 2: Physical Organic Chemistry, 11 (1): 35-37 (1984).
Database Registry, Chemical Abstracts Service, XP055772827, Feb. 20, 2014.
Database Registry, Chemical Abstracts Service, XP055772837, Jun. 10, 2009.
Database Registry, Chemical Abstracts Service, XP055772841, Dec. 4, 2017.
Database Registry, Chemical Abstracts Service, XP055772832, Jun. 10, 2009.
Database Registry, Chemical Abstracts Service, XP055772844, Nov. 10, 2011.
Database Registry, Chemical Abstracts Service, XP002801975, Mar. 8, 2019.
Database Registry, Chemical Abstracts Service, XP002801976, Dec. 10, 2013.
Database Registry, Chemical Abstracts Service, XP002801977, Nov. 1, 2013.
Database Registry, Chemical Abstracts Service, XP002801978, Nov. 4, 2013.
Database Registry, Chemical Abstracts Service, XP002801979, Dec. 2, 2013.
Database Registry, Chemical Abstracts Service, XP002801980, Dec. 8, 2013.

(Continued)

*Primary Examiner* — Bruck Kifle
(74) *Attorney, Agent, or Firm* — Morgan, Lewis & Bockius LLP

(57) ABSTRACT

Compounds of formula (I) and related aspects.

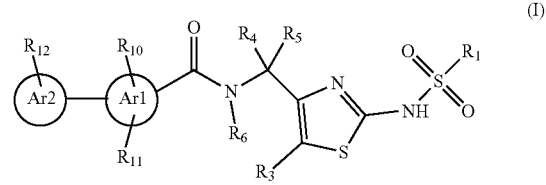

1 Claim, No Drawings

(56) References Cited

OTHER PUBLICATIONS

Database Registry, Chemical Abstracts Service, XP002801981, Dec. 13, 2013.
Database Registry, Chemical Abstracts Service, XP002801982, Dec. 15, 2013.
Database Registry, Chemical Abstracts Service, XP002801983, Dec. 19, 2013.
Lee et al., "Identification of novel small molecule inhibitors against NS2B/NS3 serine protease from Zika virus," Antiviral Research, 139: 49-58 (2016).
Lubbers et al., "Aminothiazoles as y-secretase modulators," Bioorganic & Medicinal Chemistry Letters, 21: 6554-6558 (2011).
Tang et al., "CTP synthase 1, a smooth muscle-sensitive therapeutic target for effective vascular repair," Atherosclerosis, Thrombosis and Vascular Biology, 33: 2336-2344 (2013).
National Centre for Biotechnology Information, PubChem Substance record for SID69002076, ZINC29974483, May 29, 2009.
Lynch, et al., "Structural basis for isoform-specific inhibition of human CTPS1," PNAS, vol. 118, No. 40, 9 pages, 2021.
International Search Report & Written Opinion PCT Application No. PCT/EP2018/083140, dated Jun. 6, 2019, 12 pages.
International Search Report & Written Opinion PCT Application No. PCT/EP2018/083169, dated Jun. 6, 2019, 12 pages.
Klapers, et al., "Copper-Catalyzed Halogen Exchange in Aryl Halides: An Aromatic Finkelstein Reaction," J. Am. Chem. Soc., vol. 124, pp. 14844-14845, 2002.
Lai, et al., "A biocompatible inverse electron demand Diels-Alder reaction of aldehyde and tetrazine promoted by proline," New J. Chem. vol. 40, pp. 8194-8197, 2016.
McCluskey, et al., "Exploring the Potent Inhibition of CTP Synthase by Gemcitabine-5'-Triphosphate," ChemBioChem., vol. 17, pp. 2240-2249, 2016.
Meng, et al., "Carboxylation of Aromatic and Aliphatic Bromides and Triflates with $CO_2$ by Dual Visible-Light-Nickel Catalysis," Angew. Chem. Int. Ed., vol. 56, pp. 13426-13430, 2017.
Sakamoto, et al., "Identification of cytidine-5-triphosphate synthase1-selective inhibitory peptide from random peptide library displayed on T7 phage," Peptides, vol. 94, pp. 56-63, 2017.
Thirumoorthi, et al., "A practical metal-free homolytic aromatic alkylation protocol for the synthesis of 3-(pyrazine-2-yl)bicycle[1.1.1]pentane-1-carboxylic acid," Orig, Biomol. Chem., vol. 14, pp. 9485-9489, 2016.
Wang, et al., "Diamondoid-structured polymolybdate-based metal-organic frameworks as high-capacity anodes for lithium-ion batteries," Chem. Commun., vol. 53, pp. 5204-5207, 2017.
Zhao, et al., "Design, synthesis and evaluation of aromatic heterocyclic derivatives as potent antifungal agents," European Journal of Medicinal Chemistry, vol. 137, pp. 96-107, 2017.
Asnagli et al., "CTP Synthase 1 Is a Novel Target in T Cell Cancers, With Small Molecule Inhibition Inducing Death of Neoplastic Human T Cells in Vitro and Inhibition of Their Growth in an in Vivo Xenotransplant Model", European Hematology Association 2022 (abstract and poster).
Asnagli et al., "CTP Synthase 1 Is a Novel Therapeutic Target in Lymphoma", HemaSphere (2023) 7:4(e864). http://dx.doi.org/10.1097/HS9.0000000000000864.
Asnagli et al., "Inhibition of CTP Synthase 1 (CTPS1) blocks T- and B-cell proliferation in vitro and the inflammatory response in vivo in a delayed-type hypersensitivity model", Autoimmunity Congress 2021 (abstract and slides).
Asnagli et al., "Selective Small Molecule Inhibition of CTP Synthase 1 (CTPS1) Suppresses T Cell Proliferation and Cytokine Release, Highlighting a Novel Therapeutic Target for Graft-Versus-Host Disease", European Hematology Association 2022 (abstract and poster).
Beer et al., "STP938, a clinic ready, first in class inhibitor of CTP Synthase 1 (CTPS1), demonstrates efficacy in preclinical models of human T cell neoplasia", T-cell Lymphoma forum 2022 (abstract, poster and slides).
Chiron et al., "STP938, a selective CTPS1 inhibitor, shows single agent activity and synergy with BCL2 inhibition in preclinical models of mantle cell lymphoma", American Society for Hematology 2022 (abstract and poster).
Minet et al., "Differential roles of CTP synthetases CTPS1 and CTPS2 in cell proliferation", Life Sciences Alliance 2023 vol 6 | No. 9 | e202302066, https://doi.org/10.26508/lsa.202302066.
Novak et al., "Discovery and Optimization of Potent and Orally Available CTP Synthetase Inhibitors for Use in Treatment of Diseases Driven by Aberrant Immune Cell Proliferation" J Med Chem. Dec. 22, 2022;65(24):16640-16650. doi: 10.1021/acs.jmedchem.2c01446. (Abstract).
Novak, "Discovery and Optimisation of Potent and Orally Available CTP Synthetase Inhibitors", 4th Alpine Winter Conference on Medicinal and Synthetic Chemistry 2024 (poster).
Novak, "From hammer to scalpel: Honing a blunt instrument into a precision therapeutic", Acs San Francisco Poster 2023 (slides).
Parker et al., "Combined CTPS1 + DDR pathway inhibition delivers synergistic anti-cancer activity", DDR Inhibitors Summit 2023 (poster).
Parker et al., "Inhibition of CTP Synthase 1 (CTPS1) is a Targeted Therapy for Metabolic Vulnerability in de novo Nucleotide Synthesis for Lymphomas and Leukemias", American Society of Hematology, 2021 (abstract and slides).
Pfeiffer et al., "CTPS1 is a novel therapeutic target in multiple myeloma which synergizes with inhibition of CHEK1, ATR or WEE1", Leukemia 2023 38181 192 https://doi.org/10.1038/s41375-023-02071-z.
Pfeiffer et al., "CTPS1 Is a Novel Therapeutic Target inMultiple Myeloma That Synergizes withInhibition of ATR, CHEK1 or WEE1", American Society for Hematology 2022 (abstract and poster).
Pfeiffer et al., "Tackling pyrimidine biosynthesis—CTP Synthase 1 is a novel target in the treatment of multiple myeloma", International Myeloma Workshop 2021 (abstract and poster).
Schimmel et al., "Cyclopentenyl cytosine (CPEC): an overview of its in vitro and in vivo activity" Curr Cancer Drug Targets. Aug. 2007;7(5):504-9. doi: 10.2174/156800907781386579 (Abstract).
Walther, et al., "Prodrugs in medicinal chemistry and enzyme prodrug therapies", Adv Drug Deliv Rev. Sep. 1, 2017:118:65-77. doi: 10.1016/j.addr.2017.06.013.

* cited by examiner

COMPOUNDS

RELATED APPLICATIONS

This application is a continuation of U.S. application Ser. No. 16/767,379, now allowed, which is a National Phase Application under 35 U.S.C. § 371 of International Application No. PCT/EP2018/083140, filed Nov. 30, 2018, which claims priority to, and the benefit of, European Application No. 17204796.1, filed Nov. 30, 2017, European Application No. 18163766.1, filed Mar. 23, 2018, and European Application No. 18175823.6, filed Jun. 4, 2018. The contents of each of these applications are incorporated herein by reference in their entirety.

FIELD OF THE INVENTION

The invention relates to novel benzamide compounds, processes for the manufacture of such compounds, related intermediates, compositions comprising such compounds and the use of such compounds as cytidine triphosphate synthase 1 inhibitors, particularly in the treatment or prophylaxis of disorders associated with cell proliferation.

BACKGROUND OF THE INVENTION

Nucleotides are a key building block for cellular metabolic processes such as deoxyribonucleic acid (DNA) and ribonucleic acid (RNA) synthesis. There are two classes of nucleotides, that contain either purine or pyrimidine bases, both of which are important for metabolic processes. Based on this, many therapies have been developed to target different aspects of nucleotide synthesis, with some inhibiting generation of purine nucleotides and some pyrimidine nucleotides or both.

The pyrimidine nucleotide cytidine 5' triphosphate (CTP) is a precursor required not just for the metabolism of DNA and RNA but also phospholipids and sialyation of proteins. CTP originates from two sources: a salvage pathway and a de novo synthesis pathway that depends on two enzymes, the CTP synthases (or synthetases) 1 and 2 (CTPS1 and CTPS2) (Evans and Guy 2004; Higgins, et al. 2007; Ostrander, et al. 1998).

CTPS1 and CTPS2 catalyse the conversion of uridine triphosphate (UTP) and glutamine into cytidine triphosphate (CTP) and L-glutamate:

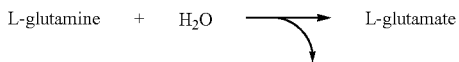

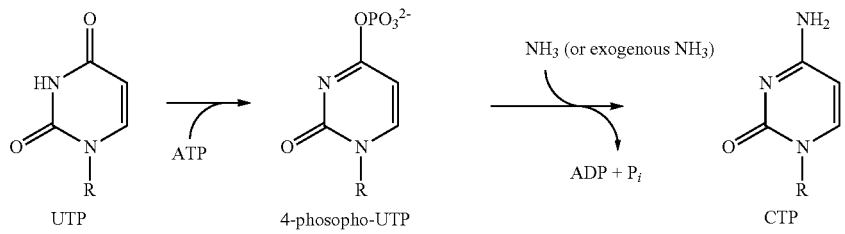

Both enzymes have two domains, an N-terminal synthetase domain and a C-terminal glutaminase domain (Kursula, et al. 2006). The synthetase domain transfers a phosphate from adenosine triphosphate (ATP) to the 4-position of UTP to create an activated intermediate, 4-phospho-UTP. The glutaminase domain generates ammonia from glutamine, via a covalent thioester intermediate with a conserved active site cysteine, generating glutamate. This ammonium is transferred from the glutaminase domain to the synthetase domain via a tunnel or can be derived from external ammonium. This ammonium is then used by the synthetase domain to generate CTP from the 4-phospho-UTP (Lieberman, 1956).

Although CTPS exists as two isozymes in humans and other eukaryotic organisms, CTPS1 and CTPS2, functional differences between the two isozymes are not yet fully elucidated (van Kuilenburg, et al. 2000).

The immune system provides protection from infections and has therefore evolved to rapidly respond to the wide variety of pathogens that the individual may be exposed to. This response can take many forms, but the expansion and differentiation of immune populations is a critical element and is hence closely linked to rapid cell proliferation. Within this, CTP synthase activity appears to play an important role in DNA synthesis and the rapid expansion of lymphocytes following activation (Fairbanks, et al. 1995; van den Berg, et al. 1995).

Strong clinical validation that CTPS1 is the critical enzyme in human lymphocyte proliferation came with the identification of a loss-of-function homozygous mutation (rs145092287) in this enzyme that causes a distinct and life-threatening immunodeficiency, characterized by an impaired capacity of activated T- and B-cells to proliferate in response to antigen receptor-mediated activation. Activated CTPS1-deficient cells were shown to have decreased levels of CTP. Normal T-cell proliferation was restored in CTPS1-deficient cells by expressing wild-type CTPS1 or by addition of exogenous CTP or its nucleoside precursor, cytidine. CTPS1 expression was found to be low in resting lymphocytes, but rapidly upregulated following activation of these cells. Expression of CTPS1 in other tissues was generally low. CTPS2 seems to be ubiquitously expressed in a range of cells and tissues but at low levels, and the failure of CTPS2, which is still intact in the patients, to compensate for the mutated CTPS1, supports CTPS1 being the critical enzyme for the immune populations affected in the patients (Martin, et al. 2014).

Overall, these findings suggest that CTPS1 is a critical enzyme necessary to meet the demands for the supply of CTP required by several important immune cell populations.

Normally the immune response is tightly regulated to ensure protection from infection, whilst controlling any response targeting host tissues. In certain situations, the control of this process is not effective, leading to immune-mediated pathology. A wide range of human diseases are thought to be due to such inappropriate responses mediated by different elements of the immune system.

Given the role that cell populations, such as T and B lymphocytes, are thought to play in a wide range of autoimmune and other diseases, CTPS1 represents a target for a new class of immunosuppressive agents. Inhibition of CTPS1 therefore provides a novel approach to the inhibition of activated lymphocytes and selected other immune cell populations such as Natural Killer cells, Mucosal-Associated Invariant T (MAIT) and Invariant Natural Killer T cells, highlighted by the phenotype of the human mutation patients (Martin, et al. 2014).

Cancer can affect multiple cell types and tissues but the underlying cause is a breakdown in the control of cell division. This process is highly complex, requiring careful coordination of multiple pathways, many of which remain to be fully characterised. Cell division requires the effective replication of the cell's DNA and other constituents. Interfering with a cell's ability to replicate by targeting nucleic acid synthesis has been a core approach in cancer therapy for many years. Examples of therapies acting in this way are 6-thioguanine, 6-mecaptopurine, 5-fluorouracil, cytarabine, gemcitabine and pemetrexed.

As indicated above, pathways involved in providing the key building blocks for nucleic acid replication are the purine and pyrimidine synthesis pathways, and pyrimidine biosynthesis has been observed to be up-regulated in tumors and neoplastic cells.

CTPS activity is upregulated in a range of tumour types of both haematological and non-haematological origin, although heterogeneity is observed among patients. Linkages have also been made between high enzyme levels and resistance to chemotherapeutic agents.

Currently, the precise role that CTPS1 and CTPS2 may play in cancer is not completely clear. Several non-selective CTPS inhibitors have been developed for oncology indications up to phase I/II clinical trials, but were stopped due to toxicity and efficacy issues.

Most of the developed inhibitors are nucleoside-analogue prodrugs (3-deazauridine, CPEC, carbodine), which are converted to the active triphosphorylated metabolite by the kinases involved in pyrimidine biosynthesis: uridine/cytidine kinase, nucleoside monophosphate-kinase (NMP-kinase) and nucleoside diphosphatekinase (NDP-kinase). The remaining inhibitors (acivicin, DON) are reactive analogues of glutamine, which irreversibly inhibit the glutaminase domain of CTPS. Gemcitibine is also reported to have some inhibitory activity against CTPS (McClusky et al., 2016).

CTPS therefore appears to be an important target in the cancer field. The nature of all of the above compounds is such that effects on other pathways are likely to contribute to the efficacy they show in inhibiting tumours.

Selective CTPS inhibitors therefore offer an attractive alternative approach for the treatment of tumours. Compounds with different potencies against CTPS1 and CTPS2 may offer important opportunities to target different tumours depending upon their relative dependence on these enzymes.

CTPS1 has also been suggested to play a role in vascular smooth muscle cell proliferation following vascular injury or surgery (Tang et al., 2013).

As far as is known to date, no selective CTPS1 inhibitors have been developed. Recently, the CTPS1 selective inhibitory peptide CTpep-3 has been identified. The inhibitory effects of CTpep-3 however, were seen in cell free assays but not in the cellular context. This was not unexpected though, since the peptide is unlikely to enter the cell and hence is not easily developable as a therapeutic (Sakamoto, et al. 2017).

In summary, the available information and data strongly suggest that inhibitors of CTPS1 will reduce the proliferation of a number of immune and cancer cell populations, with the potential for an effect on other selected cell types such as vascular smooth muscle cells as well. Inhibitors of CTPS1 may therefore be expected to have utility for treatment or prophylaxis in a wide range of indications where the pathology is driven by these populations.

CTPS1 inhibitors represent a novel approach for inhibiting selected components of the immune system in various tissues, and the related pathologies or pathological conditions such as, in general terms, rejection of transplanted cells and tissues, Graft-related diseases or disorders, allergies and autoimmune diseases. In addition, CTPS1 inhibitors offer therapeutic potential in a range of cancer indications and in enhancing recovery from vascular injury or surgery and reducing morbidity and mortality associated with neointima and restenosis.

SUMMARY OF THE INVENTION

The invention provides a compound of formula (I):

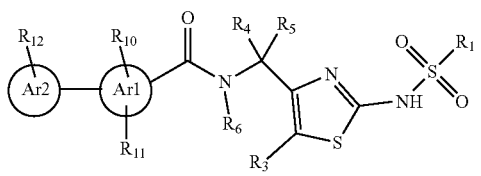

(I)

wherein
$R_1$ is $C_{1-5}$alkyl, $C_{0-2}$alkylene$C_{3-5}$cycloalkyl which cycloalkyl is optionally substituted by $CH_3$, $C_{1-3}$alkyleneO$C_{1-2}$alkyl, or $CF_3$;
$R_3$ is H, $CH_3$, halo, O$C_{1-2}$alkyl or $CF_3$;
$R_4$ and $R_5$ are each independently H, $C_{1-6}$alkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, $C_{1-6}$alkylOH or $C_{1-6}$haloalkyl,
or $R_4$ and $R_5$ together with the carbon atom to which they are attached form a $C_{3-6}$cycloalkyl or $C_{3-6}$heterocycloalkyl ring;
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, O$C_{1-2}$alkyl, $C_{1-2}$haloalkyl, O$C_{1-2}$ haloalkyl or CN;
$R_{11}$ is H, F, Cl, $CH_3$, ethyl, O$CH_3$, $CF_3$, O$CF_3$ or CN;
$R_{12}$ is attached to Ar2 in the meta or ortho position relative to Ar1 and $R_{12}$ is H, halo, $C_{1-4}$alkyl, $C_{2-4}$alkynyl, C(=O)$C_{1-2}$alkyl, $C_{0-2}$alkylene$C_{3-5}$cycloalkyl, O$C_{1-4}$alkyl, $C_{1-3}$alkyleneO$C_{1-3}$alkyl, $C_{1-4}$haloalkyl, O$C_{1-4}$haloalkyl, CN, O$C_{0-2}$alkylene$C_{3-5}$cycloalkyl, O$CH_2CH_2N(CH_3)_2$, OH, $C_{1-4}$alkylOH, $NR_{23}R_{24}$, $SO_2CH_3$, C(O)N$(CH_3)_2$, NHC(O)$C_{1-3}$alkyl, or a $C_{3-6}$heterocycloalkyl comprising one nitrogen located at the point of attachment to Ar2, or $R_{12}$ together with a nitrogen atom to which it is attached forms an N-oxide ($N^+$—$O^-$);
$R_{23}$ is H or $C_{1-2}$alkyl; and
$R_{24}$ is H or $C_{1-2}$alkyl.
Suitably, there is provided a compound of formula (I):

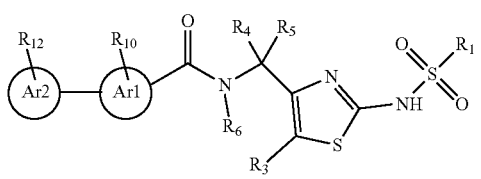

(I)

wherein
$R_1$ is $C_{1-4}$alkyl, $C_{1-2}$alkyleneO$C_{1-2}$alkyl or $C_{0-1}$alkylene$C_{3-4}$cycloalkyl which cycloalkyl is optionally substituted by $CH_3$;
$R_3$ is H, $CH_3$, F or Cl;
$R_4$ and $R_5$ are each independently H, $C_{1-4}$alkyl, $C_{0-2}$alkylene$C_{3-5}$cycloalkyl, $C_{1-3}$alkyleneO$C_{1-3}$alkyl, $C_{1-4}$alkylOH or $C_{1-4}$haloalkyl;
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, O$C_{1-2}$alkyl, $C_{1-2}$haloalkyl, O$C_{1-2}$ haloalkyl or CN; and
$R_{12}$ is attached to Ar2 in the meta position relative to Ar1 and $R_{12}$ is H, halo, $C_{1-4}$alkyl, $C_2$alkynyl, C(=O)$C_{1-2}$alkyl, $C_{0-2}$alkylene$C_{3-5}$cycloalkyl, O$C_{1-4}$alkyl, $C_{1-3}$alkyleneO$C_{1-3}$alkyl, $C_{1-4}$haloalkyl, O$C_{1-4}$haloalkyl or CN.

A compound of formula (I) may be provided in the form of a salt and/or solvate thereof and/or derivative thereof. Suitably, the compound of formula (I) may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Also provided is a compound of formula (I), or a pharmaceutically acceptable salt and/or solvate thereof and/or derivative thereof, for use as a medicament, in particular for use in the inhibition of CTPS1 in a subject or the prophylaxis or treatment of associated diseases or disorders, such as those in which a reduction in T-cell and/or B-cell proliferation would be beneficial.

Further, there is provided a method for the inhibition of CTPS1 in a subject or the prophylaxis or treatment of associated diseases or disorders, such as those in which a reduction in T-cell and/or B-cell proliferation would be beneficial, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the inhibition of CTPS1 in a subject or the prophylaxis or treatment of associated diseases or disorders, such as those in which a reduction in T-cell and/or B-cell proliferation would be beneficial.

Suitably the disease or disorder is selected from: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; and transplantation. In addition, the disease or disorder may be selected from myasthenia gravis, multiple sclerosis, and scleroderma/systemic sclerosis.

Also provided is a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Also provided is a compound of formula (I), or a pharmaceutically acceptable salt and/or solvate thereof and/or derivative thereof, for use in enhancing recovery from vascular injury or surgery and reducing morbidity and mortality associated with neointima and restenosis in a subject.

Further, there is provided a method for enhancing recovery from vascular injury or surgery and reducing morbidity and mortality associated with neointima and restenosis in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for enhancing recovery from vascular injury or surgery and reducing morbidity and mortality associated with neointima and restenosis in a subject.

Also provided are pharmaceutical compositions containing a compound of formula (I), or a pharmaceutically acceptable salt and/or solvate thereof and/or derivative thereof, and a pharmaceutically acceptable carrier or excipient.

Also provided are processes for preparing compounds of formula (I) and novel intermediates of use in the preparation of compounds of formula (I).

DETAILED DESCRIPTION OF THE INVENTION

The invention provides a compound of formula (I):

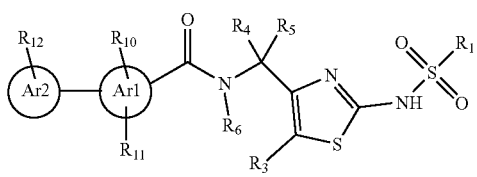

wherein
$R_1$ is $C_{1-5}$alkyl, $C_{0-2}$alkylene$C_{3-5}$cycloalkyl which cycloalkyl is optionally substituted by $CH_3$, $C_{1-3}$alkyleneO$C_{1-2}$alkyl, or $CF_3$;
$R_3$ is H, $CH_3$, halo, O$C_{1-2}$alkyl or $CF_3$;
$R_4$ and $R_5$ are each independently H, $C_{1-6}$alkyl, $C_{0-2}$alkylene$C_{3-6}$cycloalkyl, $C_{0-2}$alkylene$C_{3-6}$heterocycloalkyl, $C_{1-3}$alkyleneO$C_{1-3}$alkyl, $C_{1-6}$alkylOH or $C_{1-6}$haloalkyl,
or $R_4$ and $R_5$ together with the carbon atom to which they are attached form a $C_{3-6}$cycloalkyl or $C_{3-6}$heterocycloalkyl ring;
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, O$C_{1-2}$alkyl, $C_{1-2}$haloalkyl, O$C_{1-2}$ haloalkyl or CN;
$R_{11}$ is H, F, Cl, $CH_3$, ethyl, $OCH_3$, $CF_3$, $OCF_3$ or CN;
$R_{12}$ is attached to Ar2 in the meta or ortho position relative to Ar1 and $R_{12}$ is H, halo, $C_{1-4}$alkyl, $C_{2-4}$alkynyl, C(=O)$C_{1-2}$alkyl, $C_{0-2}$alkylene$C_{3-5}$cycloalkyl, O$C_{1-4}$alkyl, $C_{1-3}$alkyleneO$C_{1-3}$alkyl, $C_{1-4}$haloalkyl, O$C_{1-4}$haloalkyl, CN, O$C_{0-2}$alkylene$C_{3-5}$cycloalkyl, $OCH_2CH_2N(CH_3)_2$, OH, $C_{1-4}$alkylOH, $NR_{23}R_{24}$, $SO_2CH_3$, $C(O)N(CH_3)_2$, $NHC(O)C_{1-3}$alkyl, or a $C_{3-6}$heterocycloalkyl comprising one nitrogen located at the point of attachment to Ar2, or $R_{12}$ together with a nitrogen atom to which it is attached forms an N-oxide ($N^+$—$O^-$);
$R_{23}$ is H or $C_{1-2}$alkyl; and
$R_{24}$ is H or $C_{1-2}$alkyl;
or a salt and/or solvate thereof and/or derivative thereof.

Suitably, the invention provides a compound of formula (I):

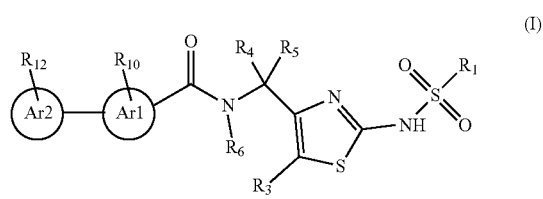

wherein
$R_1$ is $C_{1-4}$alkyl, $C_{1-2}$alkyleneO$C_{1-2}$alkyl or $C_{0-1}$alkylene$C_{3-4}$cycloalkyl which cycloalkyl is optionally substituted by $CH_3$;
$R_3$ is H, $CH_3$, F or Cl;
$R_4$ and $R_5$ are each independently H, $C_{1-4}$alkyl, $C_{0-2}$alkylene$C_{3-5}$cycloalkyl, $C_{1-3}$alkyleneO$C_{1-3}$alkyl, $C_{1-4}$alkylOH or $C_{1-4}$haloalkyl;
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, O$C_{1-2}$alkyl, $C_{1-2}$haloalkyl, O$C_{1-2}$ haloalkyl or CN; and
$R_{12}$ is attached to Ar2 in the meta position relative to Ar1 and $R_{12}$ is H, halo, $C_{1-4}$alkyl, $C_2$alkynyl, C(=O)$C_{1-2}$alkyl, $C_{0-2}$alkylene$C_{3-5}$cycloalkyl, O$C_{1-4}$alkyl, $C_{1-3}$alkyleneO$C_{1-3}$alkyl, $C_{1-4}$haloalkyl, O$C_{1-4}$haloalkyl or CN;
or a salt and/or solvate thereof and/or derivative thereof.

Suitably, the invention provides a compound of formula (I):

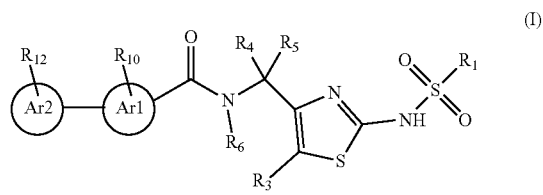

wherein
$R_1$ is $C_{0-1}$alkylene$C_{3-4}$cycloalkyl;
$R_3$ is H, $CH_3$ or Cl;
$R_4$ and $R_5$ are each independently H, $C_{1-4}$alkyl or $C_{1-3}$alkyleneO$C_{1-3}$alkyl;
or $R_4$ together with $R_5$ form a $C_{3-6}$cycloalkyl ring
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, O$C_{1-2}$alkyl or $C_{1-2}$haloalkyl; and
$R_{12}$ is attached to Ar2 in the meta position relative to Ar1 and $R_{12}$ is H, halo, $C_{1-4}$alkyl, C(=O)$C_{1-2}$alkyl, O$C_{1-4}$alkyl, $C_{1-4}$haloalkyl, O$C_{1-4}$haloalkyl or CN;
or a salt and/or solvate thereof and/or derivative thereof.

The term 'alkyl' as used herein, such as in $C_{1-2}$alkyl, $C_{1-3}$alkyl or $C_{1-4}$alkyl, whether alone or forming part of a larger group such as an Oalkyl group (e.g. $OC_{1-2}$alkyl, $OC_{1-3}$alkyl or $OC_{1-4}$alkyl), is a straight or a branched fully saturated hydrocarbon chain containing the specified number of carbon atoms. Examples of alkyl groups include the $C_{1-4}$alkyl groups methyl, ethyl, n-propyl, iso-propyl, n-butyl, iso-butyl, sec-butyl and tert-butyl, in particular the $C_{1-3}$alkyl groups methyl, ethyl, n-propyl and iso-propyl such as $C_{1-2}$alkyl groups methyl and ethyl. Reference to "propyl" includes n-propyl and iso-propyl, and reference to "butyl" includes n-butyl, isobutyl, sec-butyl and tert-butyl. Examples of Oalkyl groups include the $OC_{1-4}$alkyl groups methoxy, ethoxy, propoxy (which includes n-propoxy and iso-propoxy) and butoxy (which includes n-butoxy, iso-butoxy, sec-butoxy and tert-butoxy). $C_5$alkyl groups as used herein, whether alone or forming part of a larger group such as an $OC_5$alkyl group is a straight or a branched fully saturated hydrocarbon chain containing five carbon atoms. Examples of $C_5$alkyl groups include n-pentyl, sec-pentyl, 3-pentyl, sec-isopentyl and active pentyl. $C_6$alkyl groups as used herein, whether alone or forming part of a larger group such as an $OC_6$alkyl group is a straight or a branched fully saturated hydrocarbon chain containing six carbon atoms. Examples of $C_6$alkyl groups include n-hexyl, 2-methylpentyl, 3-methylpentyl, 2,2-dimethylbutyl and 2,3-dimethylbutyl.

The term 'alkylene' as used herein, such as in $C_{0-2}$alkylene$C_{3-5}$cycloalkyl, $C_{1-3}$alkyleneO$C_{1-3}$alkyl, $C_{1-2}$alkyleneO$C_{1-2}$alkyl or $C_{0-1}$alkylene$C_{3-4}$cycloalkyl is a bifunctional straight or a branched fully saturated hydrocarbon chain containing the specified number of carbon atoms. Examples of $C_{0-2}$alkylene groups are where the group is absent (i.e. $C_0$), methylene ($C_1$) and ethylene ($C_2$). Examples of $C_{1-3}$alkylene groups are where the group is methylene ($C_1$), ethylene ($C_2$) and propylene ($C_3$). Examples of $C_{1-2}$alkylene groups are where the group is methylene ($C_1$) and ethylene ($C_2$). Examples of $C_{0-1}$alkylene groups are where the group is absent ($C_0$) and methylene ($C_1$).

The term 'cycloalkyl' as used herein, such as in $C_{3-6}$cycloalkyl, such as $C_{3-5}$cycloalkyl or $C_{3-4}$ cycloalkyl, whether alone or forming part of a larger group such as $C_{0-2}$alkylene$C_{3-6}$cycloalkyl such as $C_{0-2}$alkylene$C_{3-5}$cycloalkyl or $C_{0-1}$alkylene$C_{3-4}$cycloalkyl is a fully saturated hydrocarbon ring containing the specified number of carbon atoms. Examples of cycloalkyl groups include the $C_{3-5}$cycloalkyl groups cyclopropyl, cyclobutyl and cyclopentyl. Examples of cycloalkyl groups also include the $C_6$cycloalkyl group cyclohexyl.

Example 'cycloalkyl' groups are as follows:

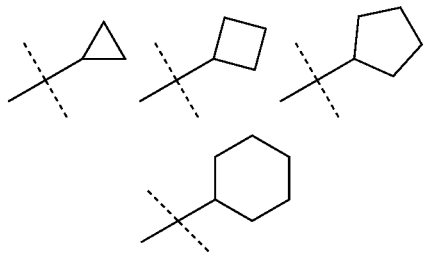

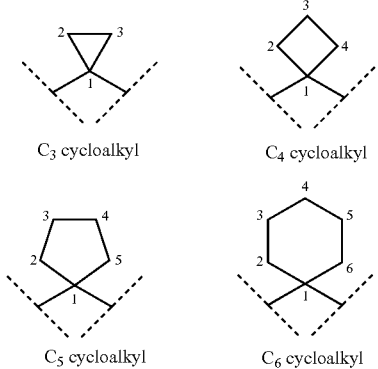

C$_3$ cycloalkyl
C$_4$ cycloalkyl
C$_5$ cycloalkyl
C$_6$ cycloalkyl

The term 'heterocycloalkyl' as used herein, such as in $C_{3-6}$heterocycloalkyl or $C_{0-2}$alkylene$C_{3-6}$ heterocycloalkyl is a fully saturated hydrocarbon ring containing the specified number of ring atoms and includes the ring atom through which the heterocycloalkyl group is attached, wherein at least one of the atoms in the ring is a heteroatom such as O, N or S. As required by valency, the nitrogen atom(s) may be connected to a hydrogen atom to form an NH group. Alternatively the nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Wherein a ring heteroatom is S, the term 'heterocycloalkyl' includes wherein the S atom(s) is substituted (such as one S atom is substituted) by one or two oxygen atoms (i.e. S(O) or S(O)$_2$). Alternatively, any sulphur atom(s) in the $C_{3-6}$heterocycloalkyl ring is not substituted.

Examples of $C_{3-6}$heterocycloalkyl groups include those comprising one heteroatom such as containing one heteroatom (e.g. one oxygen atom or one nitrogen atom) or containing two heteroatoms (e.g. two oxygen atoms or one oxygen atom and one nitrogen atom or two nitrogen atoms). Particular examples of $C_{3-6}$heterocycloalkyl comprising one oxygen atom include oxiranyl, oxetanyl, 3-dioxolanyl, morpholinyl, 1,4-oxathianyl, tetrahydropyranyl, 1,4-thioxanyl and 1,3,5-trioxanyl. Particular examples of $C_{3-6}$heterocycloalkyl comprising one nitrogen atom include pyrrolidinyl, pyrazolidinyl, imidazolidinyl, thiazolidinyl, piperidinyl, piperazinyl, morpholinyl and thiomorpholinyl.

The heterocycloalkyl groups may have the following structures:

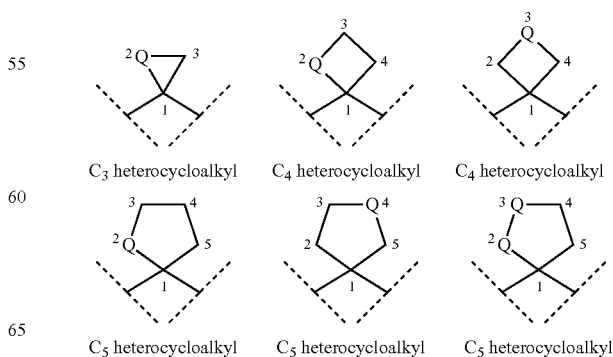

C$_3$ heterocycloalkyl
C$_4$ heterocycloalkyl
C$_4$ heterocycloalkyl
C$_5$ heterocycloalkyl
C$_5$ heterocycloalkyl
C$_5$ heterocycloalkyl

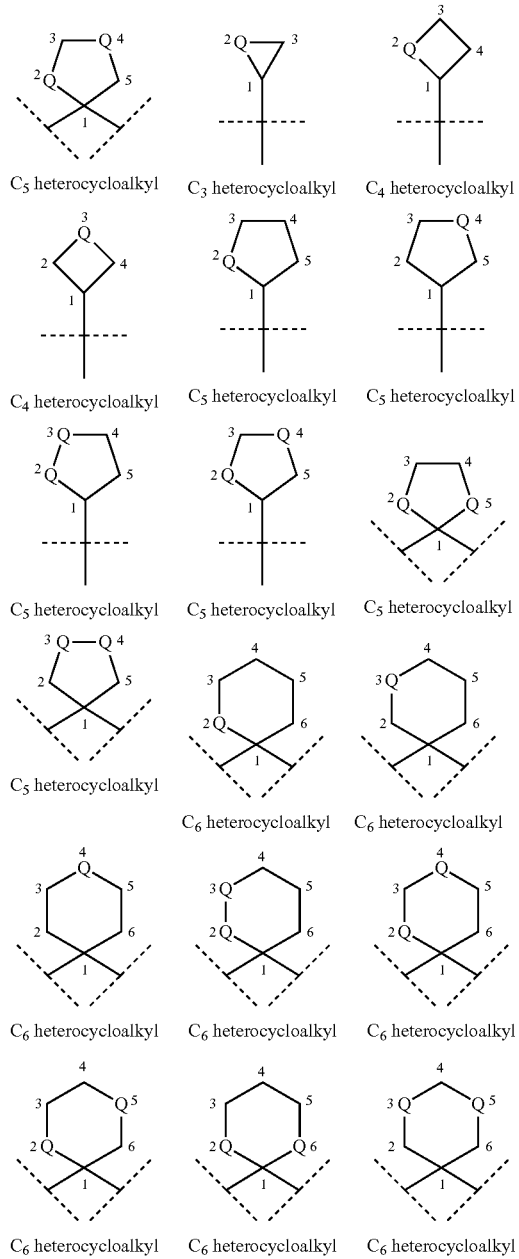

C₅ heterocycloalkyl, C₃ heterocycloalkyl, C₄ heterocycloalkyl, C₄ heterocycloalkyl, C₅ heterocycloalkyl, C₅ heterocycloalkyl, C₅ heterocycloalkyl, C₅ heterocycloalkyl, C₅ heterocycloalkyl, C₅ heterocycloalkyl, C₆ heterocycloalkyl, C₆ heterocycloalkyl, C₆ heterocycloalkyl, C₆ heterocycloalkyl, C₆ heterocycloalkyl, C₆ heterocycloalkyl, C₆ heterocycloalkyl, C₆ heterocycloalkyl wherein each Q is independently selected from O, N or S, such as O or N. When Q is N, as required by valency, the nitrogen atom(s) may be connected to a hydrogen atom to form an NH group. Alternatively the nitrogen atom(s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. When any Q is S, the S atoms can be substituted (such as one S atom is substituted) by one or two oxygen atoms (i.e. S(O) or S(O)$_2$). Alternatively, any sulphur atom(s) in the $C_{3-6}$heterocycloalkyl ring is not substituted.

When the heterocycloalkyl is formed from R₄ and R₅ together with the carbon atom to which they are attached, suitably any heteroatom is not directly connected to the carbon to which R₄ and R₅ are attached. Thus suitably, when the heterocycloalkyl is formed from R₄ and R₅ together with the carbon atom to which they are attached, the heterocycloalkyl may be:

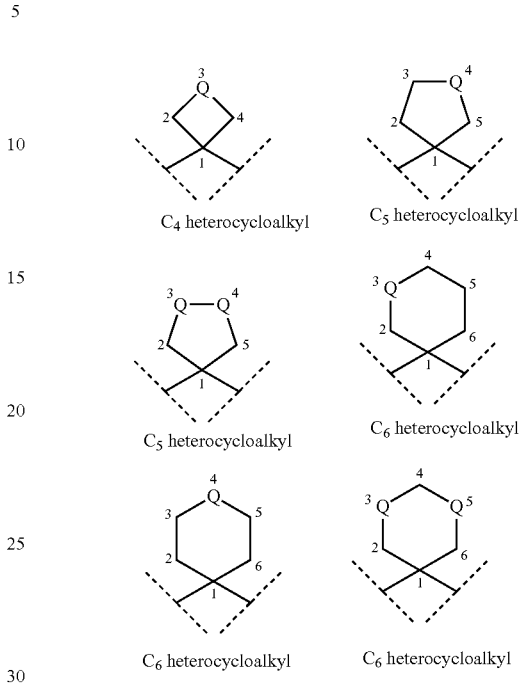

C₄ heterocycloalkyl, C₅ heterocycloalkyl, C₅ heterocycloalkyl, C₆ heterocycloalkyl, C₆ heterocycloalkyl, C₆ heterocycloalkyl wherein each Q is independently O, N or S such as O or N. When Q is N, as required by valency, the nitrogen atom(s) may be connected to a hydrogen atom to form an NH group. Alternatively the nitrogen atom (s) may be substituted (such as one nitrogen atom is substituted), for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$ alkylaryl such as C(O)NHBz, an Fmoc group, C(O)$C_{1-4}$ haloalkyl, C(O)O$C_{1-4}$haloalkyl or C(O)NH$C_{1-4}$haloalkyl such as C(O)OtBu. When any Q is S, the S atom(s) can be substituted (such as one S atom is substituted) by one or two oxygen atoms (i.e. S(O) or S(O)$_2$). Alternatively, any sulphur atom(s) in the $C_{3-6}$heterocycloalkyl ring is not substituted.

When R₄ and/or R₅ is $C_0$alkylene$C_{3-6}$heterocycloalkyl, any heteroatom in the heterocycloalkyl may not be directly connected to the carbon to which R₄ and R₅ are connected.

The term 'alkynyl' as used herein, such as in $C_{2-4}$alkynyl such as in $C_2$alkynyl is an unbranched hydrocarbon chain containing the specified number of carbons (e.g. 2, 3 or 4 carbons, such as two carbons), two of which carbon atoms are linked by a carbon-carbon triple bond.

The term 'halo' or 'halogen' as used herein, refers to fluorine, chlorine, bromine or iodine. Particular examples of halo are fluorine and chlorine, especially fluorine.

The term 'haloalkyl' as used herein, such as in $C_{1-6}$haloalkyl, such as in $C_{1-2}$haloalkyl or $C_{1-4}$haloalkyl, whether alone or forming part of a larger group such as an Ohaloalkyl group, such as in O$C_{1-6}$haloalkyl, such as in O$C_{1-2}$haloalkyl or O$C_{1-4}$haloalkyl, is a straight or a branched fully saturated hydrocarbon chain containing the specified number of carbon atoms and at least one halogen atom, such as fluoro or chloro, especially fluoro. An example of haloalkyl is $CF_3$.

Further examples of haloalkyl are $CHF_2$ and $CH_2CF_3$. Examples of Ohaloalkyl include $OCF_3$, $OCHF_2$ and $OCH_2CF_3$.

The term '6-membered aryl' as used herein refers to a phenyl ring.

The term '6-membered heteroaryl' as used herein refers to 6-membered aromatic rings containing at least one heteroatom (e.g. nitrogen). Exemplary 6-membered heteroaryls include one nitrogen atom (pyridinyl), two nitrogen atoms (pyridazinyl, pyrimidinyl or pyrazinyl) and three nitrogen atoms (triazinyl).

The phrase 'in the para position relative to the amide' as used herein, such as in relation to the position of Ar2, means that compounds with the following substructure are formed:

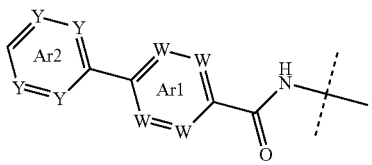

wherein W may be N, CH or $CR_{10}$, and Y may be N, CH or $CR_{12}$ as required by the definitions provided for compounds of formula (I). W may also be $CR_{11}$ as allowed by the definitions provided for compounds of formula (I).

The term 'meta' as used herein, such as when used in respect of defining the position of $R_{12}$ on Ar2 is with respect to Ar1 means:

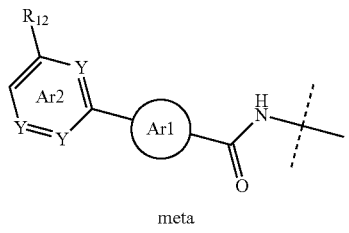

meta

The term 'ortho' as used herein, such as when used in respect of defining the position of $R_{12}$ on Ar2 is with respect to Ar1 means:

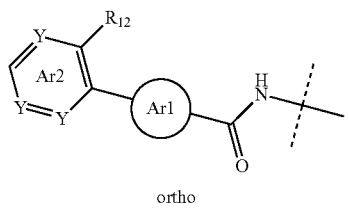

ortho

In one embodiment of the invention $R_1$ is $C_{1-5}$alkyl such as $C_{1-4}$alkyl. When $R_1$ is $C_{1-5}$alkyl, $R_1$ is methyl, ethyl, propyl (n-propyl or isopropyl), butyl (n-butyl, isobutyl, sec-butyl or tert-butyl) or pentyl (e.g. n-pentyl, sec-pentyl, 3-pentyl, sec-isopentyl or active pentyl). When $R_1$ is $C_{1-4}$alkyl, $R_1$ is methyl, ethyl, propyl (n-propyl or isopropyl) or butyl (n-butyl, isobutyl, sec-butyl or tert-butyl).

In a second embodiment of the invention $R_1$ is $C_{1-3}$alkyleneO$C_{1-2}$alkyl such as $C_{1-2}$alkyleneO$C_{1-2}$alkyl. $R_1$ may be $C_1$alkyleneO$C_1$alkyl. $R_1$ may be $C_1$alkyleneO$C_2$alkyl. $R_1$ may be $C_2$alkyleneO$C_1$alkyl. $R_1$ may be $C_2$alkyleneO$C_2$alkyl. $R_1$ may be $C_3$alkyleneO$C_1$alkyl. $R_1$ may be $C_3$alkyleneO$C_2$alkyl.

In a third embodiment of the invention $R_1$ is $C_{0-2}$alkylene$C_{3-5}$cycloalkyl which cycloalkyl is optionally substituted by $CH_3$ such as $C_{0-1}$alkylene$C_{3-4}$cycloalkyl which cycloalkyl is optionally substituted by $CH_3$. In some embodiments, $R_1$ is $C_{0-2}$alkylene$C_{3-5}$cycloalkyl such as $C_{0-1}$alkylene$C_{3-4}$cycloalkyl. In other embodiments, $R_1$ is $C_{0-2}$alkylene$C_{3-5}$cycloalkyl which cycloalkyl is substituted by $CH_3$ such as $C_{0-1}$alkylene$C_{3-4}$cycloalkyl which cycloalkyl is substituted by $CH_3$. $R_1$ may be $C_{3-5}$cycloalkyl, which cycloalkyl is optionally substituted by $CH_3$ such as $C_{3-4}$cycloalkyl, which cycloalkyl is optionally substituted by $CH_3$. $R_1$ may be $C_1$alkylene$C_{3-5}$cycloalkyl, which cycloalkyl is optionally substituted by $CH_3$. $R_1$ may be $C_1$alkylene$C_{3-4}$cycloalkyl, which cycloalkyl is optionally substituted by $CH_3$. $R_1$ may be $C_2$alkylene$C_{3-5}$cycloalkyl, which cycloalkyl is optionally substituted by $CH_3$. $R_1$ may be $C_2$alkylene$C_{3-4}$cycloalkyl, which cycloalkyl is optionally substituted by $CH_3$. $R_1$ may be $C_{0-2}$alkylene$C_3$cycloalkyl, which cycloalkyl is optionally substituted by $CH_3$. $R_1$ may be $C_{0-1}$alkylene$C_3$cycloalkyl, which cycloalkyl is optionally substituted by $CH_3$. $R_1$ may be $C_{0-2}$alkylene$C_4$cycloalkyl, which cycloalkyl is optionally substituted by $CH_3$. $R_1$ may be $C_{0-1}$alkylene$C_4$cycloalkyl, which cycloalkyl is optionally substituted by $CH_3$. $R_1$ may be $C_{0-2}$alkylene$C_5$cycloalkyl, which cycloalkyl is optionally substituted by $CH_3$. $R_1$ may be $C_{0-1}$alkylene$C_5$cycloalkyl, which cycloalkyl is optionally substituted by $CH_3$. Suitably, where $C_{0-2}$alkylene$C_{3-5}$cycloalkyl such as $C_{0-1}$alkylene$C_{3-4}$cycloalkyl is optionally substituted by $CH_3$, the $CH_3$ is at the point of attachment of the $C_{3-5}$cycloalkyl to the $C_{0-2}$alkylene such as at the point of attachment of the $C_{3-4}$cycloalkyl to the $C_{0-1}$alkylene.

Suitably $R_1$ is cyclopropyl.

In a fourth embodiment of the invention, $R_1$ is $CF_3$.

In one embodiment $R_3$ is H. In a second embodiment $R_3$ is $CH_3$. In a third embodiment, $R_3$ is halo. In an example, $R_3$ is F. In a second example, $R_3$ is Cl. In a fourth embodiment, $R_3$ is $OC_{1-2}$alkyl. Suitably $R_3$ is $OCH_3$. Suitably, $R_3$ is $OCH_2CH_3$. In a fifth embodiment, $R_3$ is $CF_3$.

Suitably, $R_3$ is H.

In one embodiment, $R_4$ is H. In a second embodiment $R_4$ is $C_{1-6}$alkyl such as $C_{1-4}$alkyl, i.e. methyl, ethyl, propyl (n-propyl or isopropyl) or butyl (n-butyl, isobutyl, sec-butyl or tert-butyl). $R_4$ may also be pentyl (e.g. n-pentyl, sec-pentyl, 3-pentyl, sec-isopentyl or active pentyl) or hexyl (e.g. n-hexyl, 2-methylpentyl, 3-methylpentyl, 2,2-dimethylbutyl and 2,3-dimethylbutyl). In a third embodiment, $R_4$ is $C_{0-2}$alkylene$C_{3-6}$cycloalkyl such as $C_{0-2}$alkylene$C_{3-5}$cycloalkyl, such as $C_{0-2}$alkylene$C_3$cycloalkyl, $C_{0-2}$alkylene$C_4$cycloalkyl, $C_{0-2}$alkylene$C_5$cycloalkyl, $C_0$alkylene$C_{3-5}$cycloalkyl, $C_1$alkylene$C_{3-5}$cycloalkyl and $C_2$alkylene$C_{3-5}$cycloalkyl. $R_4$ may also be $C_{0-2}$alkylene$C_3$cycloalkyl, $C_{0-2}$alkylene$C_{3-6}$cycloalkyl, $C_1$alkylene$C_{3-6}$cycloalkyl and $C_2$alkylene$C_{3-6}$cycloalkyl. In a fourth embodiment $R_4$ is $C_{1-3}$alkyleneO$C_{1-3}$alkyl, in particular $C_{1-2}$alkyleneO$C_{1-2}$alkyl such as $C_1$alkyleneO$C_1$alkyl, $C_2$alkyleneO$C_1$alkyl, $C_1$alkyleneO$C_2$alkyl or $C_2$alkyleneO$C_2$alkyl. In a fifth embodiment $R_4$ is $C_{1-6}$alkylOH such as $C_{1-4}$alkylOH such as $C_1$alkylOH, $C_2$alkylOH, $C_3$alkylOH or $C_4$alkylOH wherein $C_{1-4}$alkyl is methyl, ethyl, propyl (n-propyl or isopropyl) and butyl (n-butyl, isobutyl, sec-butyl or tert-butyl). $R_4$ may also be $C_5$alkylOH or $C_2$alkylOH. In a sixth embodiment, $R_4$ is $C_{1-6}$haloalkyl such as $C_{1-4}$haloalkyl such as $C_1$haloalkyl (e.g. $CF_3$), $C_2$haloalkyl (e.g. $CH_2CF_3$), $C_3$haloalkyl (e.g. $CH_2CH_2CF_3$) or $C_4$haloalkyl (e.g. $CH_2CH_2CH_2CF_3$). $R_4$ may also be $C_5$haloalkyl (e.g. $CH_2CH_2CH_2CH_2CF_3$) or $C_5$haloalkyl (e.g. $CH_2CH_2CH_2CH_2CH_2CF_3$). In a seventh embodiment, $R_4$ is $C_{0-2}$alkylene$C_{3-6}$ heterocycloalkyl such as $C_{0-2}$alkylene$C_3$heterocycloalkyl, $C_{0-2}$alkylene$C_4$heterocycloalkyl, $C_{0-2}$alkylene$C_5$heterocycloalkyl, $C_{0-2}$alkylene$C_6$heterocycloalkyl, $C_0$alkylene$C_{3-6}$heterocycloalkyl, $C_1$alkylene$C_{3-6}$heterocycloalkyl and $C_2$alkylene$C_{3-6}$heterocycloalkyl. Suitably the heterocycloalkyl of a $C_{0-2}$alkylene$C_{3-6}$heterocycloalkyl group is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$ haloalkyl such as C(O)OtBu. Suitably, any nitrogen atom in the $C_{3-6}$heterocycloalkyl ring is not substituted. In an eighth embodiment, $R_4$ and $R_5$ together with the carbon atom to which they are attached form a $C_{3-6}$cycloalkyl or $C_{3-6}$heterocycloalkyl ring. Suitably $R_4$ and $R_5$ together with the carbon atom to which they are attached form a $C_{3-6}$cycloalkyl ring, such as a cyclopropyl, cyclobutyl, cyclopentyl or cyclohexyl ring. Suitably $R_4$ and $R_5$ together with the carbon atom to which they are attached form a $C_{3-6}$heterocycloalkyl ring, such as a heterocyclopropyl, heterocyclobutyl, heterocyclopentyl or heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen atom in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Suitably, any nitrogen atom in the $C_{3-6}$heterocycloalkyl ring is not substituted.

Suitably $R_4$ is H, $CH_3$ or ethyl, in particular $CH_3$ or ethyl. Suitably, $R_4$ and $R_5$ together with the carbon atom to which they are attached form a $C_{3-6}$cycloalkyl ring, such as a cyclopropyl ring.

In one embodiment, $R_5$ is H. In a second embodiment $R_5$ is $C_{1-6}$alkyl such as $C_{1-4}$alkyl, i.e. methyl, ethyl, propyl (n-propyl or isopropyl) or butyl (n-butyl, isobutyl, sec-butyl or tert-butyl). $R_5$ may also be pentyl (e.g. n-pentyl, sec-pentyl, 3-pentyl, sec-isopentyl and active pentyl) or hexyl (e.g. n-hexyl, 2-methylpentyl, 3-methylpentyl, 2,2-dimethylbutyl and 2,3-dimethylbutyl). In a third embodiment, $R_5$ is $C_{0-2}$alkylene$C_{3-6}$cycloalkyl such as $C_{0-2}$alkylene$C_{3-5}$cycloalkyl, such as $C_{0-2}$alkylene$C_3$cycloalkyl, $C_{0-2}$alkylene$C_4$cycloalkyl, $C_{0-2}$alkylene$C_{3-5}$cycloalkyl, $C_0$alkylene$C_{3-5}$cycloalkyl, $C_1$alkylene$C_{3-5}$cycloalkyl and $C_2$alkylene$C_{3-5}$cycloalkyl. $R_5$ may also be $C_{0-2}$alkylene$C_6$cycloalkyl, $C_0$alkylene$C_{3-6}$cycloalkyl, $C_1$alkylene$C_{3-6}$cycloalkyl and $C_2$alkylene$C_{3-6}$ cycloalkyl. In a fourth embodiment $R_5$ is $C_{1-3}$alkyleneO$C_{1-3}$alkyl, in particular $C_{1-2}$alkyleneO$C_{1-2}$ alkyl such as $C_1$alkyleneO$C_1$alkyl, $C_2$alkyleneO$C_1$alkyl, $C_1$alkyleneO$C_2$alkyl or $C_2$alkyleneO$C_2$alkyl. In a fifth embodiment $R_5$ is $C_{1-6}$alkylOH such as $C_{1-4}$alkylOH such as $C_1$alkylOH, $C_2$alkylOH, $C_3$alkylOH or $C_4$alkylOH wherein $C_{1-4}$alkyl is methyl, ethyl, propyl (n-propyl or isopropyl) and butyl (n-butyl, isobutyl, sec-butyl or tert-butyl). $R_5$ may also be $C_5$alkylOH or $C_6$alkylOH. In a sixth embodiment, $R_5$ is $C_{1-6}$haloalkyl such as $C_{1-4}$haloalkyl such as $C_1$haloalkyl (e.g. $CF_3$), $C_2$haloalkyl (e.g. $CH_2CF_3$), $C_3$haloalkyl (e.g. $CH_2CH_2CF_3$), $C_4$haloalkyl (e.g. $CH_2CH_2CH_2CF_3$). $R_5$ may also be $C_5$haloalkyl (e.g. $CH_2CH_2CH_2CH_2CF_3$) or $C_6$haloalkyl (e.g. $CH_2CH_2CH_2CH_2CH_2CF_3$). In a seventh embodiment, $R_5$ is $C_{0-2}$alkylene$C_{3-6}$heterocycloalkyl such as $C_{0-2}$alkylene$C_3$heterocycloalkyl, $C_{0-2}$alkylene$C_4$heterocycloalkyl, $C_{0-2}$alkylene$C_5$heterocycloalkyl, $C_{0-2}$alkylene$C_6$heterocycloalkyl, $C_0$alkylene$C_{3-6}$heterocycloalkyl, $C_1$alkylene$C_{3-6}$heterocycloalkyl and $C_2$alkylene$C_{3-6}$heterocycloalkyl. Suitably the heterocycloalkyl is a heterocyclopropyl, heterocyclobutyl, heterocyclopentyl or heterocyclohexyl ring such as a heterocyclohexyl ring. Suitably, the heterocyclopentyl ring is tetrahydrofuranyl or pyrrolidinyl. Suitably, the heterocyclohexyl ring is tetrahydropyranyl or piperidinyl. Any nitrogen atom such as one nitrogen in the $C_{3-6}$heterocycloalkyl ring may be substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$alkyl, C(O)NH$C_{1-4}$alkylaryl such as C(O)NHBz, an Fmoc group, C(O)$C_{1-4}$haloalkyl, C(O)O$C_{1-4}$haloalkyl or C(O)NH$C_{1-4}$haloalkyl such as C(O)OtBu. Suitably, any nitrogen atom in the $C_{3-6}$heterocycloalkyl ring is not substituted.

Suitably $R_5$ is H, $CH_3$ or ethyl, in particular $CH_3$ or ethyl. Suitably, $R_4$ and $R_5$ together with the carbon atom to which they are attached form a $C_{3-6}$cycloalkyl ring, such as a cyclopropyl ring.

Suitably $R_4$ is H, $CH_3$ or ethyl and $R_5$ is H, $CH_3$ or ethyl, in particular $R_4$ is $CH_3$ or ethyl and $R_5$ is $CH_3$ or ethyl. For example, $R_4$ and $R_5$ are H, $R_4$ and $R_5$ are methyl or $R_4$ and $R_5$ are ethyl.

Suitably, $R_4$ is $CH_2CH_2OCH_3$ and $R_5$ is H.

In one embodiment, $R_6$ is H. In another embodiment, $R_6$ is $C_{1-3}$alkyl, in particular $CH_3$.

In one embodiment Ar1 is a 6-membered aryl, i.e. phenyl. In a second embodiment Ar1 is a 6-membered heteroaryl, in particular containing one nitrogen atom (pyridyl) or two nitrogen atoms (pyridazinyl, pyrimidinyl or pyrazinyl).

In particular Ar1 is phenyl or 2-pyridyl, such as phenyl. The position numbering for Ar1 is in respect of the amide, with the carbon at the point of attachment designated position 1 and other numbers providing the relative location of the nitrogen atoms, for example:

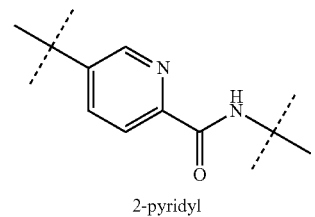

2-pyridyl

In one embodiment $R_{10}$ is H. In a second embodiment $R_{10}$ is halo, for example fluoro or chloro. In a third embodiment $R_{10}$ is $C_{1-3}$alkyl, i.e. $CH_3$, ethyl or propyl (e.g. n-propyl or iso-propyl). In a fourth embodiment $R_{10}$ is O$C_{1-2}$alkyl, such as $OCH_3$ or ethoxy. In a fifth embodiment, $R_{10}$ is $C_{1-2}$haloalkyl, such as $CF_3$ or $CH_2CF_3$. In a sixth embodiment $R_{10}$ is O$C_{1-2}$haloalkyl, such as $OCF_3$. In a seventh embodiment $R_{10}$ is CN.

Suitably $R_{10}$ is H, fluoro, $OCH_3$, $CH_3$ or $CF_3$, in particular H or fluoro, especially H.

Suitably $R_{10}$ is attached at the ortho position of Ar1 relative to the amide (i.e. proximal to the amide).

In one embodiment $R_{11}$ is H. In a second embodiment $R_{11}$ is F. In a third embodiment, $R_{11}$ is Cl. In a fourth embodiment $R_{11}$ is $CH_3$. In a fifth embodiment $R_{11}$ is $CH_2CH_3$. In a sixth embodiment $R_{11}$ is $OCH_3$. In a seventh embodiment $R_{11}$ is $CF_3$. In an eighth embodiment $R_{11}$ is $OCF_3$. In a ninth embodiment $R_{11}$ is CN.

In one embodiment, $R_{11}$ is in the ortho position relative to the amide. In another embodiment, $R_{11}$ is in the meta position relative to the amide.

In one embodiment Ar2 is a 6-membered aryl, i.e. phenyl. In a second embodiment Ar2 is a 6-membered heteroaryl, in particular containing one nitrogen atom (pyridyl) or two nitrogen atoms (pyridazinyl, pyrimidinyl or pyrazinyl).

The position numbering for Ar2 is in respect of the point of attachment to Ar1, for example:

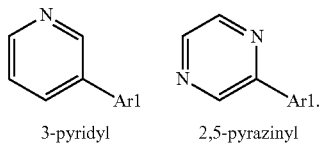

3-pyridyl    2,5-pyrazinyl

In particular Ar2 is 3-pyridyl or 2,5-pyrazinyl, especially 2,5-pyrazinyl.

In one embodiment $R_{12}$ is H. In a second embodiment $R_{12}$ is halo, for example fluoro or chloro. In a third embodiment $R_{12}$ is $C_{1-4}$alkyl, i.e. methyl, ethyl, propyl (n-propyl or isopropyl) or butyl (n-butyl, isobutyl, sec-butyl or tert-butyl). In a fourth embodiment, $R_{12}$ is $C_{2-4}$alkynyl such as $C_2$alkynyl (i.e. C≡CH). In a fifth embodiment, $R_{12}$ is C(=O)$C_{1-2}$alkyl, such as C(=O)$C_1$alkyl or C(=O)$C_2$alkyl. In a sixth embodiment $R_{12}$ is $OC_{0-2}$alkylene$C_{3-5}$cycloalkyl, such as $OC_{3-5}$cycloalkyl (e.g. cyclopropoxy or cyclobutoxy), $OC_1$alkylene$C_{3-5}$cycloalkyl or $OC_2$alkylene$C_{3-5}$cycloalkyl. In a seventh embodiment $R_{12}$ is $OC_{1-4}$alkyl, such as $OCH_3$, ethoxy, iso-propoxy or n-propoxy. In an eighth embodiment, $R_{12}$ is $C_{1-3}$alkyleneO$C_{1-3}$alkyl in particular $C_{1-2}$alkyleneO$C_{1-2}$alkyl such as $C_1$alkyleneO$C_1$alkyl, $C_2$alkyleneO$C_1$alkyl, $C_1$alkyleneO$C_2$alkyl or $C_2$alkyleneO$C_2$alkyl. In a ninth embodiment $R_{12}$ is $C_{1-4}$haloalkyl, such as $CF_3$. In a tenth embodiment $R_{12}$ is $OC_{1-4}$haloalkyl, such as $OCF_3$, $OCHF_2$ or $OCH_2CF_3$. In an eleventh embodiment $R_{12}$ is CN. In an eleventh embodiment $R_{12}$ is $OC_{0-2}$alkylene$C_{3-5}$cycloalkyl, such as $OC_{3-5}$cycloalkyl (e.g. cyclopropoxy or cyclobutoxy), $OC_1$alkylene$C_{3-5}$cycloalkyl or $OC_2$alkylene$C_{3-5}$cycloalkyl. In a twelfth embodiment $R_{12}$ is $OCH_2CH_2N(CH_3)_2$. In a thirteenth embodiment $R_{12}$ is OH. In a fourteenth embodiment $R_{12}$ is $C_{1-4}$alkylOH, such as $CH_2OH$ or $C(CH_3)_2OH$. In a fifteenth embodiment $R_{12}$ is $NR_{23}R_{24}$. In a sixteenth embodiment $R_{12}$ is $SO_2CH_3$. In a seventeenth embodiment $R_{12}$ is C(O)N$(CH_3)_2$. In an eighteenth embodiment $R_{12}$ is NHC(O)$C_{1-3}$alkyl such as NHC(O)$CH_3$. In a nineteenth embodiment $R_{12}$ is a $C_{3-6}$heterocycloalkyl comprising (such as containing) one nitrogen located at the point of attachment to Ar2, such as a $C_5$heterocycloalkyl, in particular pyrrolidinyl, or a $C_6$heterocycloalkyl such as morpholinyl. In a twentieth embodiment, $R_{12}$ together with a nitrogen atom to which it is attached forms an N-oxide ($N^+$—$O^-$).

In one embodiment, $R_{23}$ is H. In another embodiment, $R_{23}$ is $C_{1-2}$alkyl i.e. $CH_3$ or $CH_2CH_3$.

In one embodiment, $R_{24}$ is H. In another embodiment, $R_{24}$ is $C_{1-2}$alkyl i.e. $CH_3$ or $CH_2CH_3$.

$R_{12}$ is suitably H, fluoro, chloro, $CH_3$, Et, $OCH_3$, OEt, OiPr, $CF_3$ or $OCH_2CF_3$. In particular, $R_{12}$ is fluoro, chloro, $CH_3$, $OCH_3$, OEt, OiPr or $CF_3$, for example chloro, OEt, OiPr or $CF_3$ such as chloro, OEt or $CF_3$.

$R_{12}$ is suitably attached at the meta position of Ar2. Alternatively, $R_{12}$ is attached at the ortho position of Ar2.

The present invention provides N-oxides of the compound of formula (I). Suitably, when $R_{12}$ together with a nitrogen atom to which it is attached forms an N-oxide ($N^+$—$O^-$), the example following structures are formed:

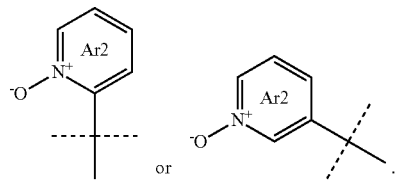

or

Throughout the specification Ar1 and Ar2 may be depicted as follows:

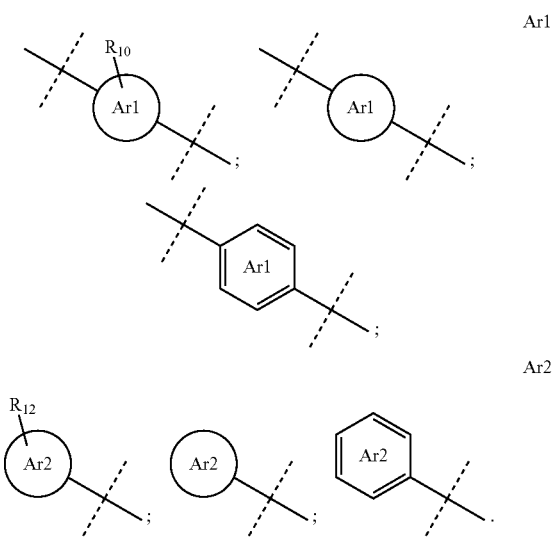

Ar1 may also be depicted as follows:

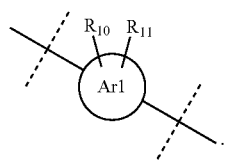

All depictions with respect to Ar1 are equivalent and all depictions with respect to Ar2 are equivalent, unless the context requires otherwise, depictions of Ar1 and Ar2 should not be taken to exclude the presence of heteroatoms or substitutions.

The present invention provides the compounds described in any one of Examples R1 to R71.

The present invention also provides the compounds described in any one of Examples R72 to R93.

The present invention provides the following compounds:

N-((2-(cyclopropanesulfonamido)thiazol-4-yl)methyl)-5-phenylpicolinamide;

N-((2-(cyclopropanesulfonamido)thiazol-4-yl)methyl)-4-(pyridin-3-yl)benzamide;

N-(1-(2-(cyclopropanesulfonamido)thiazol-4-yl)propyl)-4-(5-(trifluoromethyl)pyridin-3-yl)benzamide;

N-(1-(2-(cyclopropanesulfonamido)thiazol-4-yl)propyl)-4-(5-(trifluoromethyl)pyridin-3-yl)benzamide (R enantiomer);

N-(1-(2-(cyclopropanesulfonamido)thiazol-4-yl)propyl)-4-(5-(trifluoromethyl)pyridin-3-yl)benzamide (S enantiomer);

N-(1-(2-(cyclopropanesulfonamido)thiazol-4-yl)propyl)-4-(6-(trifluoromethyl)pyrazin-2-yl)benzamide;

N-(2-(2-(cyclopropanesulfonamido)thiazol-4-yl)propan-2-yl)-4-(6-ethoxypyrazin-2-yl)-2-fluorobenzamide;

N-(2-(2-(cyclopropanesulfonamido)thiazol-4-yl)propan-2-yl)-4-(6-ethoxypyrazin-2-yl)-2-methoxybenzamide;

N-((2-(cyclopropanesulfonamido)thiazol-4-yl)methyl)-[1,1'-biphenyl]-4-carboxamide;

N-((2-(cyclopropanesulfonamido)thiazol-4-yl)methyl)-2-fluoro-4-(6-(trifluoromethyl)pyrazin-2-yl)benzamide;

N-((2-(cyclopropanesulfonamido)thiazol-4-yl)methyl)-4-(6-ethoxypyrazin-2-yl)-2-fluorobenzamide;

N-((2-(cyclopropanesulfonamido)thiazol-4-yl)methyl)-4-(6-(trifluoromethyl)pyrazin-2-yl)benzamide;

N-((2-(cyclopropanesulfonamido)thiazol-4-yl)methyl)-4-(6-isopropoxypyrazin-2-yl)benzamide;

N-((2-(cyclopropanesulfonamido)thiazol-4-yl)methyl)-4-(6-ethoxypyrazin-2-yl)benzamide;

N-(3-(2-(cyclopropanesulfonamido)thiazol-4-yl)pentan-3-yl)-4-(5-(trifluoromethyl)pyridin-3-yl)benzamide;

N-(3-(2-(cyclopropanesulfonamido)thiazol-4-yl)pentan-3-yl)-4-(5-fluoropyridin-3-yl)benzamide;

N-(3-(2-(cyclopropanesulfonamido)thiazol-4-yl)pentan-3-yl)-4-(5-methylpyridin-3-yl)benzamide;

N-(3-(2-(cyclopropanesulfonamido)thiazol-4-yl)pentan-3-yl)-4-(pyridin-3-yl)benzamide;

N-(3-(2-(cyclopropanesulfonamido)thiazol-4-yl)pentan-3-yl)-4-(6-(trifluoromethyl)pyrazin-2-yl)benzamide;

4-(6-chloropyrazin-2-yl)-N-(3-(2-(cyclopropanesulfonamido)thiazol-4-yl)pentan-3-yl)benzamide;

N-(3-(2-(cyclopropanesulfonamido)thiazol-4-yl)pentan-3-yl)-4-(6-methylpyrazin-2-yl)benzamide;

N-(3-(2-(cyclopropanesulfonamido)thiazol-4-yl)pentan-3-yl)-4-(pyrazin-2-yl)benzamide;

N-(2-(2-(cyclopropanesulfonamido)thiazol-4-yl)propan-2-yl)-5-(6-ethoxypyrazin-2-yl)-3-fluoropicolinamide;

N-(2-(2-(cyclopropanesulfonamido)thiazol-4-yl)propan-2-yl)-5-(6-(trifluoromethyl)pyrazin-2-yl)picolinamide;

5-(6-chloropyrazin-2-yl)-N-(2-(2-(cyclopropanesulfonamido)thiazol-4-yl)propan-2-yl)picolinamide;

N-(2-(2-(cyclopropanesulfonamido)thiazol-4-yl)propan-2-yl)-5-(6-ethoxypyrazin-2-yl)picolinamide;

N-(2-(2-(cyclopropanesulfonamido)thiazol-4-yl)propan-2-yl)-[2,2'-bipyridine]-5-carboxamide;

4-(5-chloropyridin-3-yl)-N-(2-(2-(cyclopropanesulfonamido)thiazol-4-yl)propan-2-yl)benzamide;

N-(2-(2-(cyclopropanesulfonamido)thiazol-4-yl)propan-2-yl)-2-fluoro-4-(5-(trifluoromethyl)pyridin-3-yl)benzamide;

4-(5-chloropyridin-3-yl)-N-(2-(2-(cyclopropanesulfonamido)thiazol-4-yl)propan-2-yl)-2-fluorobenzamide;

N-(2-(2-(cyclopropanesulfonamido)thiazol-4-yl)propan-2-yl)-2-fluoro-4-(5-fluoropyridin-3-yl)benzamide;

N-(2-(2-(cyclopropanesulfonamido)thiazol-4-yl)propan-2-yl)-2-methoxy-4-(5-(trifluoromethyl)pyridin-3-yl)benzamide;

4-(5-acetylpyridin-3-yl)-N-(2-(2-(cyclopropanesulfonamido)thiazol-4-yl)propan-2-yl)benzamide;

N-(2-(2-(cyclopropanesulfonamido)thiazol-4-yl)propan-2-yl)-4-(5-(trifluoromethyl)pyridin-3-yl)benzamide;

N-(2-(2-(cyclopropanesulfonamido)thiazol-4-yl)propan-2-yl)-4-(5-fluoropyridin-3-yl)benzamide;

N-(2-(2-(cyclopropanesulfonamido)thiazol-4-yl)propan-2-yl)-4-(5-methylpyridin-3-yl)benzamide;

N-(2-(2-(cyclopropanesulfonamido)thiazol-4-yl)propan-2-yl)-4-(5-methoxypyridin-3-yl)benzamide;

N-(2-(2-(cyclopropanesulfonamido)thiazol-4-yl)propan-2-yl)-4-(pyridin-3-yl)benzamide;

N-(2-(2-(cyclopropanesulfonamido)thiazol-4-yl)propan-2-yl)-3'-(trifluoromethyl)-[1,1'-biphenyl]-4-carboxamide;

N-(2-(2-(cyclopropanesulfonamido)thiazol-4-yl)propan-2-yl)-4-(6-ethylpyrazin-2-yl)-2-fluorobenzamide;

N-(2-(2-(cyclopropanesulfonamido)thiazol-4-yl)propan-2-yl)-2-fluoro-4-(6-(trifluoromethyl)pyrazin-2-yl)benzamide;

N-(2-(2-(cyclopropanesulfonamido)thiazol-4-yl)propan-2-yl)-2-fluoro-4-(6-isopropoxypyrazin-2-yl)benzamide;

N-(2-(2-(cyclopropanesulfonamido)thiazol-4-yl)propan-2-yl)-2-fluoro-4-(6-(2,2,2-trifluoroethoxy)pyrazin-2-yl)benzamide;

N-(2-(2-(cyclopropanesulfonamido)thiazol-4-yl)propan-2-yl)-2-methyl-4-(6-(trifluoromethyl)pyrazin-2-yl)benzamide;

N-(2-(2-(cyclopropanesulfonamido)thiazol-4-yl)propan-2-yl)-4-(6-ethoxypyrazin-2-yl)-2-methylbenzamide;

N-(2-(2-(cyclopropanesulfonamido)thiazol-4-yl)propan-2-yl)-4-(6-ethoxypyrazin-2-yl)-2-(trifluoromethyl)benzamide;

N-(2-(2-(cyclopropanesulfonamido)thiazol-4-yl)propan-2-yl)-2-methoxy-4-(6-(trifluoromethyl)pyrazin-2-yl)benzamide;

4-(6-chloropyrazin-2-yl)-N-(2-(2-(cyclopropanesulfonamido)thiazol-4-yl)propan-2-yl)-2-methoxybenzamide;

4-(6-cyanopyrazin-2-yl)-N-(2-(2-(cyclopropanesulfonamido)thiazol-4-yl)propan-2-yl)-2-methoxybenzamide;

N-(2-(2-(cyclopropanesulfonamido)thiazol-4-yl)propan-2-yl)-4-(6-(trifluoromethyl)pyrazin-2-yl)benzamide;

4-(6-chloropyrazin-2-yl)-N-(2-(2-(cyclopropanesulfonamido)thiazol-4-yl)propan-2-yl)benzamide;

N-(2-(2-(cyclopropanesulfonamido)thiazol-4-yl)propan-2-yl)-4-(6-methylpyrazin-2-yl)benzamide;

N-(2-(2-(cyclopropanesulfonamido)thiazol-4-yl)propan-2-yl)-4-(6-methoxypyrazin-2-yl)benzamide;

N-(2-(2-(cyclopropanesulfonamido)thiazol-4-yl)propan-2-yl)-4-(6-ethoxypyrazin-2-yl)benzamide;

N-(2-(2-(cyclopropanesulfonamido)thiazol-4-yl)propan-2-yl)-4-(6-isopropoxypyrazin-2-yl)benzamide;

N-(2-(2-(cyclopropanesulfonamido)thiazol-4-yl)propan-2-yl)-4-(6-(2,2,2-trifluoroethoxy)pyrazin-2-yl)benzamide;

N-(2-(2-(cyclopropanesulfonamido)thiazol-4-yl)propan-2-yl)-4-(pyrazin-2-yl)benzamide;

N-(1-(2-(cyclopropanesulfonamido)thiazol-4-yl)propyl)-4-(5-fluoropyridin-3-yl)benzamide;

N-(1-(2-(cyclopropanesulfonamido)thiazol-4-yl)propyl)-4-(5-methylpyridin-3-yl)benzamide;

N-(1-(2-(cyclopropanesulfonamido)thiazol-4-yl)propyl)-4-(pyridin-3-yl)benzamide;

N-(1-(2-(cyclopropanesulfonamido)thiazol-4-yl)propyl)-4-(6-ethoxypyrazin-2-yl)-2-fluorobenzamide;

N-(1-(2-(cyclopropanesulfonamido)thiazol-4-yl)propyl)-4-(6-ethoxypyrazin-2-yl)-2-fluoro-N-methylbenzamide;
N-(1-(2-(cyclopropanesulfonamido)thiazol-4-yl)propyl)-2-fluoro-4-(6-isopropoxypyrazin-2-yl)benzamide;
4-(6-chloropyrazin-2-yl)-N-(1-(2-(cyclopropanesulfonamido)thiazol-4-yl)propyl)benzamide;
N-(1-(2-(cyclopropanesulfonamido)thiazol-4-yl)propyl)-4-(6-methylpyrazin-2-yl)benzamide;
N-(1-(2-(cyclopropanesulfonamido)thiazol-4-yl)propyl)-4-(pyrazin-2-yl)benzamide;
N-(1-(2-(cyclopropanesulfonamido)thiazol-4-yl)propyl)-4-(5-fluoropyridin-3-yl)benzamide (R enantiomer);
N-(1-(2-(cyclopropanesulfonamido)thiazol-4-yl)propyl)-4-(5-fluoropyridin-3-yl)benzamide (S enantiomer);
N-(1-(2-(cyclopropanesulfonamido)thiazol-4-yl)propyl)-4-(6-ethoxypyrazin-2-yl)-2-fluorobenzamide (R enantiomer); and
N-(1-(2-(cyclopropanesulfonamido)thiazol-4-yl)propyl)-4-(6-ethoxypyrazin-2-yl)-2-fluorobenzamide (S enantiomer);
or a salt and/or solvate thereof and/or derivative thereof.

The invention also provides the following compounds:
N-(2-(2-(cyclopropanesulfonamido)-5-methylthiazol-4-yl)propan-2-yl)-5-(6-ethoxypyrazin-2-yl)picolinamide;
N-(2-(5-chloro-2-(cyclopropanesulfonamido)thiazol-4-yl)propan-2-yl)-5-(6-ethoxypyrazin-2-yl)picolinamide;
N-(2-(2-(cyclopropanesulfonamido)-5-methylthiazol-4-yl)propan-2-yl)-4-(6-ethoxypyrazin-2-yl)-2-fluorobenzamide;
N-(2-(5-chloro-2-(cyclopropanesulfonamido)thiazol-4-yl)propan-2-yl)-4-(6-ethoxypyrazin-2-yl)-2-fluorobenzamide;
N-(2-(2-(cyclopropanesulfonamido)-5-methylthiazol-4-yl)propan-2-yl)-2-methyl-4-(6-(trifluoromethyl)pyrazin-2-yl)benzamide;
N-(2-(5-chloro-2-(cyclopropanesulfonamido)thiazol-4-yl)propan-2-yl)-2-methyl-4-(6-(trifluoromethyl)pyrazin-2-yl)benzamide;
N-(2-(2-(cyclopropanesulfonamido)-5-methylthiazol-4-yl)propan-2-yl)-4-(6-(trifluoromethyl)pyrazin-2-yl)benzamide;
N-(2-(5-chloro-2-(cyclopropanesulfonamido)thiazol-4-yl)propan-2-yl)-4-(6-(trifluoromethyl)pyrazin-2-yl)benzamide;
N-(1-(2-(cyclopropanesulfonamido)thiazol-4-yl)cyclopropyl)-5-(6-ethoxypyrazin-2-yl)picolinamide;
N-(1-(2-(cyclopropanesulfonamido)thiazol-4-yl)cyclopropyl)-4-(pyridin-3-yl)benzamide;
N-(1-(2-(cyclopropanesulfonamido)thiazol-4-yl)cyclopropyl)-4-(6-ethoxypyrazin-2-yl)-2-fluorobenzamide;
N-(1-(2-(cyclopropanesulfonamido)thiazol-4-yl)cyclopropyl)-2-methyl-4-(6-(trifluoromethyl)pyrazin-2-yl)benzamide;
N-(1-(2-(cyclopropanesulfonamido)thiazol-4-yl)cyclopropyl)-4-(6-(trifluoromethyl)pyrazin-2-yl)benzamide;
N-(1-(2-(cyclopropanesulfonamido)thiazol-4-yl)-3-methoxypropyl)-4-(5-fluoropyridin-3-yl)benzamide;
N-(1-(2-(cyclopropanesulfonamido)thiazol-4-yl)-3-methoxypropyl)-4-(6-ethylpyrazin-2-yl)-2-fluorobenzamide;
N-(1-(2-(cyclopropanesulfonamido)thiazol-4-yl)-3-methoxypropyl)-2-fluoro-4-(6-(trifluoromethyl)pyrazin-2-yl)benzamide;
N-(1-(2-(cyclopropanesulfonamido)thiazol-4-yl)-3-methoxypropyl)-4-(6-ethoxypyrazin-2-yl)-2-fluorobenzamide;
N-(1-(2-(cyclopropanesulfonamido)thiazol-4-yl)-3-methoxypropyl)-2-fluoro-4-(6-isopropoxypyrazin-2-yl)benzamide;
N-(1-(2-(cyclopropanesulfonamido)thiazol-4-yl)-3-methoxypropyl)-4-(6-ethoxypyrazin-2-yl)benzamide;
N-(1-(2-(cyclopropanesulfonamido)thiazol-4-yl)ethyl)-4-(6-ethoxypyrazin-2-yl)-2-fluorobenzamide;
N-(1-(2-(cyclopropanesulfonamido)thiazol-4-yl)-3-methoxypropyl)-4-(6-ethoxypyrazin-2-yl)-2-fluorobenzamide (R enantiomer); and
N-(1-(2-(cyclopropanesulfonamido)thiazol-4-yl)-3-methoxypropyl)-4-(6-ethoxypyrazin-2-yl)-2-fluorobenzamide (S enantiomer);
or a salt and/or solvate thereof and/or derivative thereof.

The compounds of the invention may be provided in the form of a pharmaceutically acceptable salt and/or solvate thereof and/or derivative thereof. In particular, the compound of formula (I) may be provided in the form of a pharmaceutically acceptable salt and/or solvate, such as a pharmaceutically acceptable salt.

Compounds of the invention of particular interest are those demonstrating an $IC_{50}$ of 1 uM or lower, especially 100 nM or lower, in respect of CTPS1 enzyme, using the methods of the examples (or comparable methods).

Compounds of the invention of particular interest are those demonstrating a selectivity for CTPS1 over CTPS2 of 2-30 fold, suitably >30-60 fold or more suitably >60 fold, using the methods of the examples (or comparable methods).

It will be appreciated that for use in medicine the salts of the compounds of formula (I) should be pharmaceutically acceptable. Non-pharmaceutically acceptable salts of the compounds of formula (I) may be of use in other contexts such as during preparation of the compounds of formula (I). Suitable pharmaceutically acceptable salts will be apparent to those skilled in the art. Pharmaceutically acceptable salts include those described by Berge et al. (1977). Such pharmaceutically acceptable salts include acid and base addition salts. Pharmaceutically acceptable acid additional salts may be formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain compounds of formula (I) form acid or base addition salts with one or more equivalents of the acid or base. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) and that these are included within the scope of the invention.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exist as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

In one embodiment, the compounds of the invention are provided in a natural isotopic form.

In one embodiment, the compounds of the invention are provided in an unnatural variant isotopic form. In a specific embodiment, the unnatural variant isotopic form is a form in which deuterium (i.e. $^2$H or D) is incorporated where hydrogen is specified in the chemical structure in one or more atoms of a compound of the invention. In one embodiment, the atoms of the compounds of the invention are in an isotopic form which is not radioactive. In one embodiment, one or more atoms of the compounds of the invention are in an isotopic form which is radioactive. Suitably radioactive isotopes are stable isotopes. Suitably the unnatural variant isotopic form is a pharmaceutically acceptable form.

In one embodiment, a compound of the invention is provided whereby a single atom of the compound exists in an unnatural variant isotopic form. In another embodiment, a compound of the invention is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof.

General Routes

Generic routes by which compound examples of the invention may be conveniently prepared are summarised below.

Scheme 1: Synthesis of dialkyl amides of formula (I)

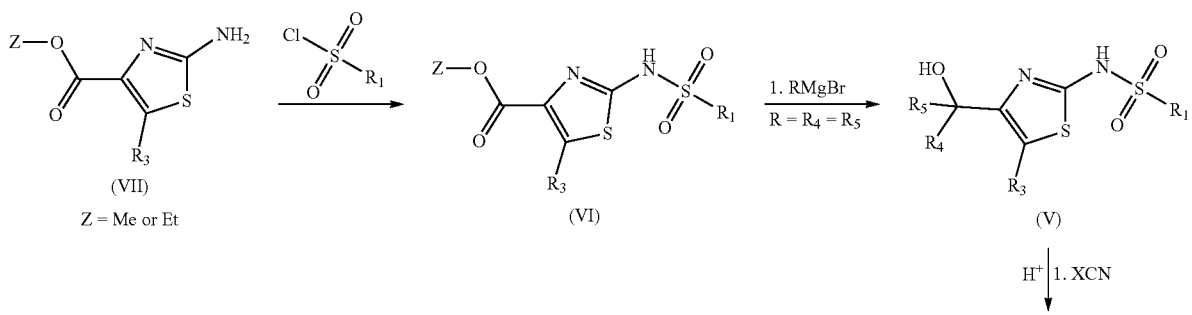

(VII) Z = Me or Et (VI)

(V)

$H^+$ | 1. XCN

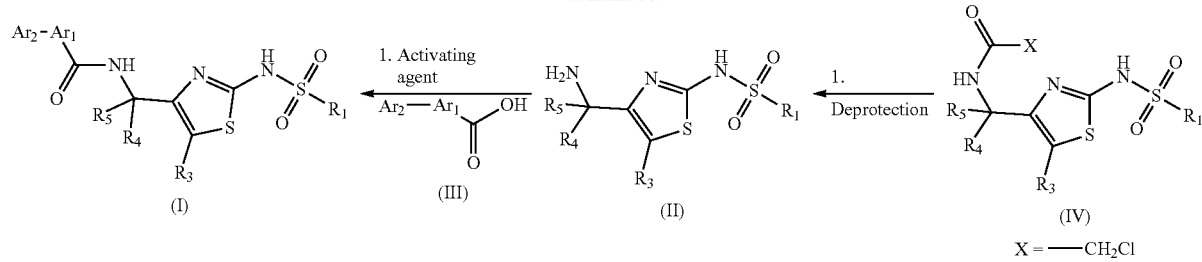

The thiazol-4-yl(propan-2-yl)benzamide derivatives of formula (I) in which $R_1$, $R_3$, $R_4$, $R_5$, $Ar_1$ and $Ar_2$ are defined above may be prepared as shown in Scheme 1 by sulfonation of the commercial amine such as (VII) followed by double Grignard addition to ethyl 2-(cyclopropanesulfonamido)thiazole-4-carboxylate (VI) in an aprotic solvent such as THF to form intermediates of formula (V). A Ritter type reaction may then be undertaken using an alkylnitrile, such as 2-chloroacetonitrile in the presence of an acid such as $H_2SO_4$. This intermediate of formula (IV) can be deprotected by reaction with thiourea in a protic solvent such as ethanol in the presence of acetic acid and heated under reflux to yield the free benzylamine derivative (II). A carboxylic acid precursor (III) (commercially available or prepared in two steps, as in Scheme 4) is reacted with an activating agent such as HATU, T3P or Ghosez's reagent (1-chloro-N,N,2-trimethylprop-1-en-1-amine), to generate a reactive, electrophilic carboxylic acid derivative, followed by subsequent reaction with benzylamine of formula (II), to yield the desired amide derivative of general formula (I).

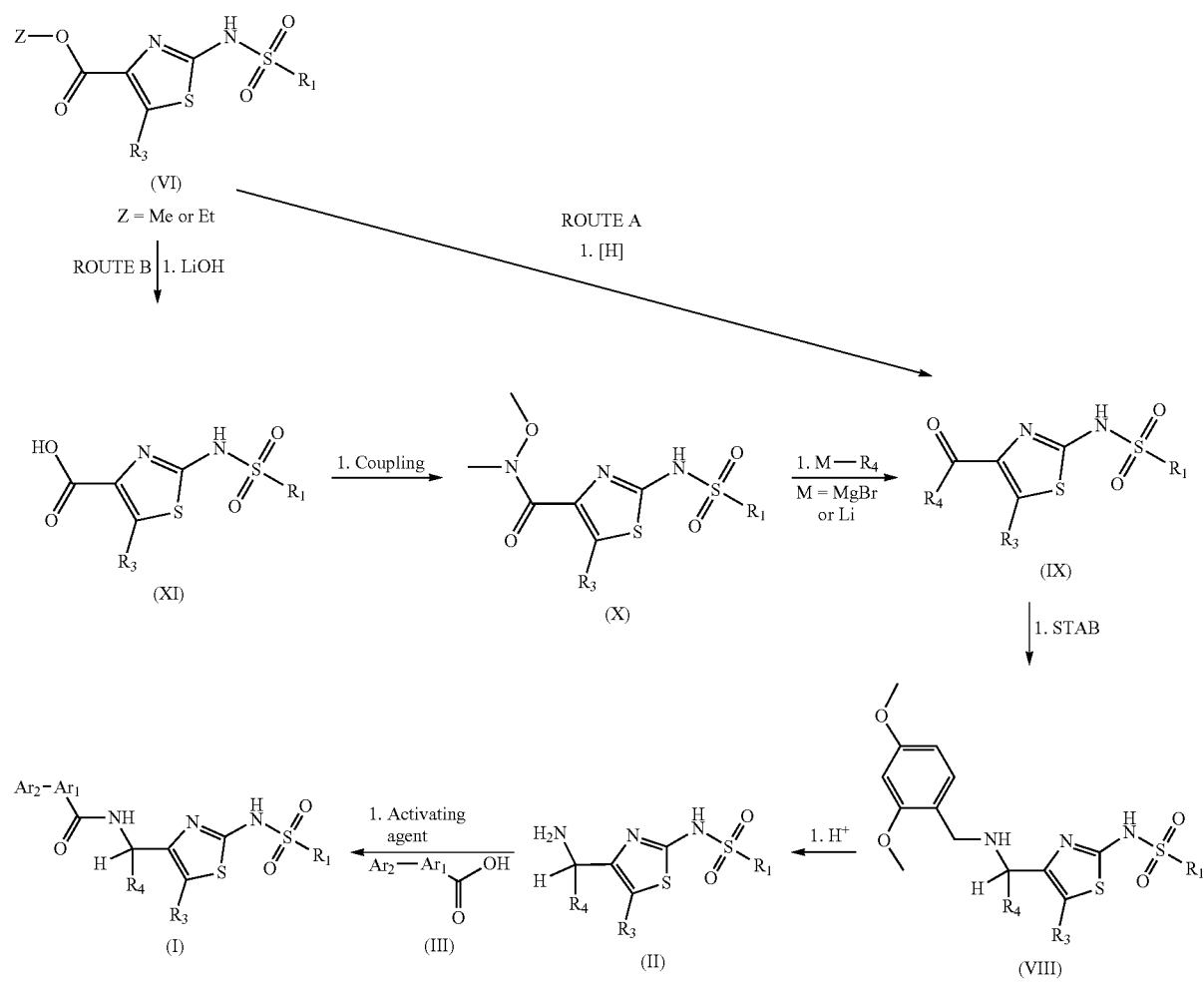

Scheme 2: Synthesis of des ($R_4$ and $R_5$ are H) and monosubstituted ($R_5$ is H) amides of formula (I)

The thiazol-4-yl(propan-2-yl)benzamide derivatives of formula (I) in which $R_1$, $R_3$, $R_4$, $Ar_1$ and $Ar_2$ are defined above may be prepared by two different routes as shown in Scheme 2. The two routes then converge at compounds of general formula (IX) where they are then taken on to the final analogues by a two-step process.

ROUTE A: Reduction of the ester of general formula (VI) using a reducing agent such as DIBAL-H yields the aldehyde of general formula (IX) ($R_4$ is H). It will be understood by persons skilled in the art that such reactions need to be carefully controlled to avoid over-reduction.

ROUTE B: The alkyl ester of formula (VI) may be conveniently hydrolysed by exposure to a suitable inorganic base, for example lithium hydroxide, in an aqueous mixture of aprotic and protic solvents, such as THF:methanol:water. The carboxylic acid derivative (XI) can then be converted to the Weinreb amide by employing a coupling agent, for example, HATU in the presence of a suitable base, such as DIPEA in a solvent such as DMF. The Weinreb amide derivative (X) can then be exposed to a nucleophile such as EtMgBr in an aprotic solvent such as THE to yield the corresponding ketone of the general formula (IX).

A reductive amination may be undertaken using (2,4-dimethoxyphenyl)methanamine and a reducing agent such as sodium triacetoxyborohydride (STAB). This reaction can be carried out on the ketone of general formula (IX) (when $R_4$ is other than H) or the aldehyde of general formula (IX) (when $R_4$ is H), if the des-alkyl linker is desired. The intermediate of formula (VIII) may then be deprotected using a strong acid, such as TFA. Such reactions may be heated to 70° C. to yield the free benzylamine derivative (II). An amide coupling can then be undertaken as in Scheme 1.

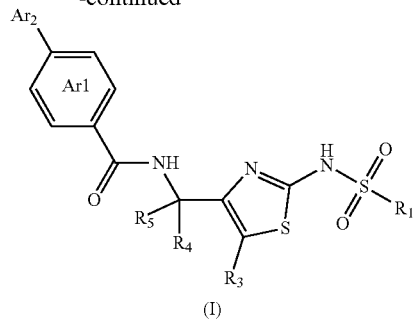

(I)

Compounds of formula (XIII) may be obtained by a general process as shown in Scheme 3 whereby a carboxylic acid precursor (XIV) is reacted with an activating agent such as HATU, T3P or Ghosez's reagent, to generate a reactive, electrophilic carboxylic acid derivative, followed by subsequent reaction with an amine of formula (II). Intermediates of formula (XIII) are then converted to a compound of general formula (I) by coupling under Suzuki conditions with an aromatic halide of general formula (XII), of which X is defined in Scheme 3 and represents a dihydroxyboryl or dialkyloxyboryl group, such as a 4,4,5,5-tetramethyl-1,3,3,2-dioxaborolan-2-yl group. The couplings according to the Suzuki method are performed, for example, by heating in the presence of a catalyst such as bis(diphenylphosphino)ferrocene]dichloropalladium(II)·$CH_2Cl_2$ adduct and an inorganic base such as potassium carbonate in a solvent mixture of dioxane and water under an inert atmosphere such as a nitrogen atmosphere. It will be understood by persons skilled in the art that many catalysts and conditions can be employed for such couplings.

Scheme 3: Synthesis of compounds of formula (I) via Suzuki coupling

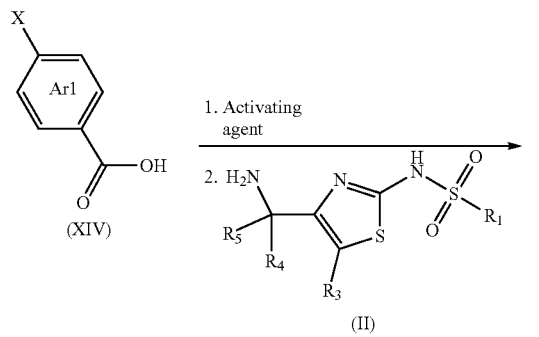

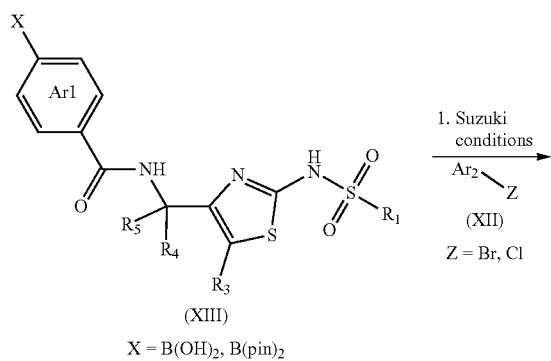

Scheme 4: Synthesis of carbolylic derivative (III)

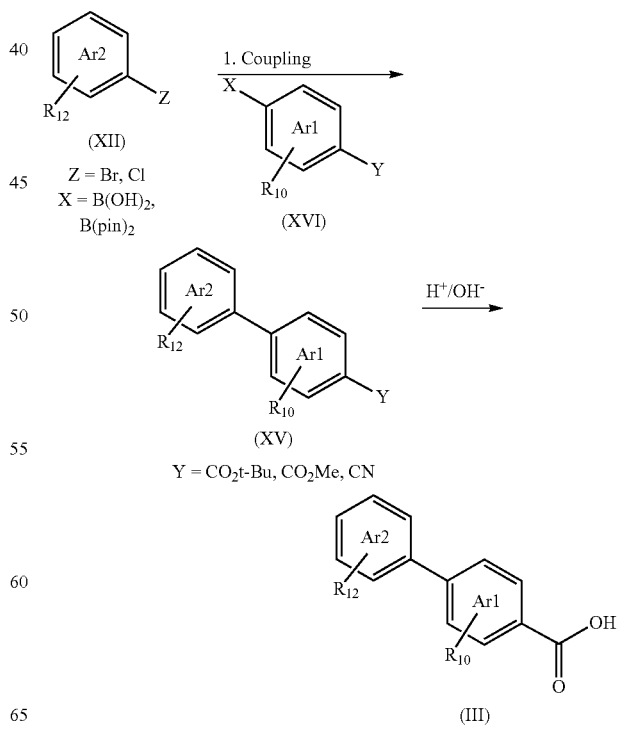

Intermediates of formula (III) where $Ar_2$ is an unsubstituted or substituted 2-pyrazine ring or 3-pyridyl ring, may be synthesised as shown in Scheme 4 by coupling under Suzuki conditions of an aromatic halide of general formula (XII), of which $R_{10}$ and $R_{12}$ are defined above and Z represents a halide such as Br or Cl, to a boronate of general formula (XVI) where X denotes a dihydroxyboryl or dialkyloxyboryl group, such as a 4,4,5,5-tetramethyl-1,3,3,2-dioxaborolan-2-yl group. The couplings according to the Suzuki method are performed, for example, by heating in the presence of a catalyst such as [1,1'-bis(diphenylphosphino)ferrocene]di- chloropalladium(II)·$CH_2Cl_2$ adduct and an inorganic base such as cesium carbonate in a solvent mixture of dioxane and water under an inert atmosphere such as a nitrogen atmosphere. The carboxylic acids of general formula (III) are obtained by either deprotection of the t-butyl ester using a strong acid, such as TFA in a solvent of $CH_2Cl_2$, hydrolysis of the methyl ester using an alkali metal hydroxide such as NaOH in a solvent mixture such as THF/MeOH or hydrolysis of the nitrile using a strong acid such as concentrated HCl. Compounds of formula (III-A) may also be made using this method.

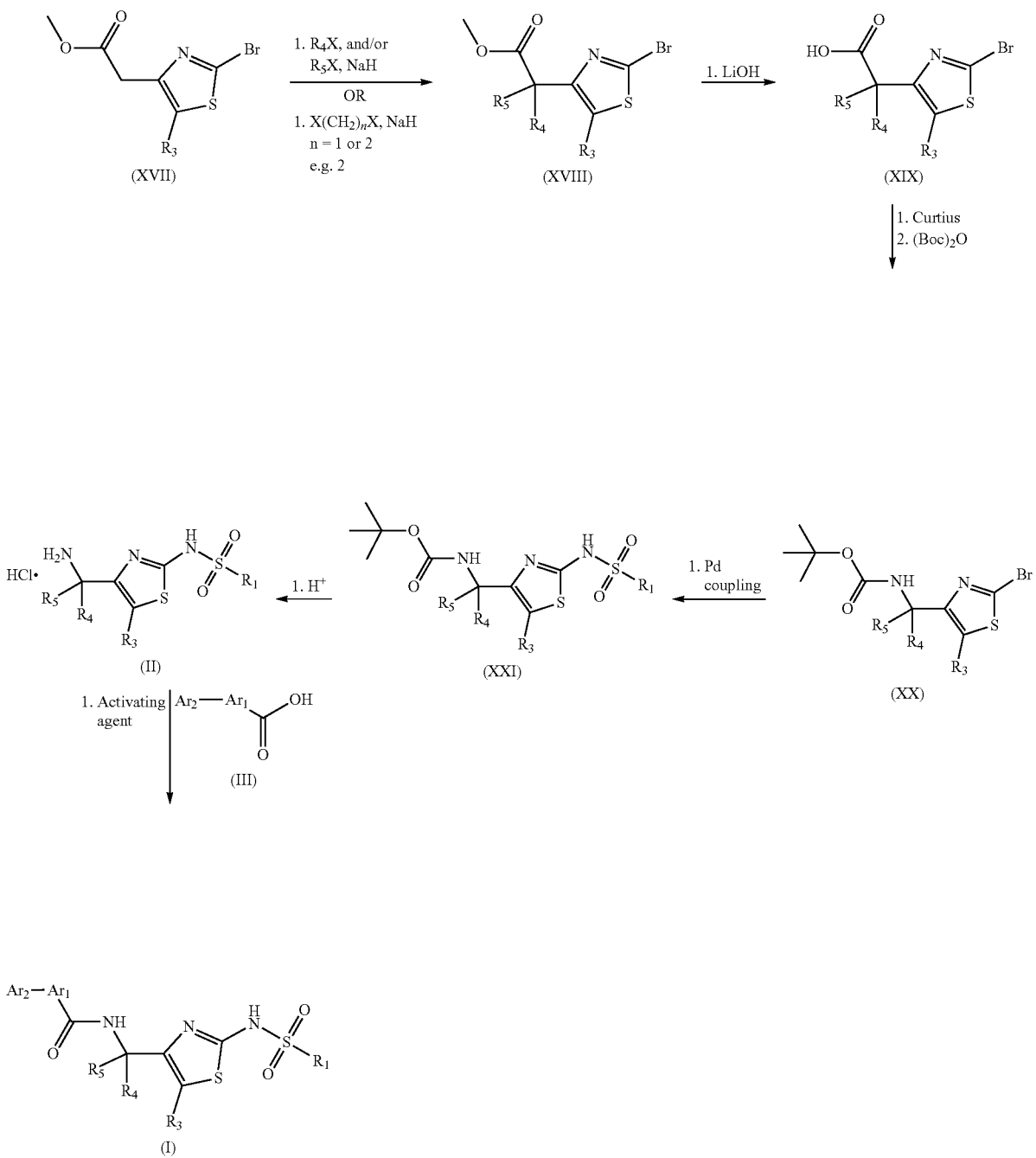

Scheme 5: Alternative Synthesis of amides of formula (I)

The thiazol-4-yl(propan-2-yl)benzamide derivatives of formula (I) in which $R_1$, $R_3$, $R_4$, $R_5$, $Ar_1$ and $Ar_2$ are defined above may be prepared by the route as shown in Scheme 5. Intermediate 2-bromthiazole esters of general formula (XVII) can be mono or bis-alkylated by alkyl halides such as 1-bromo-2-methoxyethane in the presence of a strong base such as sodium hydride to yield esters of general formula (XVIII) which may be conveniently hydrolysed by exposure to a suitable inorganic base, for example lithium hydroxide, in an aqueous mixture of aprotic and protic solvents, such as THF:methanol:water. The intermediate acyl azide, which may be formed from carboxylate (XIX) and diphenylphosphoryl azide in toluene and tert-butanol in the presence of a weak base such as trimethylamine undergoes a Curtius rearrangement at elevated temperatures such as 100° C. to yield an isocyanate that reacts with the alcohol present to give the carbamate protected amines of formula (XX). Palladium catalysed sulfonamidation of intermediate (XX) may be achieved using a catalytic system such as [Pd(allyl)Cl]$_2$ and a phosphine mono-dentate ligand such as t-BuXPhos in the presence of a primary sulphonamide to obtain compounds of the formula (XXI).

The intermediate of formula (XXI) may then be deprotected using a strong acid, such as HCl to yield the free benzylamine derivatives of formula (II) or salts thereof such as HCl salts. An amide coupling can then be undertaken as in Scheme 1 to give compounds of formula (I).

Intermediates of the Invention

The present invention also relates to novel intermediates in the synthesis of compounds of formula (I) such as compounds of formula (II)-(XXI) such as (II)-(XVI). Particular intermediates of interest are those of the following general formulae, wherein the variable groups and associated preferences are as defined previously for compounds of formula (I):

a compound of formula (II):

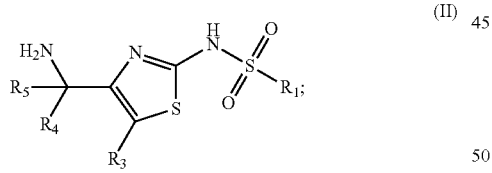

a compound of formula (III):

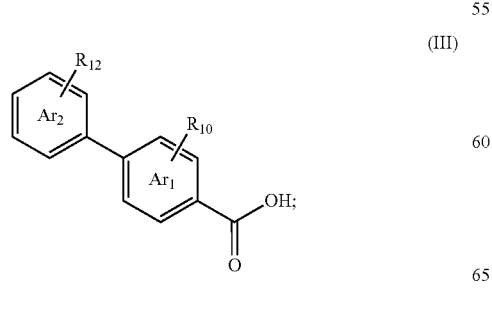

and a compound of formula (VIII):

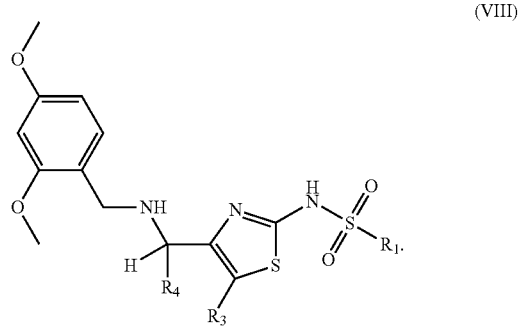

Also of interest are compounds of formula (III-A):

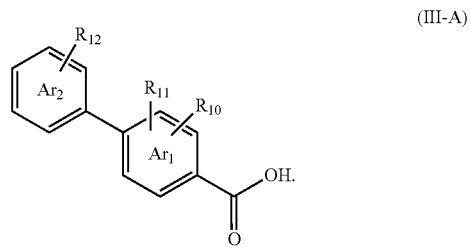

Suitably, the intermediate is not:

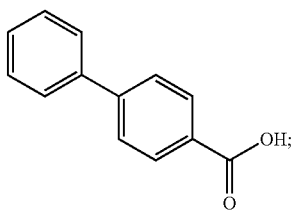

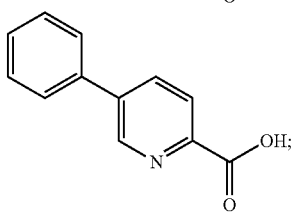

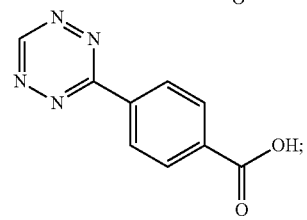

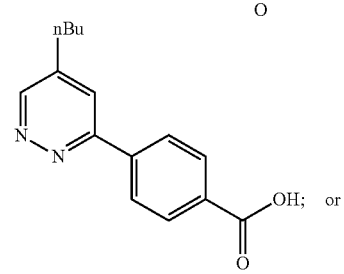

-continued

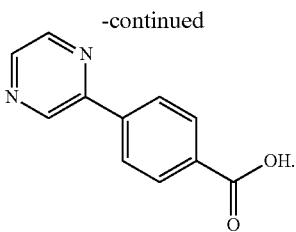

Suitably, at least one of $R_{10}$, $R_{11}$ and $R_{12}$ is other than H.

Included as an aspect of the invention are all novel intermediates described in the examples, including:
Intermediates INTE1 to INTE20; and
Intermediates INTF1 to INTF53.

Also included as an aspect of the invention are all novel intermediates described in the examples, including:
Intermediates INTE21 to INTE39.

Included as an aspect of the invention are salts such as pharmaceutically acceptable salts of any one of the intermediates disclosed herein, such as any one of compounds of formulae (II)-(XXI).

Therapeutic Methods

Compounds of formula (I) of the present invention have utility as inhibitors of CTPS1.

Suitably, the compounds of formula (I) of the present invention are selective for CTPS1 over CTPS2.

Therefore, the invention also provides a compound of formula (I), or a pharmaceutically acceptable salt and/or solvate (e.g. salt) and/or derivative thereof, for use as a medicament, in particular in the treatment or prophylaxis of a disease or disorder wherein an inhibitor of CTPS1 is beneficial, for example those diseases and disorders mentioned herein below.

The invention provides a method for the treatment or prophylaxis of a disease or disorder wherein an inhibitor of CTPS1 is beneficial, for example those diseases and disorders mentioned herein below, which comprises administering to a subject in need thereof an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the treatment or prophylaxis of a disease or disorder wherein an inhibitor of CTPS1 is beneficial, for example those diseases and disorders mentioned herein below.

More suitably, the disease or disorder wherein an inhibitor of CTPS1 is beneficial is a disease or disorder wherein a reduction in T-cell and/or B-cell proliferation would be beneficial.

The invention also provides a compound of formula (I), or a pharmaceutically acceptable salt and/or solvate (e.g. salt) and/or derivative thereof, for use in the inhibition of CTPS1 in a subject.

The invention provides a method for the inhibition of CTPS1 in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the inhibition of CTPS1 in a subject.

The invention also provides a compound of formula (I), or a pharmaceutically acceptable salt and/or solvate (e.g. salt) and/or derivative thereof, for use in the reduction of T-cell and/or B-cell proliferation in a subject.

The invention provides a method for the reduction of T-cell and/or B-cell proliferation in a subject, which comprises administering to the subject an effective amount of a compound of formula (I) or a pharmaceutically acceptable salt and/or solvate (e.g. salt) and/or derivative thereof.

The invention also provides the use of a compound of formula (I), or a pharmaceutically acceptable salt and/or solvate thereof (e.g. salt) and/or derivative, in the manufacture of a medicament for the reduction of T-cell and/or B-cell proliferation in a subject.

More suitably, the disease or disorder wherein an inhibitor of CTPS1 is beneficial is a disease or disorder wherein a reduction in T-cell and/or B-cell proliferation would be beneficial.

The term 'treatment' or 'treating' as used herein includes the control, mitigation, reduction, or modulation of the disease state or its symptoms.

The term 'prophylaxis' or 'preventing' is used herein to mean preventing symptoms of a disease or disorder in a subject or preventing recurrence of symptoms of a disease or disorder in an afflicted subject and is not limited to complete prevention of an affliction.

Suitably, the disease or disorder is selected from rejection of transplanted cells and tissues, Graft-related diseases or disorders, allergies and autoimmune diseases.

In one embodiment the disease or disorder is the rejection of transplanted cells and tissues. The subject may have been transplanted with a graft selected from the group consisting of heart, kidney, lung, liver, pancreas, pancreatic islets, brain tissue, stomach, large intestine, small intestine, cornea, skin, trachea, bone, bone marrow (or any other source of hematopoietic precursor cells and stem cells including hematopoietic cells mobilized from bone marrow into peripheral blood or umbilical cord blood cells), muscle, or bladder. The compounds of the invention may be of use in preventing or suppressing an immune response associated with rejection of a donor tissue, cell, graft or organ transplant in a subject.

In a further embodiment the disease or disorder is a Graft-related disease or disorder. Graft-related diseases or disorders include graft versus host disease (GVHD), such as GVHD associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc, and Host-Versus-Graft-Disease (HVGD). The compounds of the invention may be of use in preventing or suppressing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes). Thus the compounds of the invention have utility in preventing Host-Versus-Graft-Disease (HVGD) and Graft-Versus-Host-Disease (GVHD).

A CTPS1 inhibitor may be administered to the subject before, after transplantation and/or during transplantation. In some embodiments, the CTPS1 inhibitor may be administered to the subject on a periodic basis before and/or after transplantation.

In another embodiment, the disease or disorder is an allergy.

In additional embodiments the immune related disease or disorder is an autoimmune disease. As used herein, an "autoimmune disease" is a disease or disorder directed at a subject's own tissues. Examples of autoimmune diseases include, but are not limited to Addison's Disease, Adult-onset Still's disease, Alopecia Areata, Alzheimer's disease, Anti-neutrophil Cytoplasmic Antibodies (ANCA)-Associated Vasculitis, Ankylosing Spondylitis, Anti-phospholipid Syndrome (Hughes' Syndrome), Aplastic Anemia, Arthritis, Asthma, Atherosclerosis, Atherosclerotic plaque, Atopic Dermatitis, Autoimmune Hemolytic Anemia, Autoimmune Hepatitis, Autoimmune Hypophysitis (Lymphocytic Hypophysitis), Autoimmune Inner Ear Disease, Autoimmune Lymphoproliferative Syndrome, Autoimmune Myocarditis, Autoimmune Neutropenia, Autoimmune Oophoritis, Autoimmune Orchitis, Auto-Inflammatory Diseases requiring an immunosuppressive treatment, Azoospermia, Bechet's Disease, Berger's Disease, Bullous Pemphigoid, Cardiomyopathy, Cardiovascular disease, Celiac disease including Refractory Celiac Disease (type I and type II), Chronic Fatigue Immune Dysfunction Syndrome (CFIDS), Chronic Idiopathic Polyneuritis, Chronic Inflammatory Demyelinating Polyneuropathy (CIPD), Chronic Relapsing Polyneuropathy (Guillain-Barre syndrome), Churg-Strauss Syndrome (CSS), Cicatricial Pemphigoid, Cold Agglutinin Disease (CAD), chronic obstructive pulmonary disease (COPD), CREST Syndrome, Cryoglobulin Syndromes, Cutaneous Lupus, Dermatitis Herpetiformis, Dermatomyositis, Eczema, Epidermolysis Bullosa Acquisita, Essential Mixed Cryoglobulinemia, Evan's Syndrome, Exophthalmos, Fibromyalgia, Goodpasture's Syndrome, Grave's disease, Hemophagocytic Lymphohistiocytosis (HLH) (including Type 1 Hemophagocytic Lymphohistiocytosis), Histiocytosis/Histiocytic Disorders, Hashimoto's Thyroiditis, Idiopathic Pulmonary Fibrosis, Idiopathic Thrombocytopenia Purpura (ITP), IgA Nephropathy, Immunoproliferative Diseases or Disorders, Inflammatory Bowel Disease (IBD), Interstitial Lung Disease, Juvenile Arthritis, Juvenile Idiopathic Arthritis (JIA), Kawasaki's Disease, Lambert-Eaton Myasthenic Syndrome, Lichen Planus, Localized Scleroderma, Lupus Nephritis, Ménière's Disease, Microangiopathic Hemoytic Anemia, Microscopic Polyangitis, Miller Fischer Syndrome/Acute Disseminated Encephalomyeloradiculopathy, Mixed Connective Tissue Disease, Multiple Sclerosis (MS), Muscular Rheumatism, Myalgic Encephalomyelitis (ME), Myasthenia Gravis, Ocular Inflammation, *Pemphigus Foliaceus, Pemphigus Vulgaris*, Pernicious Anemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune Cholangiopathy, Primary Glomerulonephritis, Primary Sclerosing Cholangitis, Psoriasis, Psoriatic Arthritis, Pure Red Cell Anemia, Raynaud's Phenomenon, Reiter's Syndrome/Reactive Arthritis, Relapsing Polychondritis, Restenosis, Rheumatic Fever, Rheumatic Disease, Rheumatoid Arthritis, Sarcoidosis, Schmidt's Syndrome, Scleroderma/Systemic Sclerosis, Sjörgen's Syndrome, Stiff-Man Syndrome, The Sweet Syndrome (Febrile Neutrophilic Dermatosis), Systemic Lupus Erythematosus (SLE), Systemic Scleroderma, Takayasu Arteritis, Temporal Arteritis/Giant Cell Arteritis, Thyroiditis, Type 1 diabetes, Type 2 diabetes, Uveitis, Vasculitis, Vitiligo, Wegener's Granulomatosis, and X-linked lymphoproliferative disease.

Of particular interest are diseases and disorders which are mainly driven by T-cell activation and proliferation, including:

diseases and disorders which are not linked to alloreactivity including:
Alopecia areata, atopic dermatitis, eczema, psoriasis, lichen planus, psoriatic arthritis, vitiligo;
Uveitis;
Ankylosing spondylitis, Reiter's syndrome/reactive arthritis;
Aplastic anemia, autoimmune lymphoproliferative syndrome/disorders, hemophagocytic lymphohistiocytosis;
Type 1 diabetes; and
Refractory celiac disease;
Acute rejection of grafted tissues and transplanted organs; acute graft versus host disease (GVHD) after transplantation of bone marrow cells or any other source of allogenic cells including hematopoietic precursors cells and/or stem cells.

Also of interest are diseases and disorders which are driven by both T- and B-cell activation and proliferation, with an important involvement of B-cells, including:

diseases and disorders for which the involvement of pathogenic auto-antibodies is well characterized, including:
Allergy;
Cicatricial pemphigoid, bullous pemphigoid, epidermolysis bullosa acquisita, *pemphigus foliaceus, pemphigus vulgaris*, dermatitis herpetiformis;
ANCA-associated vasculitis and microscopic polyangitis, vasculitis, Wegener's granulomatosis; Churg-Strauss syndrome (CSS), polyarteritis nodosa, cryoglobulin syndromes and essential mixed cryglobulinemia;
Systemic lupus erythematosus (SLE), antiphospholipid syndrome (Hughes' syndrome), cutaneous lupus, lupus nephritis, mixed connective tissue disease;
Thyroiditis, Hashimoto thyroiditis, Grave's disease, exophthalmos;
Autoimmune hemolytic anemia, autoimmune neutropenia, ITP, pernicious anaemia, pure red cell anaemia, micro-angiopathic hemolytic anemia;
Primary glomerulonephritis, Berger's disease, Goodpasture's syndrome, IgA nephropathy; and
Chronic idiopathic polyneuritis, chronic inflammatory demyelinating polyneuropathy (CIPD), chronic relapsing polyneuropathy (Guillain-Barre syndrome), Miller Fischer syndrome, Stiff man syndrome, Lambert-Eaton myasthenic syndrome, myasthenia gravis.

diseases and disorders for which the involvement of B-cells is less clearly characterized (although sometimes illustrated by the efficacy of anti-CD20 monoclonal antibodies or intravenous immunoglobulin infusions) and may not correspond or be limited to the production of pathogenic antibodies (nevertheless, non-pathogenic antibodies are sometimes described or even often present and used as a diagnosis biomarker), including:
Addison's disease, autoimmune oophoritis and azoospermia, polyglandular syndromes (Whitaker's syndrome), Schmidt's syndrome;
Autoimmune myocarditis, cardiomyopathy, Kawasaki's disease;
Rheumatoid arthritis, Sjögren's syndrome, mixed connective tissue disease, polymyositis and dermatomyositis; polychondritis;
Primary glomerulonephritis;
Multiple sclerosis;

Autoimmune hepatitis, primary biliary cirrhosis/autoimmune cholangiopathy,

Hyper acute rejection of transplanted organs;

Chronic rejection of graft or transplants;

Chronic Graft versus Host reaction/disease after transplantation of bone marrow cells or hematopoietic precursor cells.

Additionally of interest are diseases and disorders for which the mechanism is shared between activation/proliferation of T-cells and activation/proliferation of innate immune cells and other inflammatory cellular subpopulations (including myeloid cells such as macrophages or granulocytes) and resident cells (such as fibroblasts and endothelial cells), including:

COPD, idiopathic pulmonary fibrosis, interstitial lung disease, sarcoidosis;

Adult onset Still's disease, juvenile idiopathic arthritis, Systemic sclerosis, CREST syndrome where B cells and pathogen antibodies may also play a role; the Sweet syndrome; Takayasu arteritis, temporal arteritis/giant cell arteritis;

Ulcerative cholangitis, inflammatory bowel disease (IBD) including Crohn's disease and ulcerative colitis, primary sclerosing cholangitis.

Also of interest are diseases and disorders for which the mechanism remains poorly characterized but involves the activation and proliferation of T-cells, including:

Alzheimer's disease, cardiovascular syndrome, type 2 diabetes, restenosis, chronic fatigue immune dysfuntion syndrome (CFIDS).

Autoimmune Lymphoproliferative disorders, including:

Autoimmune Lymphoproliferative Syndrome and X-linked lymphoproliferative disease.

Suitably the disease or disorder is selected from: inflammatory skin diseases such as psoriasis or lichen planus; acute and/or chronic GVHD such as steroid resistant acute GVHD; acute lymphoproliferative syndrome; systemic lupus erythematosus, lupus nephritis or cutaneous lupus; or transplantation. In addition, the disease or disorder may be selected from myasthenia gravis, multiple sclerosis, and scleroderma/systemic sclerosis.

The compounds of formula (I) may be used in the treatment of cancer.

Thus, in one embodiment there is provided is a compound of formula (I), or a pharmaceutically acceptable salt and/or solvate thereof and/or derivative thereof, for use in the treatment of cancer.

Further, there is provided a method for treating cancer in a subject, by administering to a subject in need thereof a compound of formula (I) or a pharmaceutically acceptable salt and/or solvate thereof and/or derivative thereof.

Additionally provided is the use of a compound of formula (I), or a pharmaceutically acceptable salt and/or solvate thereof and/or derivative thereof, in the manufacture of a medicament for the treatment of cancer in a subject.

Suitably the cancer is a haematological cancer, such as Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) or chronic lymphocytic leukemia.

Alternatively, the cancer is a non-haematological cancer, such as selected from the group consisting of bladder cancer, breast cancer, melanoma, neuroblastoma, malignant pleural mesothelioma and sarcoma, such as breast cancer and melanoma.

In addition, compounds of formula (I) may be used in enhancing recovery from vascular injury or surgery and reducing morbidity and mortality associated with neointima and restenosis in a subject. Vascular injury may occur in any vessel in the subject, such as a coronary artery, a renal artery, a carotid artery, a dialysis fistulae artery or a peripheral artery.

The compounds of formula (I) may be used in preventing, reducing, or inhibiting neointima formation. The compounds of formula (I) may be used in preventing or reducing the occurrence of restenosis, for example following surgery.

Furthermore, the compounds of formula (I) may be used in conjunction with a medical device. A medical device may be treated prior to insertion or implantation with an effective amount of a compound of formula (I) or a composition comprising a compound of formula (I) in order to prevent, reduce, or inhibit neointima formation following insertion or implantation of the device or graft into the subject. The device can be a device that is inserted into the subject transiently, or a device that is implanted permanently. In some embodiments, the device is a surgical device. Examples of medical devices include, but are not limited to, needles, cannulas, catheters, shunts, balloons, and implants such as stents and valves.

Suitably, the compound of formula (I) may be used in conjunction with angioplasty. The medical device may be a balloon.

Suitably the subject is a mammal, in particular the subject is a human.

Pharmaceutical Compositions

For use in therapy the compounds of the invention are usually administered as a pharmaceutical composition. The invention also provides a pharmaceutical composition comprising a compound of formula (I), or a pharmaceutically acceptable salt and/or solvate (e.g. salt) and/or derivative thereof, and a pharmaceutically acceptable carrier or excipient.

In one embodiment, there is provided a pharmaceutical composition comprising a compound of formula (I), or a pharmaceutically acceptable salt and/or solvate (e.g. salt) and/or derivative thereof, for use in the treatment or prophylaxis of a disease or disorder as described herein.

In a further embodiment, there is provided a method for the prophylaxis or treatment of a disease or disorder as described herein, which comprises administering to a subject in need thereof an effective amount of a pharmaceutical composition comprising a compound of formula (I) or a pharmaceutically acceptable salt and/or solvate (e.g. salt) and/or derivative thereof.

The invention also provides the use of a pharmaceutical composition comprising a compound of formula (I), or a pharmaceutically acceptable salt and/or solvate thereof (e.g. salt) and/or derivative thereof, in the manufacture of a medicament for the treatment or prophylaxis of a disease or disorder as described herein.

The compounds of formula (I) or their pharmaceutically acceptable salts and/or solvates and/or derivatives thereof may be administered by any convenient method, e.g. by oral, parenteral, buccal, sublingual, nasal, rectal or transdermal administration, and the pharmaceutical compositions adapted accordingly.

The compounds of formula (I) or their pharmaceutically acceptable salts and/or solvates and/or derivatives thereof may be administered topically, for example to the eye, gut or skin. Thus, in an embodiment there is provided a pharmaceutical composition comprising a compound of the invention optionally in combination with one or more topically acceptable diluents or carriers.

A pharmaceutical composition of the invention may be delivered topically to the skin. Compositions suitable for transdermal administration include ointments, gels and patches. Such a pharmaceutical composition may also suitably be in the form of a cream, lotion, foam, powder, paste or tincture.

The pharmaceutical composition may suitably include vitamin D3 analogues (e.g calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid.

A pharmaceutical composition of the invention may be delivered topically to the eye. Such a pharmaceutical composition may suitably be in the form of eye drops or an ointment.

A pharmaceutical composition of the invention may be delivered topically to the gut. Such a pharmaceutical composition may suitably be delivered orally, such as in the form of a tablet or a capsule, or rectally, such as in the form of a suppository.

Suitably, delayed release formulations are in the form of a capsule.

The compounds of formula (I) or their pharmaceutically acceptable salts and/or solvates and/or derivatives thereof which are active when given orally can be formulated as liquids or solids, e.g. as syrups, suspensions, emulsions, tablets, capsules or lozenges.

A liquid formulation will generally consist of a suspension or solution of the active ingredient (such as a compound of formula (I) or a pharmaceutically acceptable salt and/or solvate (e.g. salt) and/or derivative thereof) in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient (such as a compound of formula (I) or a pharmaceutically acceptable salt and/or solvate (e.g. salt) and/or derivative thereof) can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient (such as a compound of formula (I) or a pharmaceutically acceptable salt and/or solvate (e.g. salt) and/or derivative thereof) in a sterile aqueous carrier or parenterally acceptable oil, e.g. polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluoro-chloro-hydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Suitably, the composition is in unit dose form such as a tablet, capsule or ampoule.

The composition may for example contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 2000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment or prophylaxis of the aforementioned disorders will vary in the usual way with the seriousness of the disorders, the weight of the sufferer, and other similar factors. However, as a general guide suitable unit doses may be 0.05 mg to 1000 mg, more suitably 1.0 mg to 500 mg, and such unit doses may be administered more than once a day, for example two or three a day. Such therapy may extend for a number of weeks or months.

The invention provides, in a further aspect, a combination comprising a compound of formula (I) or a pharmaceutically acceptable, salt, solvate and/or derivative thereof (e.g. a combination comprising a compound of formula (I) or a pharmaceutically acceptable derivative thereof) together with a further pharmaceutically acceptable active ingredient or ingredients.

The invention provides a compound of formula (I), for use in combination with a further pharmaceutically acceptable active ingredient or ingredients.

When the compounds are used in combination with other therapeutic agents, the compounds may be administered separately, sequentially or simultaneously by any convenient route. Optimal combinations may depend on the disease or disorder. Possible combinations include those with one or more active agents selected from the list consisting of:

5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, sirolimus, methotrexate, azathioprine mycophenolate mofetil, leflunomide, cyclophosphamide, 6-mercaptopurine or anti-lymphocyte (or thymocyte) globulins); anti-TNF-alpha antibodies (e.g., infliximab, adalimumab, certolizumab pegol or golimumab); anti-IL12/IL23 antibodies (e.g., ustekinumab); anti-IL6 or anti-IL6R antibodies, anti-IL17 antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK inhibitors including JAK1 and JAK3 inhibitors (e.g., tofacitinib, baricitinib, R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071).

For cancer, the further pharmaceutically acceptable active ingredient may be selected from anthracyclins such as doxorubicin; anti-mitotic agents such as vinblastine, paclitaxel and docetaxel; alkylating agents, for example cisplatin, carboplatin, dacarbazine and cyclophosphamide; antimetabolites, for example 5-fluorouracil, cytosine arabinoside and hydroxyurea; intercalating agents for example adriamycin and bleomycin; topoisomerase inhibitors for example etoposide, topotecan and irinotecan; thymidylate synthase inhibitors for example raltitrexed; PI3 kinase inhibitors for example idelalisib; mTor inhibitors for example everolimus and temsirolimus; proteasome inhibitors for example bortezomib; histone deacetylase inhibitors for example panobinostat or vorinostat; and hedgehog pathway blockers such as vismodegib.

The further pharmaceutically acceptable active ingredient may be selected from tyrosine kinase inhibitors such as, for example, axitinib, dasatinib, erlotinib, imatinib, nilotinib, pazopanib and sunitinib.

Anticancer antibodies may be included in a combination therapy and may be selected from the group consisting of olaratumab, daratumumab, necitumumab, dinutuximab, traztuzumab emtansine, pertuzumab, obinutuzumab, brentuximab, ofatumumab, panitumumab, catumaxomab, bevacizumab, cetuximab, tositumomab, traztuzumab, gentuzumab ozogamycin and rituximab.

Compounds or pharmaceutical compositions of the invention may also be used in combination with radiotherapy.

Some of the combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations. The individual components of combinations may also be administered separately, through the same or different routes.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Medical Devices

In an embodiment, compounds of the invention or pharmaceutical compositions comprising said compounds may be formulated to permit incorporation into the medical device, thus providing application of the compound or composition directly to the site to prevent or treat conditions disclosed herein.

In an embodiment, the compounds of the invention or pharmaceutical composition thereof is formulated by including it within a coating onto the medical device. There are various coatings that can be utilized such as, for example, polymer coatings that can release the compound over a prescribed time period. The compound, or a pharmaceutical composition thereof, can be embedded directly within the medical device. In some embodiments, the compound is coated onto or within the device in a delivery vehicle such as a microparticle or liposome that facilitates its release and delivery. In some embodiments, the compound or pharmaceutical composition is miscible in the coating.

In some embodiments, the medical device is a vascular implant such as a stent. Stents are utilized in medicine to prevent or eliminate vascular restrictions. The implants may be inserted into a restricted vessel whereby the restricted vessel is widened. Excessive growth of the adjacent cells following vascular implantation results in a restriction of the vessel particularly at the ends of the implants which results in reduced effectiveness of the implants. If a vascular implant is inserted into a human artery for the elimination of for example an arteriosclerotic stenosis, intimahyperplasia can occur within a year at the ends of the vascular implant and results in renewed stenosis ("restenosis").

Accordingly, in some embodiments, the stents are coated or loaded with a composition including a compound of the invention or pharmaceutical composition thereof and optionally a targeting signal, a delivery vehicle, or a combination thereof. Many stents are commercially available or otherwise know in the art.

In some embodiments, the stent is a drug-eluting stent. Various drug eluting stents that simultaneously deliver a therapeutic substance to the treatment site while providing artificial radial support to the wall tissue are known in the art. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

In some embodiments, the devices are also coated or impregnated with a compound of the invention, or pharmaceutical composition thereof and one or more additional therapeutic agents, including, but not limited to, antiplatelet agents, anticoagulant agents, anti-inflammatory agents, antimicrobial agents, antimetabolic agents, additional anti-neointima agents, additional antiproliferative agents, immunomodulators, antiproliferative agents, agents that affect migration and extracellular matrix production, agents that affect platelet deposition or formation of thrombis, and agents that promote vascular healing and re-endothelialization, such as those and others described in Sousa et al. (2003) and Salu et al. (2004).

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon-γ Ib, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 17-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma. It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labeled compounds, barium sulfate, gadolinium oxide, bismuth derivatives, zirconium dioxide, cadmium, tungsten, gold tantalum, bismuth, platinum, iridium, and rhodium. These additives may be, but are not limited to, micro- or nano- sized particles or nano particles. Radio-opacity may be determined by fluoroscopy or by x-ray analysis.

A compound of the invention and one or more additional agents, or pharmaceutical composition thereof, can be incorporated into the stent, either by loading the compound and one or more additional agents, or pharmaceutical composition thereof into the absorbable material prior to processing, and/or coating the surface of the stent with the agent(s). The rate of release of agent may be controlled by a number of methods including varying the following the ratio of the absorbable material to the compound and one or more additional agents, or pharmaceutical composition, the molecular weight of the absorbable material, the composition of the compound and one or more additional agents, or pharmaceutical composition, the composition of the absorbable polymer, the coating thickness, the number of coating layers and their relative thicknesses, and/or the compound and one or more additional agents, or pharmaceutical composition concentration. Top coats of polymers and other materials, including absorbable polymers, may also be applied to active agent coatings to control the rate of release. For example, P4HB can be applied as a top coat on a metallic stent coated with P4HB including an active agent to retard the release of the active agent.

The invention is further exemplified by the following non-limiting examples.

EXAMPLES

Abbreviations used herein are defined below. Any abbreviations not defined are intended to convey their generally accepted meaning.

ABBREVIATIONS

AcOH glacial acetic acid
$AlMe_3$ trimethylaluminium
aq aqueous
Ar aromatic ring
BEH ethylene bridged hybrid
Bispin bis(pinacolato)diboron; 4,4,4',4',5,5,5',5'-Octamethyl-2,2'-bi-1,3,2-dioxaborolane
Bz benzyl ($CH_2$-phenyl)
BOC tert-butyloxycarbonyl protecting group
$Cs_2CO_3$ cesium carbonate
CSH charged surface hybrid
d doublet
DCM dichloromethane
DIBAL-H diisobutylaluminium hydride
DIPEA N,N-diisopropylethylamine
dioxane 1,4-dioxane
DMF N,N-dimethylformamide
DMSO dimethyl sulfoxide
DPPA diphenylphosphoryl azide
dppf 1,1'-bis(diphenylphosphino)ferrocene
($ES^+$) electrospray ionisation, positive mode
($ES^-$) electrospray ionisation, negative mode
ESI electrospray ionisation
Et ethyl
EtMgBr ethyl magnesium bromide
EtOAc ethyl acetate
EtOH ethanol
Fmoc fluorenylmethyloxycarbonyl
g grams
HATU 1-[bis(dimethylamino)methylene]-1H-1,2,3-triazolo[4,5-b]pyridinium 3-oxid hexafluorophosphate
HCl hydrochloric acid
HPLC high performance liquid chromatography
hr(s) hour(s)
$H_2SO_4$ sulfuric acid
$IC_{50}$ 50% inhibitory concentration
$K_2CO_3$ potassium carbonate
LCMS liquid chromatography-mass spectrometry
LiOH lithium hydroxide
$(M+H)^+$ protonated molecular ion
$(M-H)^-$ unprotonated molecular ion
M molar concentration
mL millilitre
mm millimeter
mmol millimole
$MgSO_4$ magnesium sulfate
Me methyl
MeCN acetonitrile
MeMgBr methyl magnesium bromide
MeOH methanol
MHz megahertz
min(s) minute(s)
MSD mass selective detector
m/z mass-to-charge ratio N₂ nitrogen gas
NH₃ ammonia
NH₄Cl ammonium chloride
NaH sodium hydride
Na₂SO₄ sodium sulfate
NaHCO₃ sodium bicarbonate
nM nanomolar
nm nanometre
NMR nuclear magnetic resonance (spectroscopy)
PDA photodiode array
PdCl₂(dppf)·CH₂Cl₂ [1,1'-bis(diphenylphosphino)ferrocene]dichloropalladium(II) dichloromethane
prep HPLC preparative high performance liquid chromatography
Ph phenyl
pos/neg positive/negative
q quartet
RT room temperature
Rt retention time
RP reverse phase
s singlet
S$_N$Ar nucleophilic aromatic substitution
sat saturated
SCX solid supported cation exchange (resin)
t triplet
T3P 2,4,6-tripropyl-1,3,5,2,4,6-trioxatriphosphorinane-2,4,6-trioxide
TBME tert-butyl methyl ether
TFA trifluoroacetic acid
TMSOK potassium trimethylsilanolate
THF tetrahydrofuran
UPLC ultra performance liquid chromatography
UV ultraviolet
v/v volume/volume
VWD variable wave detector
wt weight
um micrometre
uM micromolar
uL microlitre General Procedures All starting materials and solvents were obtained either from commercial sources or prepared according to the literature. Unless otherwise stated all reactions were stirred. Organic solutions were routinely dried over anhydrous magnesium sulfate or sodium sulfate. Hydrogenations were performed on a Thales H-cube flow reactor under the conditions stated.

Column chromatography was performed on pre-packed silica (230-400 mesh, 40-63 um) cartridges using the amount indicated. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M NH₃ in MeOH.

Preparative Reverse Phase High Performance Liquid Chromatography (HPLC)

Prep HPLC

Acidic Prep

Waters X-Select CSH column C18, 5 um (19×50 mm), flow rate 28 mL min⁻¹ eluting with a H₂O-MeCN gradient containing 0.1% v/v formic acid over 6.5 min using UV detection at 254 nm.

Basic Prep

Waters X-Bridge Prep column C18, 5 um (19×50 mm), flow rate 28 mL min⁻¹ eluting with a 10 mM NH₄HCO₃-MeCN gradient over 6.5 min using UV detection at 254 nm.

Prep Chiral HPLC

Chiral Method A: Chiralpak® IA (Daicel Ltd.) column (2×25 cm), flow rate 13.5 mL min⁻¹ eluting with a mixture of (30%) EtOH in a 4:1 mixture of heptane+0.2% TFA and CHCl₃, UV detection at 254 nm. Samples were loaded onto the column via an at-column dilution pump, pumping (EtOH) (1.5 mL min⁻¹) for the duration of the run, giving a combined flow rate of 15 mL min⁻¹

Chiral Method B: Chiralpak® IA (Daicel Ltd.) column (2×25 cm), flow rate 13.5 mL min⁻¹ eluting with a mixture of (40%) EtOH in a 4:1 mixture of heptane+0.2% TFA and CHCl₃, UV detection at 254 nm. Samples were loaded onto the column via an at-column dilution pump, pumping (EtOH) (1.5 mL min⁻¹) for the duration of the run, giving a combined flow rate of 15 mL min⁻¹

Analytical Methods

Reverse Phase HPLC Conditions for the LCMS Analytical Methods

HPLC acidic: Acidic LCMS 4 minute (5-95%)

Analytical LCMS was carried out using a Waters X-Select CSH C18, 2.5 um, 4.6×30 mm column eluting with a gradient of 0.1% formic acid in MeCN in 0.1% formic acid in water. The gradient from 5-95% 0.1% formic acid in MeCN occurred between 0.00-3.00 minutes at 2.5 mL/min with a flush from 3.01-3.5 minutes at 4.5 mL/min. A column re-equilibration to 5% MeCN was from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

HPLC basic: Basic LCMS 4 minute (5-95%)

Analytical LCMS was carried out using a Waters X-Select BEH C18, 2.5 um, 4.6×30 mm column eluting with a gradient of MeCN in aqueous 10 mM ammonium bicarbonate. The gradient from 5-95% MeCN occurred between 0.00-3.00 minutes at 2.5 mL/min with a flush from 3.01-3.5 minutes at 4.5 mL/min. A column re-equilibration to 5% MeCN was from 3.60-4.00 minutes at 2.5 mL/min. UV spectra of the eluted peaks were measured using an Agilent 1260 Infinity VWD at 254 nm. Mass spectra were measured using an Agilent 6120 MSD running with positive/negative switching.

Reverse Phase HPLC Conditions for the UPLC Analytical Methods

UPLC acidic: Acidic UPLC 3 minute

Analytical UPLC/MS was carried out using a Waters Acquity CSH C18, 1.7 um, 2.1×30 mm column eluting with a gradient of 0.1% formic acid in MeCN in 0.1% formic acid in water. The gradient was structured with a starting point of 5% MeCN held from 0.0-0.11 minutes. The gradient from 5-95% occurred between 0.11-2.15 minutes with a flush from 2.15-2.56 minutes. A column re-equilibration to 5% MeCN was from 2.56-2.83 minutes. UV spectra of the eluted peaks were measured using an Acquity PDA and mass spectra were recorded using an Acquity QDa detector with ESI positive/negative switching.

UPLC basic: Basic UPLC 3 minute

Analytical UPLC/MS was carried out using a Waters Acquity BEH C18, 1.7 um, 2.1×30 mm column eluting with a gradient of MeCN in aqueous 10 mM ammonium bicarbonate. The gradient was structured with a starting point of 5% MeCN held from 0.0-0.11 minutes. The gradient from 5-95% occurred between 0.11-2.15 minutes with a flush from 2.15-2.56 minutes. A column re-equilibration to 5%

MeCN was from 2.56-2.83 minutes. UV spectra of the eluted peaks were measured using an Acquity PDA and mass spectra were recorded using an Acquity QDa detector with ESI positive/negative switching.

Column temperature was 40° C. in all runs. Injection volume was 3 uL and the flow rate was 0.77 mL/min. PDA scan from 210-400 nm was conducted on all runs.

Normal Phase HPLC Conditions for the Chiral Analytical Methods

Chiral IA method 1: Chiral HPLC (Daicel Chiralpak IA, 5 um, 4.6×250 mm, 1.0 mL/min, 5-95% (gradient over 45 min) EtOH (0.2% TFA) in [4:1 heptane (0.2% TFA):CHCl$_3$].

Chiral IA method 2: Chiral HPLC (Daicel Chiralpak IA, 5 um, 4.6×250 mm, 1.0 mL/min, Isocratic 40% EtOH (0.2% TFA) in [4:1 heptane (0.2% TFA):CHCl$_3$].

Chiral IC method 1: Chiral HPLC (Daicel Chiralpak IA, 5 um, 4.6×250 mm, 0.5 mL/min, Isocratic 70% EtOH (0.2% TFA) in [4:1 iso-hexane (0.2% TFA):CHCl$_3$].

$^1$H NMR Spectroscopy $^1$H NMR spectra were acquired on a Bruker Avance 11 spectrometer at 400 MHz or Bruker Avance III HD spectrometer at 500 MHz using residual undeuterated solvent as reference and unless specified otherwise were run in DMSO-d$_6$.

Preparation of Intermediates

Known synthetic intermediates were procured from commercial sources or were obtained using published literature procedures. Additional intermediates were prepared by the representative synthetic processes described herein.

Ethyl 2-(cyclopropanesulfonamido)thiazole-4-carboxylate INTE1

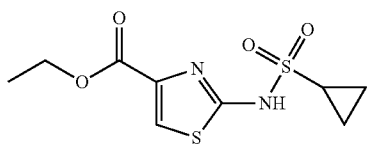 [SMILES: CCOC(=O)c1csc(NS(=O)(=O)C2CC2)n1]

A solution of ethyl 2-aminothiazole-4-carboxylate (6.49 g, 37.7 mmol) and cyclopropanesulfonyl chloride (4 mL, 39.5 mmol) in pyridine (15 mL) was warmed to 40° C. and stirred for 48 hrs. The reaction mixture was taken up in DMSO (20 mL) and the crude product was purified by reverse phase chromatography on C18 silica (330 g column, 10-20% MeCN/10 mM ammonium bicarbonate) to afford the product which was then taken up in EtOAc (300 mL) and washed with 1 M HCl (aq, 300 mL) and brine (150 mL). The organic layer was dried (Na$_2$SO$_4$), filtered and concentrated to afford ethyl 2-(cyclopropanesulfonamido)thiazole-4-carboxylate (4.7 g, 15.31 mmol, 41% yield) as an orange oil; Rt 1.36 min (HPLC acidic); m/z 277 (M+H)$^+$ (ES$^+$); $^1$H NMR (400 MHz, DMSO-d$_6$) δ 13.14 (s, 1H), 7.72 (s, 1H), 4.28 (q, J=7.1 Hz, 2H), 2.72-2.58 (m, 1H), 1.29 (t, J=7.1 Hz, 3H), 1.01-0.81 (m, 4H).

N-(4-Formylthiazol-2-yl)cyclopropanesulfonamide INTE2

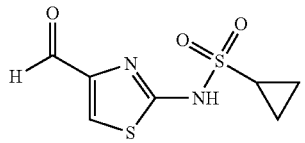 [SMILES: O=Cc1csc(NS(=O)(=O)C2CC2)n1]

A solution of ethyl 2-(cyclopropanesulfonamido)thiazole-4-carboxylate INTE1 (1.0 g, 3.62 mmol) in DCM (10 mL) was cooled to −78° C. whereupon DIBAL-H (1 M in DCM) (14.5 mL, 14.5 mmol) was added dropwise over 30 mins. The reaction was then stirred at this temperature for 2 hrs. MeOH (1.5 mL) was added cautiously before the reaction mixture was allowed to warm to RT. DCM (50 mL) was then added, followed by 1 M HCl (aq, 90 mL) with vigorous stirring. The mixture was stirred for 10 mins before being passed through a phase separator and further extracting with DCM (50 mL). The organic layers were combined and concentrated onto silica (2 g) and the crude product was purified by chromatography on silica (40 g column, 20-80% EtOAc/iso-hexanes) to afford N-(4-formylthiazol-2-yl)cyclopropanesulfonamide (122 mg, 0.5 mmol, 14% yield) as a colourless gum; Rt 0.53 min (UPLC acidic); m/z 233 (M+H)$^+$ (ES$^+$); $^1$H NMR (400 MHz, DMSO-d$_6$) δ 13.17 (s, 1H), 9.52 (s, 1H), 8.06 (s, 1H), 2.73-2.57 (m, 1H), 1.04-0.67 (m, 4H).

2-(Cyclopropanesulfonamido)thiazole-4-carboxylic acid INTE3

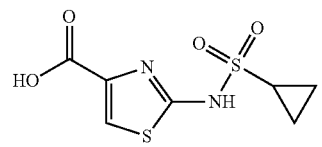 [SMILES: O=C(O)c1csc(NS(=O)(=O)C2CC2)n1]

A solution of ethyl 2-(cyclopropanesulfonamido)thiazole-4-carboxylate INTE1 (1.3 g, 4.70 mmol) in 2 M LiOH (aq, 4.70 mL, 9.41 mmol), MeOH (1 mL) and THF (6 mL) was stirred at RT. The reaction mixture was part concentrated (to approx. 6 mL) then acidified with 1 M HCl (aq. 12 mL). The aqueous layer was then extracted with EtOAc (3×20 mL), then the organic phases were combined, dried (Na$_2$SO$_4$), filtered and concentrated to afford 2-(cyclopropanesulfonamido)thiazole-4-carboxylic acid (910 mg, 3.59 mmol, 76% yield) as a colourless solid; Rt 0.65 min (UPLC acidic); m/z 249 (M+H)$^+$ (ES$^+$); $^1$H NMR (400 MHz, DMSO-d$_6$) δ 13.83-12.58 (br. s, 2H), 7.61 (s, 1H), 2.67-2.58 (m, 1H), 1.07-0.73 (m, 4H).

2-(Cyclopropanesulfonamido)-N-methoxy-N-methylthiazole-4-carboxamide INTE4

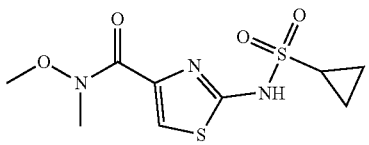 [SMILES: CON(C)C(=O)c1csc(NS(=O)(=O)C2CC2)n1]

A solution of 2-(cyclopropanesulfonamido)thiazole-4-carboxylic acid INTE3 (910 mg, 3.67 mmol) and N,O-dimethylhydroxylamine hydrochloride (358 mg, 3.67 mmol) in DMF (6 mL) was treated with DIPEA (2.2 mL, 12.8 mmol) and stirred for 5 mins before HATU (1.3 g, 3.67 mmol) was added, the reaction mixture was stirred at RT for 20 hrs. The reaction mixture was taken up in 1 M HCl (aq, 50 mL) which was extracted with EtOAc (3×50 mL). The organic phases were combined, dried (Na$_2$SO$_4$), filtered and concentrated onto silica (5 g). The crude product was purified by chromatography on silica (24 g column, 0-100% EtOAc/iso-hexanes) to afford 2-(cyclopropanesulfonamido)-N-methoxy-N-methylthiazole-4-carboxamide (786 mg, 2.64 mmol, 72% yield) as a colourless solid; Rt 0.73 min (UPLC acidic); m/z 292 (M+H)$^+$ (ES$^+$); $^1$H NMR (400 MHz, DMSO-d$_6$) δ 12.75 (s, 1H), 7.58 (s, 1H), 3.73 (s, 3H), 3.26 (s, 3H), 2.68-2.58 (m, 1H), 1.00-0.84 (m, 4H).

N-(4-Propionylthiazol-2-yl)cyclopropanesulfonamide
INTE5

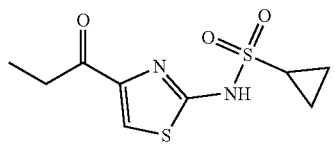 [SMILES: CCC(=O)c1csc(NS(=O)(=O)C2CC2)n1]

A suspension of 2-(cyclopropanesulfonamido)-N-methoxy-N-methylthiazole-4-carboxamide INTE4 (2.5 g, 8.58 mmol) in THF (100 mL) at 40° C. was treated dropwise with 2 M EtMgCl (THF, 8.6 mL, 17.2 mmol). The reaction mixture was maintained at 40° C. for 18 hrs. The reaction mixture was quenched by addition of NH$_4$Cl (sat. aq, 30 mL) followed by EtOAc (50 mL) and water (20 mL). The phases were partitioned and the aqueous layer was extracted with EtOAc (50 mL), the organic phases were combined, dried (Na$_2$SO$_4$), filtered and concentrated onto silica (10 g). The crude product was purified by chromatography on silica (24 g column, 0-50% EtOAc/iso-hexanes) to afford N-(4-propionylthiazol-2-yl)cyclopropanesulfonamide (1.9 g, 5.84 mmol, 68% yield) as an off white gum; Rt 1.24 min (HPLC acidic); m/z 261 (M+H)$^+$ (ES$^+$); $^1$H NMR (400 MHz, DMSO-d$_6$) δ 12.92 (s, 1H), 7.95 (s, 1H), 2.86 (q, J=7.2 Hz, 2H), 2.68-2.58 (m, 1H), 1.05 (t, J=7.2 Hz, 3H), 0.97-0.80 (m, 4H).

N-(4-acetylthiazol-2-yl)cyclopropanesulfonamide
INTE21

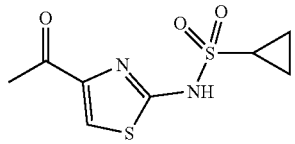

Prepared as for INTE1 using commercial 1-(2-aminothiazol-4-yl)ethanone to afford N-(4-acetylthiazol-2-yl)cyclopropanesulfonamide (30% yield) as a yellow gum. Rt 1.00 (HPLC acidic); m/z 247 (M+H)$^+$ (ES$^+$); $^1$H NMR (500 MHz, DMSO-d6) δ 12.92 (s, 1H), 7.98 (s, 1H), 2.70-2.58 (m, 1H), 2.43 (s, 3H), 1.00-0.80 (m, 4H).

Method A: Reductive Amination

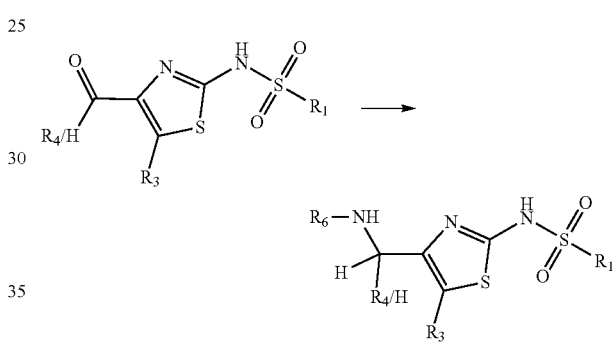

A solution of aldehyde/ketone (1 eq.) in THF was treated with AcOH (1 eq.), amine (1 eq.) and a reducing agent such as STAB (1.2 eq.) and stirred at RT for 1 hr. The reaction mixture was quenched by addition of MeOH then loaded directly on to SCX (1 g/mmol of substrate), washed with MeOH and the product was eluted with 1 M NH$_3$ in MeOH. The crude product was then concentrated onto silica and purified by normal phase chromatography.

TABLE 1

| | | | |
|---|---|---|---|
| The following intermediates were made according to Method A. | | | |
| INT | Name/Structure (All examples containing chiral centres are racemates unless stated) | Synthesis Method, [LCMS Method], m/z (M + H)$^+$, (Rt/min) | $^1$H NMR Chemical Shift Data (DMSO-d$_6$ unless stated) |
| INTE6 | N-(4-(((2,4-dimethoxybenzyl)amino)methyl)thiazol-2-yl)cyclopropanesulfonamide | Using INTE2 [HPLC acidic], 384 (0.99). | 7.23 (d, J = 8.3 Hz, 1H), 6.56 (d, J = 2.4 Hz, 1H), 6.52 (d, J = 2.4 Hz, 1H), 6.50 (d, J = 2.3 Hz, 1H), 3.79 (s, 3H), 3.76 (s, 3H), 3.74 (s, 2H), 3.63-3.61 (m, 2H), 2.49-2.45 (m, 1H), 0.89-0.72 (m, 4H), zwitterion, 2 × N—H not observed. |

TABLE 1-continued

*The following intermediates were made according to Method A.*

| INT | Name/Structure (All examples containing chiral centres are racemates unless stated) | Synthesis Method, [LCMS Method], m/z (M + H)+, (Rt/min) | ¹H NMR Chemical Shift Data (DMSO-d₆ unless stated) |
|---|---|---|---|
| INTE7 | N-(4-(1-((2,4-dimethoxybenzyl)amino)propyl)thiazol-2-yl)cyclopropanesulfonamide | Using INTE5 [UPLC acidic], 412 (0.62). | 7.18 (d, J = 8.3 Hz, 1H), 6.59-6.37 (m, 3H), 3.76 (s, 3H), 3.75 (s, 3H), 3.64-3.43 (m, 3H), 2.58-2.52 (m, 1H), 1.76-1.57 (m, 2H), 0.91-0.81 (m, 4H), 0.78 (t, J = 7.4 Hz, 3H), 2 × N—H not observed. |
| INTE8 | N-(4-(1-((4-methoxybenzyl)(methyl)amino)propyl)thiazol-2-yl)cyclopropanesulfonamide | Using INTE5, [HPLC basic], 396 (1.63). | 12.11 (v. br. s, 1H), 7.26-7.18 (m, 2H), 6.91-6.83 (m, 2H), 6.58 (s, 1H), 3.73 (s, 3H), 3.55-3.42 (m, 2H), 3.39-3.26 (m, 1H), 2.65-2.57 (m, 1H), 1.99 (s, 3H), 1.91-1.57 (m, 2H), 0.97-0.84 (m, 5H), 0.75-0.65 (m, 2H). |
| INTE22 | N-(4-(1-((2,4-dimethoxybenzyl)amino)ethyl)thiazol-2-yl)cyclopropanesulfonamide | Using INTE21 [HPLC basic], 398 (1.43). | None recorded |

Method B: Benzylamine Deprotection (TFA)

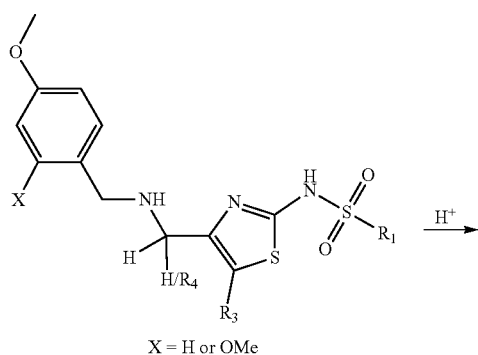

X = H or OMe

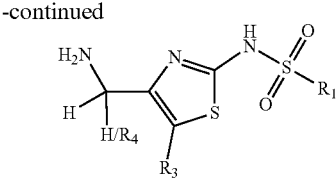

Benzylamine derivative (1 eq.) was dissolved in TFA (50 eq.) and heated to 70° C. for 1-24 hrs. The reaction was allowed to cool to RT, then was loaded on to SCX (1 g/mmol of substrate) and washed with MeOH. The required compound was eluted with 1% NH₃ in MeOH.

TABLE 2

The following intermediates were made according to Method B.

| INT | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTE9 | N-(4-(aminomethyl)thiazol-2-yl)cyclopropanesulfonamide | Using INTE6, [UPLC basic], 234 (0.23). | 6.44 (s, 1H), 3.79-3.70 (m, 2H), 2.46-2.33 (m, 1H), 0.85-0.75 (m, 2H), 0.74-0.61 (m, 2H), 3 × NH not observed. |
| INTE10 | N-(4-(1-aminopropyl)thiazol-2-yl)cyclopropanesulfonamide | Using INTE7, [HPLC basic], 262 (M + H)+ (ES+); (0.51). | 8.00 (v. br. s, 3H), 6.43 (s, 1H), 3.98-3.73 (m, 1H, obscured by impurity), 2.42-2.28 (m, 1H), 1.92-1.62 (m, 2H), 0.95-0.40 (m, 7H). |
| INTE11 | N-(4-(1-(methylamino)propyl)thiazol-2-yl)cyclopropanesulfonamide | Using INTE8, [HPLC acidic], 276 (0.34). | 6.49 (s, 1H), 3.70-3.57 (m, 1H), 2.44-2.34 (m, 1H), 2.32 (s, 3H), 1.82-1.69 (m, 2H), 0.84-0.74 (m, 5H), 0.74-0.66 (m, 2H), 2 × NH not observed |
| INTE23 | N-(4-(1-aminoethyl)thiazol-2-yl)cyclopropanesulfonamide | Using INTE21, No Data recorded | 6.39 (d, J = 0.8 Hz, 1H), 4.16-4.02 (m, 1H), 2.46-2.26 (m, 1H), 1.41 (d, J = 6.7 Hz, 3H), 0.84-0.73 (m, 2H), 0.72-0.56 (m, 2H), 3 × exchangeable N—H not observed. |

N-(4-(2-Hydroxypropan-2-yl)thiazol-2-yl)cyclopropanesulfonamide INTE12

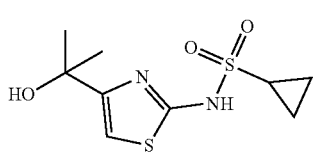 [SMILES: CC(C)(O)c1csc(NS(=O)(=O)C2CC2)n1]

A solution of ethyl 2-(cyclopropanesulfonamido)thiazole-4-carboxylate INTE1 (2.7 g, 9.77 mmol) in THF (30 mL) was cooled to 0° C. then MeMgBr (3.4 M in THF, 14.4 mL, 48.9 mmol) was added dropwise, over approx. 20 mins, maintaining the temperature below 10° C. Once addition was complete the reaction mixture was allowed to warm to RT and was stirred for 24 hrs. The reaction mixture was cooled with an ice bath and NH4Cl (sat. aq, 10 mL) was added cautiously, resulting in precipitate formation. 1 M HCl (aq, 50 mL) was added and the reaction mixture was extracted with EtOAc (3×50 mL). The organic phases were combined, dried (MgSO4), filtered and concentrated onto silica (10 g). The product was then purified by chromatography on silica (24 g column, 0-100% EtOAc/iso-hexanes) to afford N-(4-(2-hydroxypropan-2-yl)thiazol-2-yl)cyclopropanesulfonamide (1.03 g, 3.53 mmol, 36% yield) as a pale yellow solid: Rt 1.05 min (HPLC acidic); m/z 263 (M+H)+ (ES+); 1H NMR (400 MHz, DMSO-d6) δ 12.44 (s, 1H), 6.42 (s, 1H), 5.35 (s, 1H), 2.64-2.54 (m, 1H), 1.40 (s, 6H), 0.96-0.74 (m, 4H).

2-Chloro-N-(2-(2-(cyclopropanesulfonamido)thiazol-4-yl)propan-2-yl)acetamide INTE13

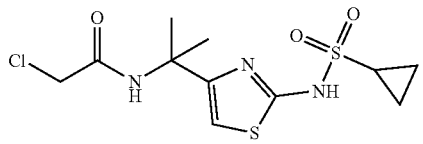 [SMILES: CC(C)(NC(=O)CCl)c1csc(NS(=O)(=O)C2CC2)n1]

A mixture of N-(4-(2-hydroxypropan-2-yl)thiazol-2-yl)cyclopropanesulfonamide INTE12 (500 mg, 1.91 mmol) and 2-chloroacetonitrile (0.72 mL, 11.4 mmol) in AcOH (0.87 mL, 15 mmol) was cooled in an ice bath before $H_2SO_4$ (0.92 mL, 17.2 mmol) was added. The reaction was allowed to warm to RT and was stirred for 18 hrs. The solution was poured onto ice water (10 mL) and extracted with DCM (3×10 mL), partitioning with a phase separator. The crude product was purified by chromatography on silica (12 g column, 0-100% EtOAc/iso-hexanes) to afford 2-chloro-N-(2-(2-(cyclopropanesulfonamido)thiazol-4-yl)propan-2-yl)acetamide (574 mg, 1.61 mmol, 85% yield) as an orange gum; Rt 0.78 min (UPLC acidic); m/z 337 ($^{35}$Cl M+H)$^+$ (ES$^+$); $^1$H NMR (400 MHz, DMSO-d$_6$) δ 12.46 (s, 1H), 8.29 (s, 1H), 6.44 (s, 1H), 4.11-3.87 (m, 2H), 2.63-2.53 (m, 1H), 1.51 (s, 6H), 0.97-0.83 (m, 4H).

N-(4-(2-Aminopropan-2-yl)thiazol-2-yl)cyclopropanesulfonamide INTE14

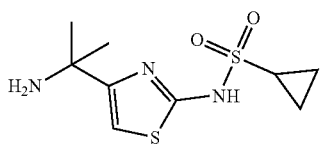 [SMILES: CC(C)(N)c1csc(NS(=O)(=O)C2CC2)n1]

A suspension of thiourea (154 mg, 2.03 mmol) and 2-chloro-N-(2-(2-(cyclopropanesulfonamido)thiazol-4-yl)propan-2-yl)acetamide INTE13 (570 mg, 1.69 mmol) in EtOH (8 mL) was treated with AcOH (1.6 mL, 28.7 mmol) and heated to reflux for 20 hrs. The reaction mixture was allowed to cool to RT. The resulting precipitate was filtered and the filtrate was loaded onto SCX (5 g), washed with MeOH and the required product was isolated by eluting with 1% $NH_3$ in MeOH to afford N-(4-(2-aminopropan-2-yl)thiazol-2-yl)cyclopropanesulfonamide (479 mg, 1.80 mmol, quant. yield) as a slightly pink solid; Rt 0.50 min (UPLC basic); m/z 262 (M+H)$^+$ (ES$^+$); $^1$H NMR (400 MHz, DMSO-d$_6$) δ 6.38 (s, 1H), 2.44-2.21 (m, 1H), 1.49 (s, 6H), 0.89-0.35 (m, 4H), 3×H exchangeable protons were very broad and are not reported.

N-(4-(3-hydroxypentan-3-yl)thiazol-2-yl)cyclopropanesulfonamide INTE15

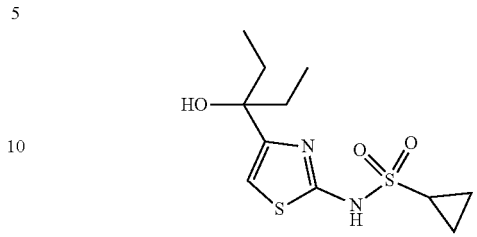

A solution of ethyl 2-(cyclopropanesulfonamido)thiazole-4-carboxylate INTE1 (3 g, 10.86 mmol) in THF (50 mL) was cooled to 0° C., then EtMgBr (2 M in THF) (27.1 mL, 54.3 mmol) was added dropwise over approx. 20 mins, maintaining the temperature below 20° C. Once addition was complete the reaction mixture was warmed to RT and was stirred for 1 hr after which the reaction mixture was cooled with an ice bath and 1 M HCl (aq, 65 mL) was added cautiously. The aqueous layer was extracted with EtOAc (3×50 mL). The organic phases were combined, dried ($Na_2SO_4$), filtered and concentrated onto silica (10 g). The product was purified by chromatography on silica (24 g column, 0-100% EtOAc/iso-hexanes) to afford N-(4-(3-hydroxypentan-3-yl)thiazol-2-yl)cyclopropane sulfonamide (2.13 g, 6.97 mmol, 64% yield) as a colourless solid. Rt 0.86 min (UPLC, acidic); m/z 313.2 (M+Na)$^+$ (ES$^+$); $^1$H NMR (400 MHz, DMSO-d$_6$) δ 12.29 (s, 1H), 6.37 (s, 1H), 4.91 (s, 1H), 2.63-2.53 (m, 1H), 1.82-1.47 (m, 4H), 0.95-0.82 (m, 4H), 0.70 (t, J=7.3 Hz, 6H).

2-Chloro-N-(3-(2-(cyclopropanesulfonamido)thiazol-4-yl)pentan-3-yl)acetamide INTE16

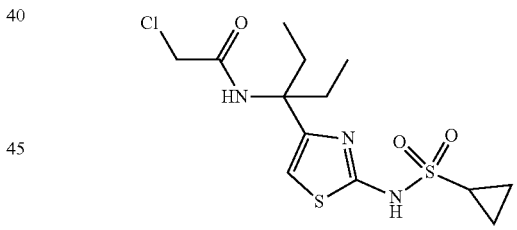

A mixture of N-(4-(3-hydroxypentan-3-yl)thiazol-2-yl)cyclopropanesulfonamide INTE15 (2.13 g, 7.33 mmol) and 2-chloroacetonitrile (2.8 mL, 44.5 mmol) in AcOH (3.4 mL, 59.4 mmol) was cooled in an ice bath before sulfuric acid (3.5 mL, 65.7 mmol) was added to afford a solution. The reaction was warmed to RT and was stirred for 18 hrs. The solution was poured onto ice water (100 mL) and extracted with DCM (3×100 mL) partitioning with a phase separator. The material was concentrated onto silica (20 g) and the crude product was purified by chromatography on silica (80 g column, 0-100% EtOAc/iso-hexanes) to afford 2-chloro-N-(3-(2-(cyclopropanesulfonamido)thiazol-4-yl)pentan-3-yl)acetamide (1.62 g, 4.21 mmol, 57% yield) as a colourless solid. Rt 0.76 min (UPLC, acidic); m/z 366.2 ($^{35}$Cl M+H)$^+$ (ES$^+$); $^1$H NMR (400 MHz, DMSO-d$_6$) δ 12.36 (s, 1H), 7.99 (s, 1H), 6.44 (s, 1H), 4.09 (s, 2H), 2.62-2.53 (m, 1H), 2.05-1.86 (m, 2H), 1.80-1.66 (m, 2H), 0.95-0.83 (m, 4H), 0.69 (t, J=7.3 Hz, 6H).

57

N-(4-(3-aminopentan-3-yl)thiazol-2-yl)cyclopropanesulfonamide INTE17

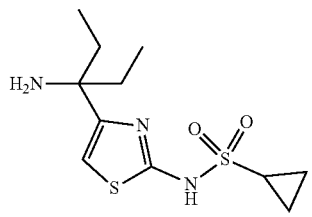 [SMILES: CCC(N)(CC)c1csc(NS(=O)(=O)C2CC2)n1]

A solution of thiourea (0.40 g, 5.25 mmol) and 2-chloro-N-(3-(2-(cyclopropanesulfonamido)thiazol-4-yl)pentan-3-yl)acetamide INTE16 (1.6 g, 4.37 mmol) in EtOH (20 mL) was treated with acetic acid (4.3 mL, 75 mmol) and heated to reflux for 18 hrs. The reaction mixture was cooled to RT, the resulting precipitate was filtered and the filtrate was loaded onto SCX (50 g), washed with MeOH and the product was isolated by eluting with 1% $NH_3$ in MeOH to afford N-(4-(3-aminopentan-3-yl)thiazol-2-yl)cyclopropanesulfonamide (1.05 g, 3.27 mmol, 75% yield) as a colourless solid. Rt 0.56 min (HPLC, basic); m/z 273.0 $(M-NH_2+H)+(ES^+)$; $^1$H NMR (400 MHz, DMSO-d$_6$) δ 7.70 (v. br s, 3H), 6.34 (s, 1H), 2.41-2.29 (m, 1H), 1.80 (app. q, J=7.4 Hz, 4H), 0.83-0.76 (m, 6H), 0.73-0.60 (m, 4H).

Methyl 2-(2-bromothiazol-4-yl)-4-methoxybutanoate INTE24

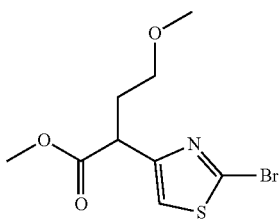

To an ice cold solution of commercial methyl 2-(2-bromothiazol-4-yl)acetate (5.0 g, 21.9 mmol) in DMF (30 mL) was added NaH (60 wt % in mineral oil 0.93 g, 23.3 mmol) portion-wise over 5 min. The resulting mixture was allowed to warm to RT under vigorous stirring for 10 min, then cooled to 0° C. before a solution of 1-bromo-2-methoxyethane (2.09 mL, 22.24 mmol) in DMF (15 mL) was added dropwise over 1 min. The resulting mixture was allowed to warm to RT and stirred for 2 hrs. The mixture was carefully poured into sat. $NH_4Cl$ (aq, 100 mL) and the aqueous phase was extracted with EtOAc (3×20 mL). The combined organic extracts were dried over $Na_2SO_4$, filtered and the solvent was removed in vacuo. The crude product was purified by chromatography on silica gel (120 g column, 0-20% EtOAc/iso-hexane) to afford methyl 2-(2-bromothiazol-4-yl)-4-methoxybutanoate (3.35 g, 11.27 mmol, 53% yield) as an orange oil. Rt 1.14 (UPLC acidic); m/z 296 ($^{81}$Br M+H)$^+$ (ES$^+$); $^1$H NMR (500 MHz, DMSO-d6) δ 7.59 (s, 1H), 3.96 (t, J=7.5 Hz, 1H), 3.61 (s, 3H), 3.31-3.19 (m, 2H), 3.18 (s, 3H), 2.26-2.14 (m, 1H), 2.09-1.95 (m, 1H).

58

2-(2-Bromothiazol-4-yl)-4-methoxybutanoic acid INTE25

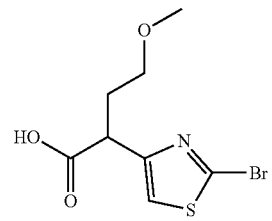

Prepared as for INTE3 using methyl 2-(2-bromothiazol-4-yl)-4-methoxybutanoate INTE24 to afford 2-(2-bromothiazol-4-yl)-4-methoxybutanoic acid (99% yield) as a white solid. Rt 0.92 (UPLC acidic); m/z 280 ($^{79}$Br M+H)$^+$ (ES$^+$); $^1$H NMR (500 MHz, DMSO-d6) δ 12.55 (s, 1H), 7.54 (s, 1H), 3.84 (t, J=7.4 Hz, 1H), 3.30-3.26 (m, 1H), 3.26-3.20 (m, 1H), 3.20 (s, 3H), 2.21-2.12 (m, 1H), 2.02-1.93 (m, 1H).

Ethyl 2-(cyclopropanesulfonamido)-5-methylthiazole-4-carboxylate INTE26

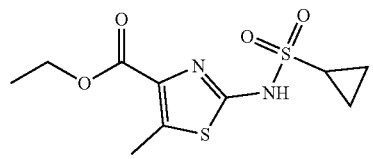 [SMILES: CCOC(=O)c1nc(NS(=O)(=O)C2CC2)sc1C]

Prepared as for INTE1 using commercial ethyl 2-amino-5-methylthiazole-4-carboxylate to afford ethyl 2-(cyclopropanesulfonamido)-5-methylthiazole-4-carboxylate (43% yield) as an off-white solid. Rt 1.60 (HPLC acidic); m/z 291 (M+H)$^+$ (ES$^+$); $^1$H NMR (500 MHz, DMSO-d6) δ 12.78 (s, 1H), 4.27 (q, J=7.1 Hz, 2H), 2.68-2.58 (m, 1H), 2.49 (s, 3H), 1.30 (t, J=7.1 Hz, 3H), 0.98-0.66 (m, 4H).

Methyl 5-chloro-2-(cyclopropanesulfonamido)thiazole-4-carboxylate INTE27

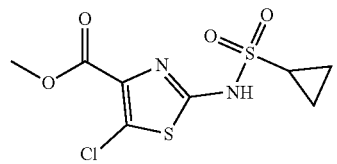 [SMILES: COC(=O)c1nc(NS(=O)(=O)C2CC2)sc1Cl]

Prepared as for INTE1 using commercial methyl 2-amino-5-chlorothiazole-4-carboxylate to afford methyl 5-chloro-2-(cyclopropanesulfonamido)thiazole-4-carboxylate (29% yield) as an off-white solid. Rt 1.63 (HPLC acidic); m/z 297 ($^{35}$Cl M+H)$^+$ (ES$^+$); $^1$H NMR (500 MHz, DMSO-d6) δ 13.07 (v. br. s, 1H), 3.84 (s, 3H), 2.81-2.68 (m, 1H), 1.03-0.90 (m, 4H).

N-(4-(2-Hydroxypropan-2-yl)-5-methylthiazol-2-yl) cyclopropanesulfonamide INTE28

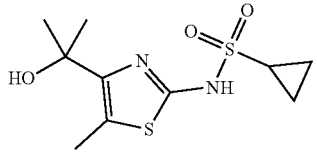 [SMILES: Cc1sc(NS(=O)(=O)C2CC2)nc1C(C)(C)O]

Prepared as for INTE12 using ethyl 2-(cyclopropanesulfonamido)-5-methylthiazole-4-carboxylate INTE26 to afford N-(4-(2-hydroxypropan-2-yl)-5-methylthiazol-2-yl) cyclopropanesulfonamide (37% yield) as an off-white solid. Rt 1.29 (HPLC acidic); m/z 277 (M+H)⁺ (ES⁺); ¹H NMR (500 MHz, DMSO-d6) δ 11.84 (s, 1H), 5.36 (s, 1H), 2.61-2.51 (m, 1H), 2.27 (s, 3H), 1.43 (s, 6H), 0.90-0.73 (m, 4H).

N-(5-Chloro-4-(2-hydroxypropan-2-yl)thiazol-2-yl) cyclopropanesulfonamide INTE29

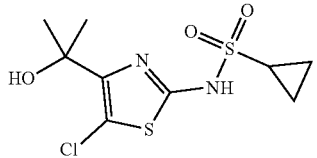 [SMILES: CC(C)(O)c1nc(NS(=O)(=O)C2CC2)sc1Cl]

Prepared as for INTE12 using methyl 5-chloro-2-(cyclopropanesulfonamido)thiazole-4-carboxylate INTE27 to afford N-(5-chloro-4-(2-hydroxypropan-2-yl)thiazol-2-yl) cyclopropanesulfonamide (44% yield) as an off-white solid. Rt 1.57 (HPLC acidic); m/z 297 (³⁵Cl M+H)⁺ (ES⁺); ¹H NMR (500 MHz, DMSO-d6) δ 12.27 (s, 1H), 5.63 (s, 1H), 2.69-2.59 (m, 1H), 1.49 (s, 6H), 1.01-0.84 (m, 4H).

2-Chloro-N-(2-(2-(cyclopropanesulfonamido)-5-methylthiazol-4-yl)propan-2-yl)acetamide INTE30

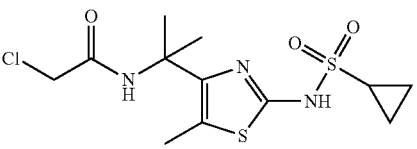 [SMILES: Cc1sc(NS(=O)(=O)C2CC2)nc1C(C)(C)NC(=O)CCl]

Prepared as for INTE13 using N-(4-(2-hydroxypropan-2-yl)-5-methylthiazol-2-yl)cyclopropanesulfonamide INTE28 to afford 2-chloro-N-(2-(2-(cyclopropanesulfonamido)-5-methylthiazol-4-yl)propan-2-yl)acetamide (95% yield) as a yellow gum. Rt 1.36 (HPLC acidic); m/z 352 (³⁵Cl M+H)⁺ (ES⁺); ¹H NMR (500 MHz, DMSO-d6) δ 11.85 (s, 1H), 8.46 (s, 1H), 4.06 (s, 2H), 2.59-2.52 (m, 1H), 2.15 (s, 3H), 1.55 (s, 6H), 0.99-0.83 (m, 4H).

2-Chloro-N-(2-(5-chloro-2-(cyclopropanesulfonamido)thiazol-4-yl)propan-2-yl)acetamide INTE31

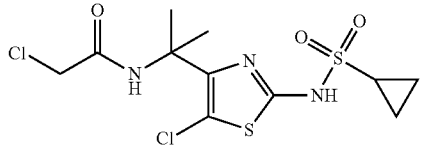 [SMILES: CC(C)(NC(=O)CCl)c1nc(NS(=O)(=O)C2CC2)sc1Cl]

Prepared as for INTE13 using N-(5-chloro-4-(2-hydroxypropan-2-yl)thiazol-2-yl)cyclopropanesulfonamide INTE29 to afford 2-chloro-N-(2-(5-chloro-2-(cyclopropanesulfonamido)thiazol-4-yl)propan-2-yl)acetamide (97% yield) as a yellow gum. Rt 1.61 (HPLC acidic); m/z 372 (³⁵Cl M+H)⁺ (ES⁺); ¹H NMR (500 MHz, DMSO-d6) δ 12.33 (s, 1H), 8.59 (s, 1H), 4.07 (s, 2H), 2.74-2.63 (m, 1H), 1.58 (s, 6H), 1.00-0.89 (m, 4H).

N-(4-(2-Aminopropan-2-yl)-5-methylthiazol-2-yl) cyclopropanesulfonamide INTE32

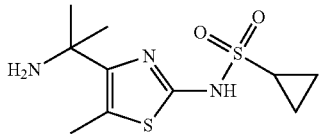 [SMILES: Cc1sc(NS(=O)(=O)C2CC2)nc1C(C)(C)N]

Prepared as for INTE14 using 2-chloro-N-(2-(2-(cyclopropanesulfonamido)-5-methylthiazol-4-yl)propan-2-yl)acetamide INTE30 to afford N-(4-(2-aminopropan-2-yl)-5-methylthiazol-2-yl)cyclopropanesulfonamide (50% yield) as a white solid. Rt 1.23 (HPLC basic); m/z 276 (M+H)⁺ (ES⁺); ¹H NMR (500 MHz, DMSO-d6) δ 7.87 (s, 3H), 2.39-2.27 (m, 1H), 2.20 (s, 3H), 1.51 (s, 6H), 0.84-0.69 (m, 2H), 0.69-0.56 (m, 2H).

N-(4-(2-Aminopropan-2-yl)-5-chlorothiazol-2-yl) cyclopropanesulfonamide INTE33

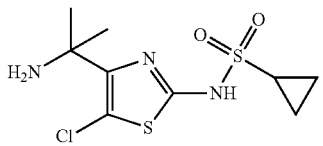 [SMILES: CC(C)(N)c1nc(NS(=O)(=O)C2CC2)sc1Cl]

Prepared as for INTE14 using 2-chloro-N-(2-(5-chloro-2-(cyclopropanesulfonamido)thiazol-4-yl)propan-2-yl)acetamide INT31 to afford N-(4-(2-aminopropan-2-yl)-5-chlorothiazol-2-yl)cyclopropanesulfonamide (37% yield) as a white solid. Rt 1.23 (HPLC basic); m/z 296 (³⁵Cl M+H)⁺ (ES⁺); ¹H NMR (500 MHz, DMSO-d6) δ 8.21 (s, 3H), 2.36-2.23 (m, 1H), 1.58 (s, 6H), 0.80-0.73 (m, 2H), 0.73-0.61 (m, 2H).

tert-Butyl (1-(2-bromothiazol-4-yl)cyclopropyl)carbamate INTE34

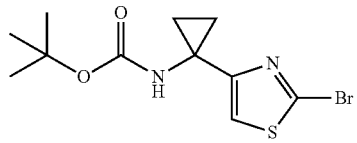 [SMILES: CC(C)(C)OC(=O)NC1(c2csc(Br)n2)CC1]

A suspension of commercial 1-(2-bromothiazol-4-yl)cyclopropanecarboxylic acid (2.95 g, 11.9 mmol) in toluene (30 mL) was treated with t-BuOH (30 mL) and triethylamine (1.8 mL, 12.91 mmol) and then heated to 40° C. whereupon a solution was observed, DPPA (2.7 mL, 11.90 mmol) was then added. The reaction mixture was then heated to 100° C. for 3 hrs then allowed to cool to RT. The reaction mixture was then treated with sat. NaHCO₃ (aq, 100 mL) and EtOAc (100 mL). The phases were separated and the organic phase washed with brine (20 mL), dried over $Na_2SO_4$, filtered and concentrated. The crude product was purified by chromatography on silica gel (40 g column, 0-100% EtOAc/iso-hexane) to afford tert-butyl (1-(2-bromothiazol-4-yl)cyclopropyl)carbamate (1.26 g, 3.55 mmol, 30% yield) as a colourless solid. Rt 1.23 (UPLC acidic); m/z 264 ($^{79}$Br M+H-tBu)$^+$ (ES$^+$); $^1$H NMR (500 MHz, DMSO-d6) δ 7.76 (s, 1H), 7.14 (s, 1H), 1.40 (s, 9H), 1.26-1.21 (m, 2H), 1.12-1.05 (m, 2H).

tert-Butyl (1-(2-bromothiazol-4-yl)-3-methoxypropyl)carbamate INTE35

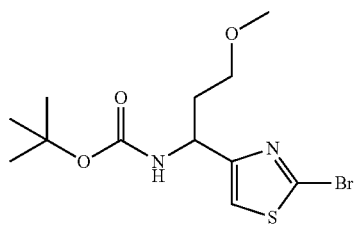 [SMILES: COCCC(NC(=O)OC(C)(C)C)c1csc(Br)n1]

Prepared as for INTE34 using 2-(2-bromothiazol-4-yl)-4-methoxybutanoic acid INTE25 to afford tert-butyl (1-(2-bromothiazol-4-yl)-3-methoxypropyl)carbamate (28% yield) as a colourless solid. Rt 1.38 (UPLC basic); m/z 251 (M+H-tBu)$^+$ (ES$^+$); $^1$H NMR (500 MHz, DMSO-d6) δ 7.37 (s, 1H), 7.32 (d, J=8.7 Hz, 1H), 4.75-4.66 (m, 1H), 3.37-3.24 (m, 2H), 3.20 (s, 3H), 2.05-1.93 (m, 1H), 1.88-1.76 (m, 1H), 1.38 (s, 9H).

tert-Butyl (1-(2-(cyclopropanesulfonamido)thiazol-4-yl)cyclopropyl)carbamate INTE36

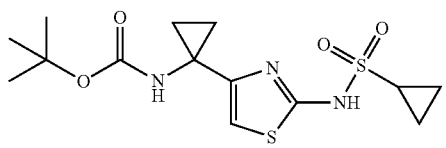 [SMILES: CC(C)(C)OC(=O)NC1(c2csc(NS(=O)(=O)C3CC3)n2)CC1]

A suspension of cyclopropanesulfonamide (500 mg, 4.13 mmol), tert-butyl (1-(2-bromothiazol-4-yl)cyclopropyl)carbamate (1.26 g, 3.95 mmol) INTE34 and $Cs_2CO_3$ (4.0 g, 12.9 mmol) in dioxane (10 mL) was degassed (N₂). To this suspension was added a degassed (N₂) solution of t-BuXPhos (170 mg, 0.40 mmol) and [Pd(allyl)Cl]₂ (75 mg, 0.204 mmol) in dioxane (5 mL). The reaction mixture was stirred at 90° C. for 18 hrs. An additional degassed (N₂) solution of t-BuXPhos (170 mg, 0.400 mmol) and [Pd(allyl)Cl]₂ (75 mg, 0.204 mmol) in dioxane (5 mL) was then added to the reaction mixture and the temperature was maintained at 90° C. for 18 hrs. The reaction mixture was cooled to RT then diluted with EtOAc (100 mL) and acidified with 1M HCl (50 mL). The phases were separated and the organic phase washed with brine (50 mL). The organic phase was dried over $Na_2SO_4$, filtered and concentrated onto silica (5 g). The crude product was purified by chromatography on silica gel (40 g column, 0-100% EtOAc/iso-hexane) to afford tert-butyl (1-(2-(cyclopropanesulfonamido)thiazol-4-yl)cyclopropyl)carbamate (427 mg, 1.13 mmol, 29% yield) as a colourless solid. Rt 1.72 (HPLC acidic); m/z 360 ($^{79}$Br M+H)$^+$ (ES$^+$); $^1$H NMR (500 MHz, DMSO-d6) δ 12.12 (s, 1H), 7.57 (s, 1H), 6.27 (s, 1H), 2.61-2.54 (m, 1H), 1.37 (s, 9H), 1.25-1.19 (m, 2H), 1.09-1.00 (m, 2H), 0.99-0.85 (m, 4H).

tert-Butyl (1-(2-(cyclopropanesulfonamido)thiazol-4-yl)-3-methoxypropyl)carbamate INTE37

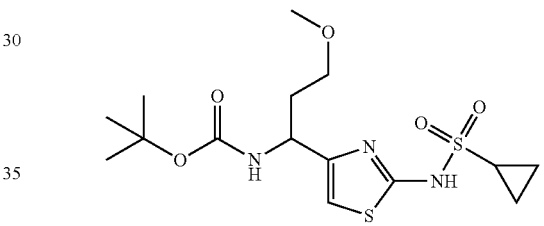

Prepared as for INTE36 using tert-butyl (1-(2-bromothiazol-4-yl)-3-methoxypropyl)carbamate INTE35 to afford tert-butyl (1-(2-(cyclopropanesulfonamido)thiazol-4-yl)-3-methoxypropyl)carbamate (47% yield) as a colourless solid. Rt 1.71 (HPLC acidic); m/z 392 (M+H)$^+$ (ES$^+$); $^1$H NMR (500 MHz, DMSO-d6) δ 12.48 (s, 1H), 7.17 (d, J=8.7 Hz, 1H), 6.43 (s, 1H), 4.57-4.44 (m, 1H), 3.39-3.25 (m, 2H), 3.21 (s, 3H), 2.63-2.55 (m, 1H), 2.00-1.86 (m, 1H), 1.84-1.67 (m, 1H), 1.39 (s, 9H), 0.99-0.81 (m, 4H).

N-(4-(1-Aminocyclopropyl)thiazol-2-yl)cyclopropanesulfonamide, HCl INTE38

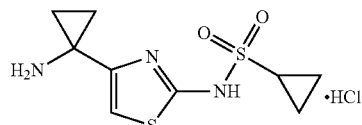

tert-Butyl (1-(2-(cyclopropanesulfonamido)thiazol-4-yl)cyclopropyl)carbamate (427 mg, 1.13 mmol) INTE36 was dissolved in 4M HCl in dioxane (5 mL) then stirred at RT for 1 hr. The reaction mixture was then concentrated in vacuo and the residue azeotroped with toluene (5 mL) then MeCN (2×5 mL) to afford N-(4-(1-aminocyclopropyl)thiazol-2-yl)cyclopropanesulfonamide, HCl (340 mg, 0.92 mmol, 82% yield) as a brown solid. Rt 0.25 (HPLC acidic); m/z 260 (M+H)$^+$ (ES$^+$); $^1$H NMR data not collected.

N-(4-(1-Amino-3-methoxypropyl)thiazol-2-yl)cyclo-propanesulfonamide, HCl INTE39

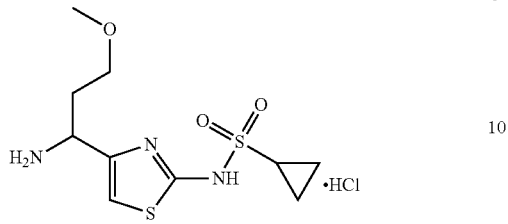

Prepared as for INTE37 using tert-butyl (1-(2-(cyclopropanesulfonamido)thiazol-4-yl)-3-methoxypropyl)carbamate to afford N-(4-(1-amino-3-methoxypropyl)thiazol-2-yl)cyclopropanesulfonamide, HCl (quantitative yield) as a colourless solid. Rt 0.84 (HPLC basic); m/z 292 (M+H)+ (ES+); 1H NMR data not collected.

TABLE 3

The following intermediates were made according to Method 1a or 1b (see preparation of examples section for details).

| INT | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTE18 | 4-Bromo-N-(2-(2-(cyclopropanesulfonamido)thiazol-4-yl)propan-2-yl)-2-methoxybenzamide | Method 1b, Using INTE14, [UPLC acidic], 474 (1.27). | 12.52 (s, 1H), 8.24 (s, 1H), 7.68 (d, J = 8.3 Hz, 1H), 7.40 (d, J = 1.8 Hz, 1H), 7.26 (dd, J = 8.3, 1.8 Hz, 1H), 6.49 (s, 1H), 3.96 (s, 3H), 2.61-2.54 (m, 1H), 1.61 (s, 6H), 0.94-0.84 (m, 4H). |
| INTE19 | N-(2-(2-(Cyclopropanesulfonamido)thiazol-4-yl)propan-2-yl)-4-(4,4,5,5-tetramethyl-1,3,2-dioxaborolan-2-yl)benzamide | Method 1a, Using INTE14, [UPLC acidic], 492 (1.38). | 12.55 (s, 1H), 8.27 (s, 1H), 7.90-7.85 (m, 2H), 7.76-7.71 (m, 2H), 6.46 (s, 1H), 2.60-2.52 (m, 1H), 1.61 (s, 6H), 1.31 (s, 12H), 0.92-0.79 (m, 4H). |

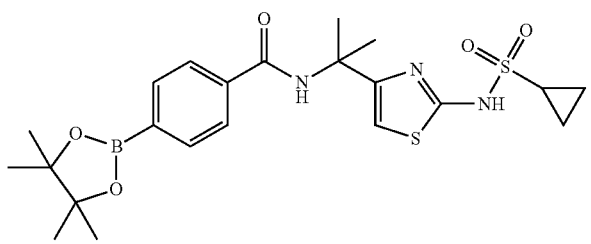 [SMILES: CC(C)(NC(=O)c1ccc(B2OC(C)(C)C(C)(C)O2)cc1)c1csc(NS(=O)(=O)C2CC2)n1]

TABLE 3-continued

The following intermediates were made according to Method 1a or 1b (see preparation of examples section for details).

| INT | Name/Structure (All examples containing chiral centres are racemates unless stated) | Synthesis Method, [LCMS Method], m/z (M + H)+, (Rt/min) | 1H NMR Chemical Shift Data (DMSO-d6 unless stated) |
|---|---|---|---|
| INTE20 | N-(2-(2-(Cyclopropanesulfonamido)thiazol-4-yl)propan-2-yl)-2-fluoro-4-(4,4,5,5-tetramethyl-1,3,2-dioxaborolan-2-yl)benzamide | Method 1a, Using INTE14, [UPLC acidic], 510 (1.44). | 12.57 (s, 1H), 8.35-8.27 (m, 1H), 7.78-7.70 (m, 1H), 7.56-7.50 (m, 1H), 7.43-7.35 (m, 1H), 6.47 (s, 1H), 2.63-2.54 (m, 1H), 1.60 (s, 6H), 1.31 (s, 12H), 0.93-0.82 (m, 4H). |

Synthesis of Biaryl Acids and their Intermediates

2-Ethoxy-6-(4,4,5,5-tetramethyl-1,3,2-dioxaborolan-2-yl)pyrazine INTF1

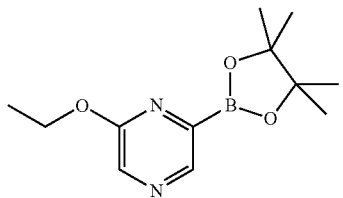 [SMILES: CCOc1cncc(B2OC(C)(C)C(C)(C)O2)n1]

To a solution of 2-chloro-6-ethoxypyrazine (10.0 g, 59.9 mmol) in dioxane (200 mL) was successively added bispin (16.7 g, 65.9 mmol), KOAc (23.5 g, 240 mmol) and PdCl2(dppf)-CH2Cl2 (2.45 g, 3.00 mmol) at RT. The resulting mixture was degassed (N2) before heating at 110° C. for 2.5 hrs. The mixture was cooled to RT, filtered through celite and the solvent was removed in vacuo. The crude product was purified by chromatography on silica (220 g cartridge, 20-100% EtOAc/iso-hexanes). The crude product was then dissolved in EtOAc (20 mL) and washed with water (3×10 mL). The organic layer was dried (Na2SO4), filtered and the solvent was removed in vacuo. The product was re-purified by chromatography on silica (330 g cartridge, 0-100% EtOAc/iso-hexanes) and the product was dissolved in EtOAc (50 mL) and washed with water (4×30 mL). The organic layer was dried (Na2SO4), filtered and concentrated in vacuo to afford 2-ethoxy-6-(4,4,5,5-tetramethyl-1,3,2-dioxaborolan-2-yl)pyrazine (2.0 g, 7.60 mmol, 13% yield) as a thick pale yellow oil. 1H NMR (500 MHz, DMSO-d6) δ 8.38 (s, 1H), 8.30 (s, 1H), 4.36 (q, J=7.1 Hz, 2H), 1.34 (t, J=7.1 Hz, 3H), 1.32 (s, 12H).

Methyl 4-(6-ethoxypyrazin-2-yl)-2-methylbenzoate INTF2

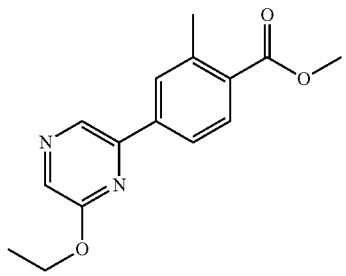 [SMILES: CCOc1cncc(-c2ccc(C(=O)OC)c(C)c2)n1]

A solution of 2-ethoxy-6-(4,4,5,5-tetramethyl-1,3,2-dioxaborolan-2-yl)pyrazine INTF1 (200 mg, 0.80 mmol), methyl 4-bromo-2-methylbenzoate (183 mg, 0.80 mmol) and Cs2CO3 (700 mg, 2.15 mmol) in a mixture of dioxane (5 mL) and water (1 mL) at 35° C. was degassed (N2) then PdCl2(dppf)-CH2Cl2 (35 mg, 0.043 mmol) was added. The mixture was degassed (N2) then heated to 90° C. for 18 hrs. The reaction mixture was concentrated (to approx. 2 mL) then taken up with water (5 mL) and EtOAc (10 mL) and filtered through celite, eluting with EtOAc (20 mL).

The phases were then diluted with water (10 mL) and partitioned. The organic phase was washed with brine (10 mL), dried (Na2SO4), filtered and concentrated onto silica (1 g). The crude product was purified by chromatography on silica (40 g cartridge, 0-30% EtOAc/iso-hexanes to afford methyl 4-(6-ethoxypyrazin-2-yl)-2-methylbenzoate (124 mg, 0.45 mmol, 56% yield) as a colourless solid. Rt 2.54 min (HPLC, acidic); m/z 273 (M+H)+ (ES+); 1H NMR (500 MHz, DMSO-d6) δ 8.88 (s, 1H), 8.29 (s, 1H), 8.11-8.08 (m, 1H), 8.05 (dd, J=8.2, 1.8 Hz, 1H), 7.95 (d, J=8.2 Hz, 1H), 4.49 (q, J=7.0 Hz, 2H), 3.86 (s, 3H), 2.61 (s, 3H), 1.41 (t, J=7.0 Hz, 3H).

Methyl 2-fluoro-4-(6-vinylpyrazin-2-yl)benzoate
INTF3

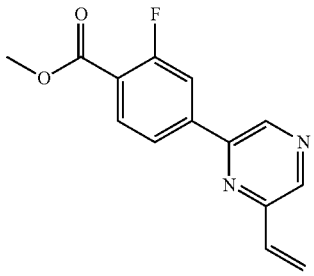 [SMILES: C=Cc1cncc(-c2ccc(C(=O)OC)c(F)c2)n1]

A stirred solution of potassium trifluoro(vinyl)borate (900 mg, 6.72 mmol), 2,6-dichloropyrazine (1 g, 6.71 mmol) and 2 M $K_2CO_3$ (10 mL, 20.0 mmol) in dioxane (80 mL) at 40° C. was degassed ($N_2$) then treated with $PdCl_2(dppf)\cdot CH_2Cl_2$ (274 mg, 0.336 mmol), degassed ($N_2$), then heated to 80° C. for 4 hrs. The reaction mixture was cooled to RT then (3-fluoro-4-(methoxycarbonyl)phenyl)boronic acid (1.33 g, 6.71 mmol) was added and the reaction mixture was heated to 100° C. for 18 hrs. The reaction mixture was cooled and concentrated (to approx. 10 mL). 1 M HCl (100 mL) and EtOAc (100 mL) were added and the reaction mixture was filtered through celite, further eluting with EtOAc (50 mL). The phases were partitioned and the organic phase was washed with brine (50 mL). The organic phase was dried ($MgSO_4$), filtered and concentrated onto silica (5 g). The crude product was purified by chromatography on silica (40 g cartridge, 0-50% EtOAc/iso-hexanes) to afford methyl 2-fluoro-4-(6-vinylpyrazin-2-yl)benzoate (490 mg, 1.803 mmol, 27% yield) as a brown gum. Rt 2.24 min (HPLC, acidic); m/z 259 $(M+H)^+$ $(ES^+)$; $^1H$ NMR (500 MHz, DMSO-$d_6$) δ 9.27 (s, 1H), 8.83 (s, 1H), 8.19 (d, J=1.0 Hz, 1H), 8.18-8.15 (m, 1H), 8.08-7.99 (m, 1H), 6.98 (dd, J=17.5, 10.9 Hz, 1H), 6.56 (dd, J=17.5, 1.3 Hz, 1H), 5.74 (dd, J=10.9, 1.4 Hz, 1H), 3.90 (s, 3H).

Methyl 4-(6-ethylpyrazin-2-yl)-2-fluorobenzoate
INTF4

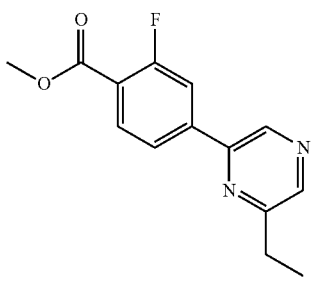 [SMILES: CCc1cncc(-c2ccc(C(=O)OC)c(F)c2)n1]

A solution of methyl 2-fluoro-4-(6-vinylpyrazin-2-yl)benzoate INTF3 (490 mg, 1.88 mmol) in MeOH (10 mL) was prepared. The reaction mixture was hydrogenated in the H-Cube (10% Pd/C, 30×4 mm, full hydrogen, 35° C., 1 mL/min). The reaction mixture was concentrated to afford methyl 4-(6-ethylpyrazin-2-yl)-2-fluorobenzoate (470 mg; 1.77 mmol; 93% yield); Rt 2.27 min (HPLC, acidic); m/z 261 $(M+H)^+$ $(ES^+)$; $^1H$ NMR (500 MHz, DMSO-$d_6$) δ 9.20 (s, 1H), 8.63 (s, 1H), 8.15-8.09 (m, 2H), 8.07-8.00 (m, 1H), 3.89 (s, 3H), 2.89 (q, J=7.6 Hz, 2H), 1.32 (t, J=7.6 Hz, 3H).

Method C: Suzuki Coupling

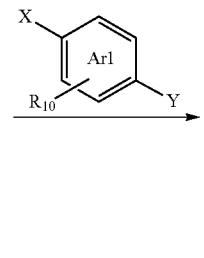

Z = Br, Cl
X = B(OH)$_2$, B(pin)$_2$

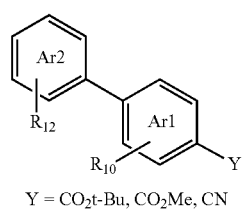

Y = CO$_2$t-Bu, CO$_2$Me, CN

A solution of boronic acid (1 eq), aryl halide (1.05 eq.) and $Cs_2CO_3$ (3 eq.) in a mixture of dioxane (40 volumes) and water (6 volumes) was degassed ($N_2$, 5 mins). $PdCl_2$(dppf)·$CH_2Cl_2$ (5 mol %) was added and the reaction was further degassed ($N_2$) before being heated to 90° C. for 18 hrs. The reaction mixture was filtered through celite before an aqueous workup was undertaken, followed by purification by normal phase chromatography.

TABLE 4

The following intermediates were made according to Method C.

| INT | Name/Structure | Synthesis Method, [LCMS Method], m/z (M + H)+, (Rt/min) | 1H NMR Chemical Shift Data (DMSO-d6 unless stated) |
|---|---|---|---|
| INTF5 | tert-butyl 4-(5-methylpyridin-3-yl)benzoate | Using Ar2Br, [HPLC acidic], 270 (1.93). | 8.75 (d, J = 2.2 Hz, 1H), 8.51-8.39 (m, 1H), 8.03-7.98 (m, 3H), 7.88-7.82 (m, 2H), 2.4 (s, 3H), 1.57 (s, 9H). |
| INTF6 | tert-butyl 4-(5-(trifluoromethyl)pyridin-3-yl)benzoate | Using Ar2Br, [HPLC acidic], 324 (2.78). | 9.27 (d, J = 2.2 Hz, 1H), 9.03 (dd, J = 2.2, 1.0 Hz, 1H), 8.61-8.41 (m, 1H), 8.22-7.83 (m, 4H), 1.58 (s, 9H). |
| INTF7 | tert-butyl 4-(5-fluoropyridin-3-yl)benzoate | Using Ar2Br, [HPLC acidic], 274 (2.56). | 8.87 (d, J = 1.9 Hz, 1H), 8.64 (d, J = 2.7 Hz, 1H), 8.22-8.09 (m, 1H), 8.06-7.98 (m, 2H), 7.98-7.89 (m, 2H), 1.57 (s, 9H). |
| INTF8 | tert-butyl 4-(6-chloropyrazin-2-yl)benzoate | Using Ar2Cl, [UPLC acidic], 290 35Cl isotope, (1.53). | No 1H NMR recorded. |
| INTF9 | tert-butyl 4-(6-(trifluoromethyl)pyrazin-2-yl)benzoate | Using Ar2Cl, [HPLC acidic], no ionisation (2.83). | 9.70 (s, 1H), 9.23 (s, 1H), 8.40-8.30 (m, 2H), 8.12-8.03 (m, 2H), 1.59 (s, 9H). |

TABLE 4-continued

The following intermediates were made according to Method C.

| INT | Name/Structure | Synthesis Method, [LCMS Method], m/z (M + H)+, (Rt/min) | $^1$H NMR Chemical Shift Data (DMSO-$d_6$ unless stated) |
|---|---|---|---|
| INTF10 | tert-butyl 4-(6-methylpyrazin-2-yl)benzoate | Using Ar2Cl, [HPLC acidic], 271 (2.54). | 9.24-9.02 (m, 1H), 8.57 (s, 1H), 8.44-8.14 (m, 2H), 8.14-7.68 (m, 2H), 2.63-2.52 (m, 3H), 1.57 (s, 9H). |
| INTF11 | tert-butyl 4-(6-isopropoxypyrazin-2-yl)benzoate | Using Ar2Cl, [UPLC acidic], 315 (1.97). | 8.86 (s, 1H), 8.30-8.21 (m, 3H), 8.06-8.02 (m, 2H), 5.41 (hept, J = 6.2 Hz, 1H), 1.58 (s, 9H), 1.40 (d, J = 6.2 Hz, 6H). |
| INTF12 | methyl 4-(5-chloropyridin-3-yl)benzoate | Using Ar2Cl, [HPLC acidic], 247 $^{35}$Cl isotope, (2.20). | 8.94 (d, J = 2.0 Hz, 1H), 8.69 (d, J = 2.2 Hz, 1H), 8.35 (t, J = 2.2 Hz, 1H), 8.10-8.01 (m, 2H), 8.00-7.89 (m, 2H), 3.89 (s, 3H). |
| INTF13 | methyl 2-fluoro-4-(5-(trifluoromethyl)pyridin-3-yl)benzoate | Using Ar2Cl [HPLC acidic], 300 (2.30). | No $^1$H NMR recorded. |
| INTF14 | methyl 4-(5-chloropyridin-3-yl)-2-fluorobenzoate | Using Ar2Br [HPLC acidic], 266 $^{35}$Cl isotope (2.20). | No $^1$H NMR recorded. |

TABLE 4-continued

The following intermediates were made according to Method C.

| INT | Name/Structure | Synthesis Method, [LCMS Method], m/z (M + H)+, (Rt/min) | $^1$H NMR Chemical Shift Data (DMSO-$d_6$ unless stated) |
|---|---|---|---|
| INTF15 | methyl 2-fluoro-4-(6-(trifluoromethyl)pyrazin-2-yl)benzoate | Using Ar2Cl, [UPLC acidic], 301 (1.53). | 9.73 (s, 1H), 9.25 (s, 1H), 8.23-8.13 (m, 2H), 8.09 (dd, J = 8.5, 7.5 Hz, 1H), 3.90 (s, 3H). |
| INTF16 | methyl 4-(6-ethoxypyrazin-2-yl)-2-fluorobenzoate | Using Ar2Cl, [UPLC acidic], 277 (1.53). | 8.94 (s, 1H), 8.34 (s, 1H), 8.12-8.08 (m, 2H), 8.04-8.00 (m, 1H), 4.50 (q, J = 7.0 Hz, 2H), 3.89 (s, 3H), 1.41 (t, J = 7.0 Hz, 3H). |
| INTF17 | methyl 2-fluoro-4-(6-isopropoxypyrazin-2-yl)benzoate | Using Ar2Cl, [UPLC acidic], 291 (1.63). | 8.91 (s, 1H), 8.28 (s, 1H), 8.13-7.94 (m, 3H), 5.43 (hept, J = 6.1 Hz, 1H), 3.89 (s, 3H), 1.39 (d, J = 6.2 Hz, 6H). |
| INTF18 | tert-butyl 4-(6-ethoxypyrazin-2-yl)benzoate | Using Ar2Cl, [HPLC acidic], 301 (2.89). | 8.87 (s, 1H), 8.30 (s, 1H), 8.26-8.22 (m, 2H), 8.06-7.98 (m, 2H), 4.48 (q, J = 7.1 Hz, 2H), 1.57 (s, 9H), 1.40 (t, J = 7.0 Hz, 3H). |
| INTF19 | methyl 2-fluoro-4-(6-(2,2,2-trifluoroethoxy)pyrazin-2-yl)benzoate | Using Ar2Cl, [HPLC acidic], 331 (2.44). | 9.11 (s, 1H), 8.56 (s, 1H), 8.23 (dd, J = 12.3, 1.7 Hz, 1H), 8.18 (dd, J = 8.2, 1.7 Hz, 1H), 8.06-8.01 (m, 1H), 5.24 (q, J = 9.0 Hz, 2H), 3.90 (s, 3H). |

TABLE 4-continued

The following intermediates were made according to Method C.

| INT | Name/Structure | Synthesis Method, [LCMS Method], m/z (M + H)⁺, (Rt/min) | $^1$H NMR Chemical Shift Data (DMSO-$d_6$ unless stated) |
|---|---|---|---|
| INTF20 | tert-butyl 4-(6-(2,2,2-trifluoroethoxy)pyrazin-2-yl)benzoate | Using Ar2Cl, [UPLC acidic], 355 (2.88) | 9.06 (s, 1H), 8.52 (s, 1H), 8.44-8.24 (m, 2H), 8.06-8.01 (m, 2H), 5.22 (q, J = 9.0 Hz, 2H), 1.58 (s, 9H). |
| INTF21 | methyl 4-(6-ethoxypyrazin-2-yl)-2-(trifluoromethyl)benzoate | Using Ar2Cl, [UPLC acidic], 327 (2.59) | 9.01 (d, J = 1.6 Hz, 1H), 8.56-8.52 (m, 2H), 8.37 (d, J = 1.6 Hz, 1H), 8.01 (d, J = 8.4 Hz, 1H), 4.58-4.41 (m, 2H), 3.91 (s, 3H), 1.42 (t, J = 7.0 Hz, 3H). |
| INTF22 | methyl 2-methyl-4-(6-(trifluoromethyl)pyrazin-2-yl)benzoate | Using Ar2Cl, [UPLC acidic], 297 (1.62) | 9.69 (s, 1H), 9.21 (s, 1H), 8.19 (d, J = 1.8 Hz, 1H), 8.14 (dd, J = 8.2, 1.8 Hz, 1H), 8.01 (d, J = 8.2 Hz, 1H), 3.88 (s, 3H), 2.64 (s, 3H). |
| INTF23 | 5-(6-ethoxypyrazin-2-yl)-3-fluoropicolinonitrile | Using Ar2Cl, [HPLC acidic], 245 (2.17) | 9.38 (t, J = 1.6 Hz, 1H), 9.05 (s, 1H), 8.76 (dd, J = 10.2, 1.6 Hz, 1H), 8.43 (s, 1H), 4.53 (q, J = 7.0 Hz, 2H), 1.41 (t, J = 7.0 Hz, 3H). |

Method D: Ester Deprotection with TFA

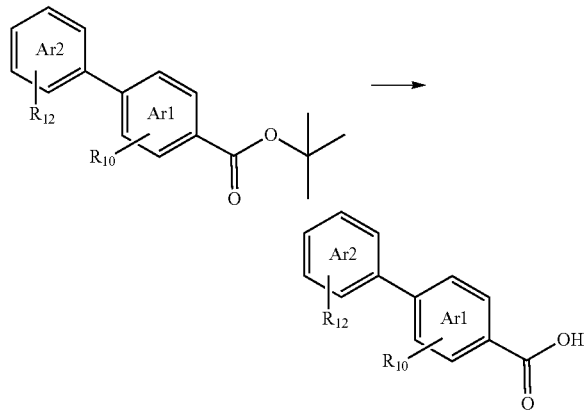

A solution of the ester (1 eq) in DCM (20 volumes) was treated with TFA (10 eq.) and stirred at RT for 3 hrs. The reaction mixture was then concentrated and azeotroped with MeOH and MeCN. No further purification was undertaken.

Method E: Ester Deprotection with Base

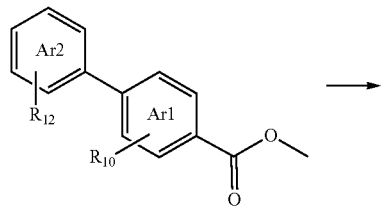

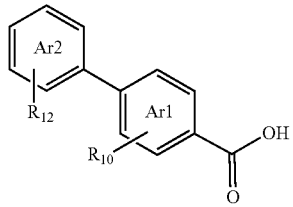

A solution of the ester (1 eq) in a mixture of THF/MeOH (4/1 volumes) was treated with LiOH (2.2-6 eq.) and stirred between RT and 50° C. for between 3 hrs and 18 hrs. The organic solvents were removed in vacuo then acidified with 1 M HCl and extracted with EtOAc. The organic phases were combined, dried ($Na_2SO_4$), filtered and concentrated. The products were used directly in the next step with no further purification undertaken.

Method F: Potassium Salt Formation

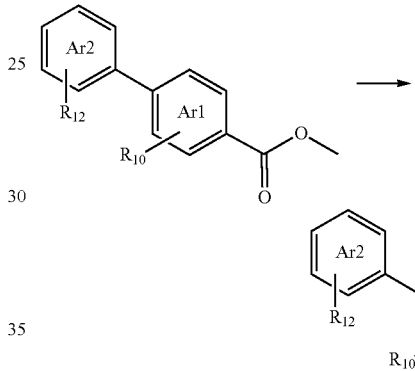

A solution of the ester (1 eq.) in THF (4 volumes) was treated with TMSOK (1 eq.) and stirred at RT for 2 hrs before the reaction mixtures were filtered and washed with iso-hexanes. The products were used directly in the next step with no further purification undertaken.

TABLE 5

The following intermediates were made according to Method D, E or F.

| INT | Name/Structure | Synthesis Method, [LCMS Method], m/z (M + H)$^+$, (Rt/min) | $^1$H NMR Chemical Shift Data (DMSO-d$_6$ unless stated) |
|---|---|---|---|
| INTF24 | 4-(5-methylpyridin-3-yl)benzoic acid 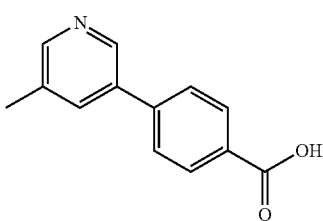 [SMILES: Cc1cncc(-c2ccc(C(=O)O)cc2)c1] | Method D, Using INTF5, [HPLC acidic], 214 (0.95). | 9.02-8.94 (m, 1H), 8.70-8.63 (m, 1H), 8.47 (s, 1H), 8.14-8.06 (m, 2H), 8.00-7.90 (m, 2H), 2.49 (s, 3H), O—H not observed. |

TABLE 5-continued

The following intermediates were made according to Method D, E or F.

| INT | Name/Structure | Synthesis Method, [LCMS Method], m/z (M + H)+, (Rt/min) | 1H NMR Chemical Shift Data (DMSO-d6 unless stated) |
| --- | --- | --- | --- |
| INTF25 | 4-(5-(trifluoromethyl)pyridin-3-yl)benzoic acid | Method D, Using INTF6, [HPLC acidic], 268 (2.01). | 13.12 (s, 1H), 9.28 (d, J = 2.2 Hz, 1H), 9.03 (dd, J = 2.2, 1.0 Hz, 1H), 8.56 (d, J = 2.2 Hz, 1H), 8.13-8.04 (m, 2H), 8.04-7.86 (m, 2H). |
| INTF26 | 4-(5-fluoropyridin-3-yl)benzoic acid | Method D, Using INTF7, [HPLC acidic], 218 (1.67). | 8.87 (t, J = 1.8 Hz, 1H), 8.64 (d, J = 2.7 Hz, 1H), 8.17 (ddd, J = 10.3, 2.7, 1.8 Hz, 1H), 8.07-8.03 (m, 2H), 7.97-7.90 (m, 2H), OH not observed. |
| INTF27 | 4-(6-chloropyrazin-2-yl)benzoic acid | Method D, Using INTF8, [HPLC acidic], 234 35Cl isotope, (1.91). | No NMR recorded. |
| INTF28 | 4-(6-(trifluoromethyl)pyrazin-2-yl)benzoic acid | Method D, Using INTF9, [UPLC acidic], 269 (1.33). | 13.25 (s, 1H), 9.70 (s, 1H), 9.23 (s, 1H), 8.42-8.20 (m, 2H), 8.20-8.00 (m, 2H). |
| INTF29 | 4-(6-methylpyrazin-2-yl)benzoic acid | Method D, Using INTF10, [HPLC acidic], 215 (1.60). | 9.13 (s, 1H), 8.57 (s, 1H), 8.31-8.23 (m, 2H), 8.09-8.04 (m, 2H), 2.59 (s, 3H), OH not observed. |

TABLE 5-continued

The following intermediates were made according to Method D, E or F.

| INT | Name/Structure | Synthesis Method, [LCMS Method], m/z (M + H)+, (Rt/min) | 1H NMR Chemical Shift Data (DMSO-d6 unless stated) |
|---|---|---|---|
| INTF30 | 4-(6-isopropoxypyrazin-2-yl)benzoic acid | Method D, Using INTF11, [UPLC acidic], 259 (1.40). | 13.13 (s, 1H) 8.87 (s, 1H), 8.27-8.20 (m, 3H), 8.09-8.05 (m, 2H), 5.43 (p, J = 6.2 Hz, 1H), 1.40 (d, J = 6.2 Hz, 6H). |
| INTF31 | potassium 4-(5-chloropyridin-3-yl)benzoate | Method F, Using INTF12, [UPLC acidic], 234 35Cl isotope, ionises as free acid, (1.18). | 8.87 (d, J = 2.0 Hz, 1H), 8.59 (d, J = 2.2 Hz, 1H), 8.23 (t, J = 2.2 Hz, 1H), 7.95-7.86 (m, 2H), 7.72-7.55 (m, 2H). |
| INTF32 | potassium 2-fluoro-4-(5-(trifluoromethyl)pyridin-3-yl)benzoate | Method F, Using INTF13, [HPLC acidic], 286 ionises as free acid, (2.01). | 9.22 (d, J = 2.2 Hz, 1H), 8.95 (d, J = 2.1 Hz, 1H), 8.48 (d, J = 2.3 Hz, 1H), 7.64-7.45 (m, 3H). |
| INTF33 | potassium 4-(5-chloropyridin-3-yl)-2-fluorobenzoate | Method F, Using INTF14, [HPLC acidic], 251 35Cl isotope, ionises as free acid, (1.88). | 8.91-8.85 (m, 1H), 8.63-8.54 (m, 1H), 8.30-8.20 (m, 1H), 7.59-7.49 (m, 1H), 7.49-7.34 (m, 2H). |
| INTF34 | 2-fluoro-4-(6-(trifluoromethyl)pyrazin-2-yl)benzoic acid | Method E, Using INTF15, [HPLC acidic], 287 (2.08). | 13.53 (s, 1H), 9.72 (s, 1H), 9.25 (s, 1H), 8.19-8.12 (m, 2H), 8.11-7.99 (m, 1H). |

TABLE 5-continued

The following intermediates were made according to Method D, E or F.

| INT | Name/Structure | Synthesis Method, [LCMS Method], m/z (M + H)+, (Rt/min) | 1H NMR Chemical Shift Data (DMSO-d6 unless stated) |
|---|---|---|---|
| INTF35 | 4-(6-ethoxypyrazin-2-yl)-2-fluorobenzoic acid | Method E, Using INTF16, [HPLC acidic], 263 (2.07). | 13.40 (s, 1H), 8.94 (s, 1H), 8.34 (s, 1H), 8.12-8.03 (m, 2H), 8.03-7.92 (m, 1H), 4.50 (q, J = 7.0 Hz, 2H), 1.41 (t, J = 7.0 Hz, 3H). |
| INTF36 | 2-fluoro-4-(6-isopropoxypyrazin-2-yl)benzoic acid | Method E, Using INTF17, [HPLC acidic], 277 (2.24). | 13.53 (s, 1H), 8.90 (s, 1H), 8.27 (s, 1H), 8.08-7.87 (m, 3H), 5.43 (hept, J = 6.2 Hz, 1H), 1.39 (d, J = 6.2 Hz, 6H). |
| INTF37 | 4-(6-ethoxypyrazin-2-yl)benzoic acid | Method D, Using INTF18, [UPLC acidic], 245 (1.29) | 13.15 (v. br. s, 1H), 8.89 (s, 1H), 8.31 (s, 1H), 8.29-8.22 (m, 2H), 8.11-8.01 (m, 2H), 4.51 (q, J = 7.0 Hz, 2H), 1.42 (t, J = 7.0 Hz, 3H). |
| INTF38 | 4-(6-ethoxypyrazin-2-yl)-2-methylbenzoic acid | Method E, Using INTF2, [HPLC acidic], 259 (2.17) | 12.97 (s, 1H), 8.87 (s, 1H), 8.29 (s, 1H), 8.07-8.05 (m, 1H), 8.03 (dd, J = 8.2, 1.9 Hz, 1H), 7.94 (d, J = 8.2 Hz, 1H), 4.49 (q, J = 7.0 Hz, 2H), 2.62 (s, 3H), 1.41 (t, J = 7.0 Hz, 3H). |
| INTF39 | 4-(6-ethylpyrazin-2-yl)-2-fluorobenzoic acid | Method E, Using INTF4, [HPLC acidic], 247 (1.91) | 13.40 (s, 1H), 9.19 (s, 1H), 8.63 (s, 1H), 8.13-8.05 (m, 2H), 8.01 (t, J = 7.9 Hz, 1H), 2.89 (q, J = 7.6 Hz, 2H), 1.32 (t, J = 7.6 Hz, 3H). |

TABLE 5-continued

The following intermediates were made according to Method D, E or F.

| INT | Name/Structure | Synthesis Method, [LCMS Method], m/z (M + H)+, (Rt/min) | 1H NMR Chemical Shift Data (DMSO-d6 unless stated) |
|---|---|---|---|
| INTF40 | 2-fluoro-4-(6-(2,2,2-trifluoro ethoxy)pyrazin-2-yl)benzoic acid | Method E, Using INTF19, [UPLC acidic], 317 (1.38) | 13.44 (s, 1H), 9.10 (s, 1H), 8.55 (s, 1H), 8.23-8.12 (m, 2H), 8.03-7.95 (m, 1H), 5.24 (q, J = 9.0 Hz, 2H). |
| INTF41 | 4-(6-(2,2,2-trifluoroethoxy)pyrazin-2-yl)benzoic acid | Method D, Using INTF20 [UPLC acidic], 299 (1.37) | 13.16 (s, 1H), 9.06 (s, 1H), 8.52 (s, 1H), 8.41-8.27 (m, 2H), 8.13-8.03 (m, 2H), 5.22 (q, J = 9.0 Hz, 2H). |
| INTF42 | 4-(6-ethoxypyrazin-2-yl)-2-(trifluoromethyl)benzoic acid | Method E, Using INTF21, [UPLC acidic], 313 (2.30) | 13.75 (s, 1H), 8.98 (s, 1H), 8.52-8.46 (m, 2H), 8.35 (s, 1H), 7.97 (d, J = 7.9 Hz, 1H), 4.49 (q, J = 7.0 Hz, 2H), 1.42 (t, J = 7.0 Hz, 3H). |
| INTF43 | 2-methyl-4-(6-(trifluoromethyl) pyrazin-2-yl)benzoic acid | Method E, Using INTF22, [HPLC acidic], 283 (2.20) | 13.06 (s, 1H), 9.66 (s, 1H), 9.18 (s, 1H), 8.14-8.11 (m, 1H), 8.09 (dd, J = 8.1, 1.9 Hz, 1H), 7.99 (d, J = 8.1 Hz, 1H), 2.63 (s, 3H). |

5-(6-Ethoxypyrazin-2-yl)-3-fluoropicolinic acid INTF44

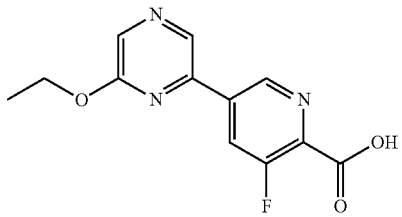 [SMILES: CCOc1cncc(-c2cnc(C(=O)O)c(F)c2)n1]

A suspension of 5-(6-ethoxypyrazin-2-yl)-3-fluoropicolinonitrile INTF23 (630 mg, 2.58 mmol) in conc. HCl (10 mL) was heated to reflux for 1 hr. The reaction mixture was allowed to cool to RT. This was then concentrated in vacuo, then suspended in TBME (20 mL) and filtered, washing with iso-hexanes (10 mL) to afford 5-(6-ethoxypyrazin-2-yl)-3-fluoropicolinic acid (750 mg, 2.28 mmol, 88% yield) as an orange solid. Rt 1.74 min (HPLC, acidic); m/z 264 (M+H)$^+$ (ES$^+$); $^1$H NMR (500 MHz, DMSO-d$_6$) δ 9.26 (t, J=1.6 Hz, 1H), 9.02 (s, 1H), 8.54 (dd, J=11.5, 1.6 Hz, 1H), 8.39 (s, 1H), 4.52 (q, J=7.0 Hz, 2H), 1.41 (t, J=7.0 Hz, 3H), O-H not observed.

(5-(6-(Trifluoromethyl)pyrazin-2-yl)pyridin-2-yl)methanol INTF45

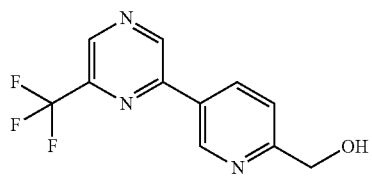 [SMILES: OCc1ccc(-c2cncc(C(F)(F)F)n2)cn1]

A suspension of (5-bromopyridin-2-yl)methanol (1 g, 5.32 mmol), Bispin (1.5 g, 5.91 mmol) and KOAc (1.6 g, 16.0 mmol) in dioxane (20 mL) was heated to 30° C. then degassed (N$_2$). PdCl$_2$(dppf)-CH$_2$Cl$_2$ (0.217 g, 0.266 mmol) was added and the reaction mixture heated to 90° C. for 2 hrs. The reaction mixture was cooled to 40° C. whereupon 2-chloro-6-(trifluoromethyl)pyrazine (0.97 g, 5.32 mmol), Cs$_2$CO$_3$ (3.47 g, 10.6 mmol) and water (5 mL) were added. The mixture was degassed (N$_2$), then PdCl$_2$(dppf)-CH$_2$Cl$_2$ (0.217 g, 0.266 mmol) was added and the mixture was again degassed (N$_2$). The reaction mixture was then heated to 90° C. for 18 hrs. The reaction mixture was part concentrated (to approx. 5 mL) then taken up with water (20 mL) and EtOAc (50 mL) and passed through celite, eluting with EtOAc (20 mL). The phases were then diluted with water (20 mL) and partitioned. The organic phase was washed with brine (30 mL), dried (Na$_2$SO$_4$), filtered and concentrated onto silica (5 g). The crude product was purified by chromatography on silica (40 g cartridge, 0-100% EtOAc/iso-hexanes) to afford (5-(6-(trifluoromethyl)pyrazin-2-yl)pyridin-2-yl)methanol (980 mg, 3.76 mmol, 71% yield) as an off-white solid. Rt 1.38 min (HPLC, acidic); m/z 256 (M+H)$^+$ (ES$^+$); $^1$H NMR (500 MHz, DMSO-d$_6$) δ 9.69 (s, 1H), 9.28 (d, J=2.3 Hz, 1H), 9.20 (s, 1H), 8.56 (dd, J=8.2, 2.3 Hz, 1H), 7.70 (d, J=8.2 Hz, 1H), 5.59 (t, J=5.8 Hz, 1H), 4.67 (d, J=5.8 Hz, 2H).

(5-(6-Chloropyrazin-2-yl)pyridin-2-yl)methanol INTF46

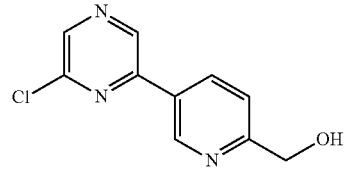 [SMILES: OCc1ccc(-c2cncc(Cl)n2)cn1]

Prepared as for INTF45 using (5-bromopyridin-2-yl)methanol and 2,6-dichloropyrazine to afford (5-(6-chloropyrazin-2-yl)pyridin-2-yl)methanol (27% yield) as a brown solid. Rt 1.10 min (HPLC, acidic); m/z 222 ($^{35}$Cl M+H)$^+$ (ES$^+$); $^1$H NMR (500 MHz, DMSO-d$_6$) δ 9.36 (s, 1H), 9.22 (s, 1H), 8.81 (s, 1H), 8.50 (d, J=8.2 Hz, 1H), 7.66 (d, J=8.2 Hz, 1H), 5.57 (t, J=6.0 Hz, 1H), 4.66 (d, J=6.0 Hz, 2H).

(5-(6-Ethoxypyrazin-2-yl)pyridin-2-yl)methanol INTF47

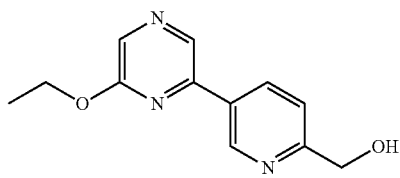 [SMILES: CCOc1cncc(-c2ccc(CO)nc2)n1]

Prepared as for INTF45 using (5-bromopyridin-2-yl)methanol and 2-chloro-6-ethoxypyrazine to afford (5-(6-ethoxypyrazin-2-yl)pyridin-2-yl)methanol (54% yield) as a brown solid. Rt 1.34 min (HPLC, acidic); m/z 232 (M+H)$^+$ (ES$^+$); $^1$H NMR (500 MHz, DMSO-d$_6$) δ 9.27-9.09 (m, 1H), 8.87 (s, 1H), 8.49 (dd, J=8.2, 2.3 Hz, 1H), 8.29 (s, 1H), 7.62 (d, J=8.2 Hz, 1H), 5.53 (t, J=5.9 Hz, 1H), 4.64 (d, J=5.9 Hz, 2H), 4.50 (q, J=7.1 Hz, 2H), 1.41 (t, J=7.1 Hz, 3H).

5-(6-(Trifluoromethyl)pyrazin-2-yl)picolinaldehyde INTF48

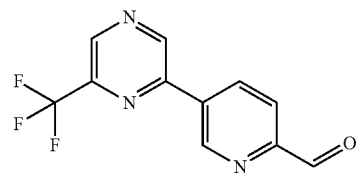 [SMILES: O=Cc1ccc(-c2cncc(C(F)(F)F)n2)cn1]

A solution of (5-(6-(trifluoromethyl)pyrazin-2-yl)pyridin-2-yl)methanol INTF45 (980 mg, 3.84 mmol) in CH$_2$Cl$_2$ (15 mL) was treated with manganese dioxide (3 g, 34.5 mmol). The reaction was stirred for 4 hrs at RT then filtered through celite and concentrated onto silica (4 g). The crude product was purified by chromatography on silica (24 g cartridge, 0-100% EtOAc/iso-hexanes) to afford 5-(6-(trifluoromethyl) pyrazin-2-yl)picolinaldehyde (541 mg, 2.04 mmol, 55% yield) as a colourless solid. Rt 1.82 min (HPLC, acidic); m/z 254 (M+H)$^+$ (ES$^+$); $^1$H NMR (500 MHz, DMSO-d$_6$) δ 10.09

(s, 1H), 9.82 (s, 1H), 9.60 (dd, J=2.2, 0.8 Hz, 1H), 9.30 (s, 1H), 8.79 (dd, J=8.1, 2.2 Hz, 1H), 8.14 (dd, J=8.1, 0.8 Hz, 1H).

5-(6-Chloropyrazin-2-yl)picolinaldehyde INTF49

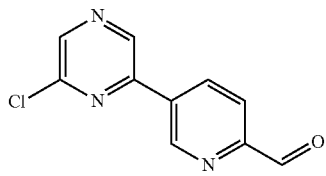 [SMILES: O=Cc1ccc(-c2cncc(Cl)n2)cn1]

Prepared as for INTF48 using (5-(6-chloropyrazin-2-yl)pyridin-2-yl)methanol INTF46 to afford 5-(6-chloropyrazin-2-yl)picolinaldehyde (39% yield) as a colourless solid. Rt 1.63 min (HPLC, acidic); m/z 220 ($^{35}$Cl M+H)$^+$ (ES$^+$); $^1$H NMR (500 MHz, DMSO-d$_6$) δ 10.08 (d, J=0.8 Hz, 1H), 9.55 (dd, J=2.2, 0.9 Hz, 1H), 9.50 (s, 1H), 8.92 (s, 1H), 8.74 (ddd, J=8.1, 2.2, 0.9 Hz, 1H), 8.11 (dd, J=8.1, 0.9 Hz, 1H).

5-(6-Ethoxypyrazin-2-yl)picolinaldehyde INTF50

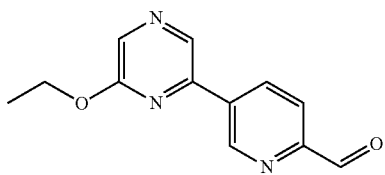 [SMILES: CCOc1cncc(-c2ccc(C=O)nc2)n1]

Prepared as for INTF48 using (5-(6-ethoxypyrazin-2-yl)pyridin-2-yl)methanol INTF47 to afford 5-(6-ethoxypyrazin-2-yl)picolinaldehyde (42% yield) as a colourless solid. Rt 1.85 min (HPLC, acidic); m/z 230 (M+H)$^+$ (ES$^+$); $^1$H NMR (500 MHz, DMSO-d$_6$) δ 10.07 (d, J=0.8 Hz, 1H), 9.55 (dd, J=2.2, 0.9 Hz, 1H), 9.03 (s, 1H), 8.73 (ddd, J=8.1, 2.2, 0.8 Hz, 1H), 8.39 (s, 1H), 8.08 (dd, J=8.1, 0.9 Hz, 1H), 4.53 (q, J=7.0 Hz, 2H), 1.42 (t, J=7.0 Hz, 3H).

5-(6-(Trifluoromethyl)pyrazin-2-yl)picolinic acid INTF51

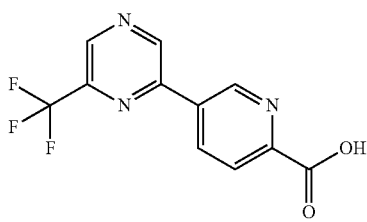 [SMILES: O=C(O)c1ccc(-c2cncc(C(F)(F)F)n2)cn1]

A solution of 5-(6-(trifluoromethyl)pyrazin-2-yl)picolinaldehyde INTF48 (200 mg, 0.79 mmol) in DMF (2 mL) was treated with oxone (650 mg, 1.06 mmol). The reaction mixture was stirred at RT for 4 days. The reaction mixture was diluted with water (10 mL) and filtered. The filtrate was then taken up in EtOAc (10 mL) and heated to 40° C. to afford a free flowing suspension. This was then treated dropwise with iso-hexanes (10 mL), cooled to RT and filtered to afford 5-(6-(trifluoromethyl)pyrazin-2-yl)picolinic acid (180 mg, 0.56 mmol, 68% yield) as a colourless solid. $^1$H NMR (500 MHz, DMSO-d$_6$) δ 9.78 (s, 1H), 9.48 (dd, J=2.4, 0.8 Hz, 1H), 9.28 (s, 1H), 8.72 (dd, J=8.2, 2.3 Hz, 1H), 8.24 (dd, J=8.2, 0.8 Hz, 1H), v. br OH observed, not reported.

5-(6-Chloropyrazin-2-yl)picolinic acid INTF52

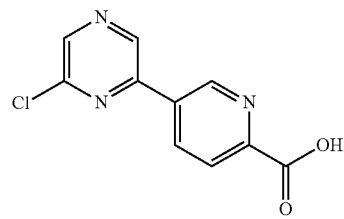 [SMILES: O=C(O)c1ccc(-c2cncc(Cl)n2)cn1]

Prepared as for INTF51 using 5-(6-chloropyrazin-2-yl)picolinaldehyde INTF49 to afford 5-(6-chloropyrazin-2-yl)picolinic acid (82% yield) as a colourless solid. Rt 1.32 min (HPLC, acidic); m/z 236 ($^{35}$Cl M+H)$^+$ (ES$^+$); $^1$H NMR (500 MHz, DMSO-d$_6$) δ 13.30 (s, 1H), 9.46 (s, 1H), 9.42 (d, J=2.1 Hz, 1H), 8.90 (s, 1H), 8.66 (dd, J=8.2, 2.1 Hz, 1H), 8.21 (d, J=8.2 Hz, 1H).

5-(6-Ethoxypyrazin-2-yl)picolinic acid INTF53

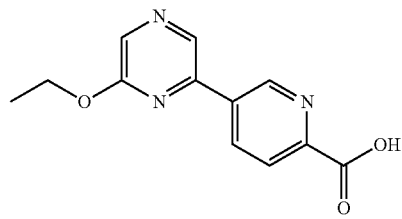 [SMILES: CCOc1cncc(-c2ccc(C(=O)O)nc2)n1]

Prepared as for INTF51 using 5-(6-ethoxypyrazin-2-yl)picolinaldehyde INTF50 to afford 5-(6-ethoxypyrazin-2-yl)picolinic acid (71% yield) as a colourless solid. Rt 1.45 min (HPLC, acidic); m/z 246 (M+H)$^+$ (ES$^+$); $^1$H NMR (500 MHz, DMSO-d$_6$) δ 13.31 (s, 1H), 9.46-9.38 (m, 1H), 8.98 (s, 1H), 8.64 (dd, J=8.1, 2.3 Hz, 1H), 8.36 (s, 1H), 8.17 (dd, J=8.1, 0.8 Hz, 1H), 4.51 (q, J=7.0 Hz, 2H), 1.42 (t, J=7.0 Hz, 3H).

Preparation of Examples

Method 1: Amide Coupling

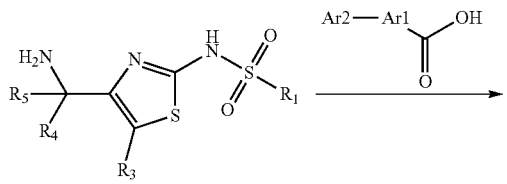

-continued

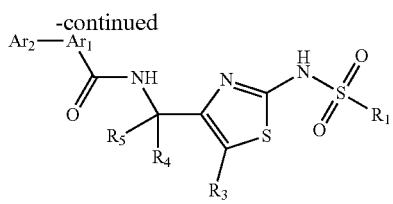

Method 1a: HATU (1.2 eq.) was added to a solution of appropriate acid (1 eq.), amine (1 eq.) and DIPEA (3 eq.) in DMF (10 volumes) at RT. The reaction was stirred at RT for 18 hrs. The solvent was removed and the crude product was purified by normal phase chromatography, reverse phase chromatography or trituration from an appropriate solvent.

Method 1b: 1-chloro-N,N,2-trimethylprop-1-en-1-amine (2 eq.) was added to a solution of appropriate acid (1 eq.) in DCM (20 volumes). The reaction mixture was stirred at RT for 2 hrs. The reaction mixture was concentrated in vacuo and the residue dissolved in DCM (20 volumes) before addition of DIPEA (3 eq.) and the appropriate amine (1 eq). The reaction mixture was stirred at RT for 2 hrs. An aqueous work up was performed and the crude product was purified by normal phase chromatography, reverse phase chromatography or trituration from an appropriate solvent.

Method 1c: T3P (50 wt % in EtOAc, 2.5 eq.) was added to a solution of appropriate acid (1 eq.), amine (1 eq.) and pyridine (3 eq.) in a mixture of EtOAc (20 volumes) and DMF (10 volumes). The reaction was stirred for 1 hr at RT. An aqueous work up was performed and the crude product was purified by normal phase chromatography, reverse phase chromatography or trituration from an appropriate solvent.

Method 2a: Suzuki [ArB(OR)$_2$ Core]

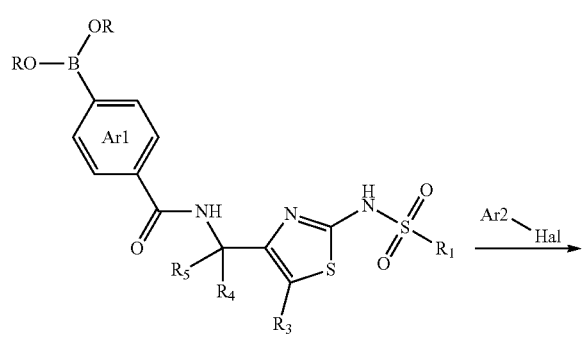

PdCl$_2$(dppf)-CH$_2$Cl$_2$ (10 mol %) or other appropriate catalyst was added to a degassed (N$_2$, 5 mins) solution of Ar1-B(OR)$_2$ (1 eq.), Ar2-halide (1 eq.) and K$_2$CO$_3$ (3 eq.) in dioxane (10 volumes) and water (1 volumes). The solution was then degassed further (N$_2$, 5 mins) and heated to 90° C. for 1-2 hrs. The reaction mixture was allowed to cool to RT. An aqueous workup was performed and the crude product was purified by normal phase chromatography, reverse phase chromatography or trituration from an appropriate solvent.

Method 2b: Telescoped Miyaura Borylation/Suzuki Protocol

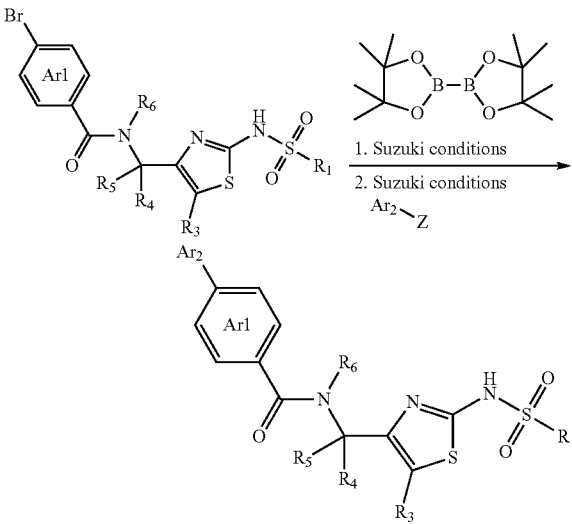

Z = Br, Cl

A suspension of Ar1-Br (1 eq.), Bispin (1.1 eq.) and KOAc (2 eq.) in dioxane (50 volumes) was degassed (N$_2$) then charged with PdCl$_2$(dppf)·CH$_2$Cl$_2$ (5 mol %) and again degassed (N$_2$). The reaction mixture was heated to 90° C. for 1-24 hrs, recharging the Pd-catalyst if required. On formation of the boronate ester the reaction was allowed to cool to RT. Ar2-Z (1 eq.) and 2 M K$_2$CO$_3$ (aq, 2 eq.) were added, degassed (N$_2$) and the reaction was then heated to 90° C. for 18 hrs. The reaction was allowed to cool to RT, an aqueous work up was performed and the crude compound was purified by normal phase chromatography.

Representative for Method 1a

N-((2-(cyclopropanesulfonamido)thiazol-4-yl)methyl)-4-(pyridin-3-yl)benzamide R1

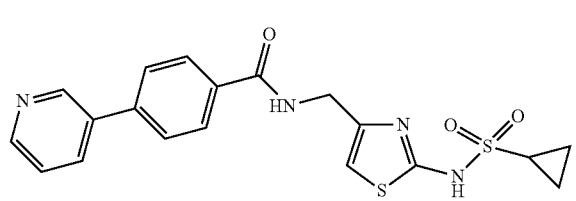 [SMILES: O=C(NCc1csc(NS(=O)(=O)C2CC2)n1)c1ccc(-c2cccnc2)cc1]

A solution of N-(4-(aminomethyl)thiazol-2-yl)cyclopropanesulfonamide INTE9 (64 mg, 0.274 mmol), 4-(pyridin-3-yl)benzoic acid (54.6 mg, 0.274 mmol) and DIPEA (0.14 mL, 0.82 mmol) in DMF (0.5 mL) was treated with HATU (110 mg, 0.288 mmol) and stirred at RT for 18 hrs. EtOAc (20 mL) was added and the organic phase was washed with water (10 mL) and brine (10 mL), dried ($Na_2SO_4$), filtered and concentrated onto silica (300 mg). The crude product was purified by chromatography on silica (12 g column, 0-7% (0.7 M ammonia/MeOH)/DCM). The crude product was further purified by reverse phase chromatography on C18 silica (12 g column, 10-40% MeCN/water 0.1% formic acid) to afford N-((2-(cyclopropanesulfonamido)thiazol-4-yl)methyl)-4-(pyridin-3-yl)benzamide (18 mg, 0.041 mmol, 15% yield) as a colourless solid. Rt 1.08 min (HPLC, HPLC Acidic); m/z 415 $(M+H)^+$ $(ES^+)$; $^1H$ NMR (400 MHz, DMSO-$d_6$) δ 12.57 (s, 1H), 9.04-8.94 (m, 2H), 8.62 (dd, J=4.8, 1.6 Hz, 1H), 8.17-8.14 (m, 1H), 8.06-7.98 (m, 2H), 7.92-7.84 (m, 2H), 7.50-7.48 (m, 1H), 6.53 (s, 1H), 4.35-4.33 (m, 2H), 2.64-2.52 (m, 1H), 0.09-0.87 (m, 4H).

Representative for Method 1b

N-(1-(2-(cyclopropanesulfonamido)thiazol-4-yl)propyl)-4-(5-(trifluoromethyl)pyridin-3-yl)benzamide R2

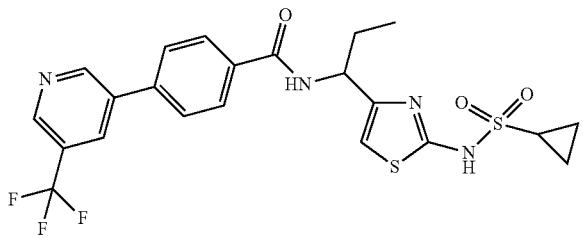 [SMILES: CCC(NC(=O)c1ccc(-c2cncc(C(F)(F)F)c2)cc1)c1csc(NS(=O)(=O)C2CC2)n1]

A suspension of 4-(5-(trifluoromethyl)pyridin-3-yl)benzoic acid INTF25 (46.2 mg, 0.173 mmol) in DCM (2 mL) was treated with 1-chloro-N,N,2-trimethylprop-1-en-1-amine (0.046 mL, 0.346 mmol) and stirred at RT for 1 hr before being concentrated. The residue was taken up in DCM (3 mL), treated with DIPEA (0.091 mL, 0.518 mmol) and stirred for 5 mins before N-(4-(1-aminopropyl)thiazol-2-yl)cyclopropanesulfonamide INTE10 (45 mg, 0.17 mmol) was added and the reaction mixture was stirred at RT for 16 hrs. The reaction mixture was treated with $NH_4Cl$ (sat. aq., 5 mL) and passed through a phase separator, further extracting with DCM (5 mL). The organic phase was concentrated onto silica (500 mg) and the crude product was purified by chromatography on silica [12 g column, 0-100% EtOAc (2% MeOH)/iso-hexanes] to afford N-(1-(2-(cyclopropanesulfonamido)thiazol-4-yl)propyl)-4-(5-(trifluoromethyl)pyridin-3-yl)benzamide (46 mg, 0.085 mmol, 49% yield) as a colourless solid. Rt 1.99 min (HPLC, acidic); m/z 511 $(M+H)^+$ $(ES^+)$; $^1H$ NMR (400 MHz, DMSO-d6) δ 12.60 (s, 1H), 9.30 (d, J=2.1 Hz, 1H), 9.03 (d, J=2.1 Hz, 1H), 8.74 (d, J=8.3 Hz, 1H), 8.56 (s, 1H), 8.09-7.97 (m, 4H), 6.56 (s, 1H), 4.90 (q, J=7.9 Hz, 1H), 2.64-2.51 (m, 1H), 1.98-1.74 (m, 2H), 0.98-0.81 (m, 7H).

The racemic mixture $R_2$ was separated by chiral preparative HPLC using chiral method A. A salt exchange (TFA to HCl) was undertaken by adding 1.25 M HCl (EtOH, 2 mL×5) and removing solvent to afford:

Peak 1: Stereochemistry of Product was not Defined R3

N-(1-(2-(cyclopropanesulfonamido)thiazol-4-yl)propyl)-4-(5-(trifluoromethyl)pyridin-3-yl)benzamide. HCl $R_3$ (13 mg, 0.023 mmol, 37% yield) was isolated as a colourless solid. Rt=1.30 min (UPLC, acidic); m/z 511 $(M+H)^+$ $(ES^+)$; $^1H$ NMR (500 MHz, DMSO-$d_6$) δ 12.61 (s, 1H), 9.30 (s, 1H), 9.03 (d, J=2.2 Hz, 1H), 8.75 (d, J=8.3 Hz, 1H), 8.56 (s, 1H), 8.09-8.04 (m, 2H), 8.03-7.98 (m, 2H), 6.57 (s, 1H), 4.94-4.87 (m, 1H), 2.64-2.51 (m, 1H), 1.97-1.74 (m, 2H), 0.96-0.85 (m, 7H). Signal for HCl not observed The product was analysed by Chiral HPLC, chiral IA method 1: [Daicel Chiralpak IA, 5 um, 4.6×250 mm, 45 min method, 1.0 mL/min, 5-95% (gradient over 45 min) EtOH (0.2% TFA) in iso-hexanes (0.2% TFA)]; Rt=14.8 min, >98% @ 254 nm.

Peak 2: Stereochemistry of Product was not Defined $R_4$

N-(1-(2-(cyclopropanesulfonamido)thiazol-4-yl)propyl)-4-(5-(trifluoromethyl)pyridin-3-yl)benzamide. HCl $R_4$ (12 mg, 0.021 mmol, 34% yield) was obtained as a colourless solid. Rt=1.30 min (UPLC, acidic); m/z 511 $(M+H)^+$ $(ES^+)$; $^1H$ NMR (500 MHz, DMSO-$d_6$) δ 12.61 (s, 1H), 9.30 (d, J=2.2 Hz, 1H), 9.03 (d, J=2.1 Hz, 1H), 8.75 (d, J=8.1 Hz, 1H), 8.56 (s, 1H), 8.08-8.04 (m, 2H), 8.03-7.99 (m, 2H), 6.57 (s, 1H), 4.95-4.85 (m, 1H), 2.64-2.51 (m, 1H), 1.97-1.73 (m, 2H), 0.97-0.82 (m, 7H). Signal for HCl not observed The product was analysed by Chiral HPLC, chiral IA method 1: [Daicel Chiralpak IA, 5 um, 4.6×250 mm, 45 min method, 1.0 mL/min, 5-95% (gradient over 45 min) EtOH (0.2% TFA) in iso-hexanes (0.2% TFA)]; Rt=16.8 min, >98% @ 254 nm.

Representative for Method 1c

N-(1-(2-(cyclopropanesulfonamido)thiazol-4-yl)propyl)-4-(6-(trifluoromethyl)pyrazin-2-yl)benzamide R5

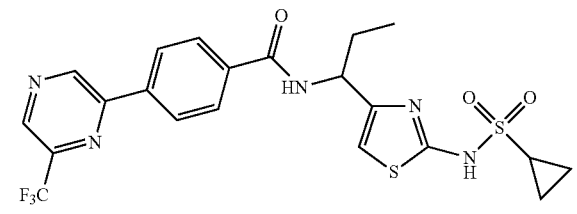 [SMILES: CCC(NC(=O)c1ccc(-c2cncc(C(F)(F)F)n2)cc1)c1csc(NS(=O)(=O)C2CC2)n1]

A solution of 4-(6-(trifluoromethyl)pyrazin-2-yl)benzoic acid INTF28 (15.4 mg, 0.057 mmol) and N-(4-(1-aminopropyl)thiazol-2-yl)cyclopropanesulfonamide INTE10 (15 mg, 0.057 mmol) in DMF (0.25 mL) was treated with pyridine (0.014 mL, 0.172 mmol) and T3P (50% wt. in DMF, 0.125 mL, 0.172 mmol). The reaction mixture was allowed to stir at RT over 16 hrs. The crude product was treated with water (0.05 mL) and purified by reverse phase chromatography on C18 silica (12 g column, 10-50% MeCN/10 mM ammonium bicarbonate) to afford N-(1-(2-(cyclopropanesulfonamido)thiazol-4-yl)propyl)-4-(6-(trifluoromethyl)pyrazin-2-yl)benzamide (2.5 mg, 0.004 mmol, 8% yield) as a colourless solid. Rt 1.34 min (UPLC, acidic); m/z 512 (M+H)⁺ (ES⁺). ¹H NMR (400 MHz, Chloroform-d) δ 9.30 (s, 1H), 8.95 (s, 1H), 8.18 (d, J=8.3 Hz, 2H), 8.12 (d, J=84 Hz, 2H), 8.04 (d, J=8.1 Hz, 1H), 6.51 (s, 1H), 5.09-4.95 (m, 1H), 2.56.2.53 (m, 1H), 2.17-1.89 (m, 2H), 1.32-1.09 (m, 2H), 1.09-0.71 (m, 5H), N—H not observed.

Representative for Method 2a

N-(2-(2-(cyclopropanesulfonamido)thiazol-4-yl)propan-2-yl)-4-(6-ethoxypyrazin-2-yl)-2-fluorobenzamide R6

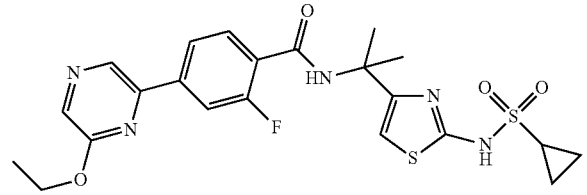 [SMILES: CCOc1cncc(-c2ccc(C(=O)NC(C)(C)c3csc(NS(=O)(=O)C4CC4)n3)c(F)c2)n1]

A solution of N-(2-(2-(cyclopropanesulfonamido)thiazol-4-yl)propan-2-yl)-2-fluoro-4-(4,4,5,5-tetramethyl-1,3,2-dioxaborolan-2-yl)benzamide INTE20 (80 mg, 0.157 mmol), 2 M potassium carbonate (aq, 0.16 mL, 0.314 mmol) and 2-chloro-6-ethoxypyrazine (25 mg, 0.157 mmol) in MeCN (15 mL) and water (2 mL) was degassed (N₂) at 40° C. whereupon PdCl₂(dppf)-CH₂Cl₂ (6.4 mg, 0.008 mmol) was added to form a suspension. The mixture was degassed (N₂) then heated to 90° C. for 3 hrs. The reaction was cooled to RT, concentrated directly onto silica (1 g) and was purified by chromatography on silica (12 g column, 0-100% EtOAc/iso-hexanes) to afford N-(2-(2-(cyclopropanesulfonamido)thiazol-4-yl)propan-2-yl)-4-(6-ethoxypyrazin-2-yl)-2-fluorobenzamide (13 mg, 0.025 mmol, 16% yield) as a colourless solid. Rt 1.34 min (UPLC, acidic); m/z 506 (M+H)⁺ (ES⁺). ¹H NMR (400 MHz, DMSO-d₆) δ 12.58 (s, 1H), 8.93 (s, 1H), 8.36 (s, 1H), 8.32 (s, 1H), 8.11-7.96 (m, 2H), 7.84 (t, J=7.7 Hz, 1H), 6.50 (d, J=8.5 Hz, 1H), 4.50 (q, J=7.0 Hz, 2H), 2.63-2.54 (m, 1H), 1.63 (s, 6H), 1.41 (t, J=7.0 Hz, 3H), 0.95-0.83 (m, 4H).

Representative for Method 2b

N-(2-(2-(cyclopropanesulfonamido)thiazol-4-yl)propan-2-yl)-4-(6-ethoxypyrazin-2-yl)-2-methoxybenzamide R7

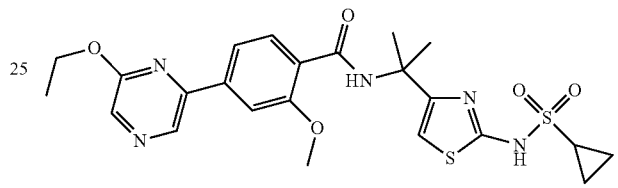

A suspension of 4-bromo-N-(2-(2-(cyclopropanesulfonamido)thiazol-4-yl)propan-2-yl)-2-methoxybenzamide INTE18 (100 mg, 0.211 mmol), Bispin (59 mg, 0.232 mmol) and KOAc (41 mg, 0.422 mmol) in dioxane (5 mL) was degassed (N₂) then charged with PdCl₂(dppf)-CH₂Cl₂ (8.6 mg, 0.011 mmol) and degassed (N₂). The reaction mixture was heated to 90° C. for 16 hrs. The reaction mixture was allowed to cool then filtered through celite. This was then recharged with KOAc (41 mg, 0.422 mmol), Bispin (59 mg, 0.232 mmol) and PdCl₂(dppf)-CH₂Cl₂ (8.6 mg, 0.011 mmol), degassed (N₂) then heated to 90° C. for 2 hrs. To the reaction mixture was added 2-chloro-6-ethoxypyrazine (33.4 mg, 0.211 mmol) and 2 M potassium carbonate (aq, 0.21 mL, 0.422 mmol) and heated to 90° C. for 16 hrs. The reaction mixture was allowed to cool to RT then diluted with EtOAc (10 mL) and water (10 mL), filtered over celite eluting with EtOAc (10 mL). The phases were then partitioned, washed with brine (10 mL), dried (Na₂SO₄), filtered and concentrated onto silica (500 mg). The crude product was purified by chromatography on silica (12 g cartridge, 0-100% EtOAc/iso-hexanes). The resulting product was re-purified by preparative HPLC (Varian, Basic (0.1% ammonium bicarbonate), 15-50% MeCN in water) to afford N-(2-(2-(cyclopropanesulfonamido)thiazol-4-yl)propan-2-yl)-4-(6-ethoxypyrazin-2-yl)-2-methoxybenzamide (20 mg, 0.037 mmol, 17% yield) as a colourless solid. Rt 2.17 min (HPLC acidic); m/z 518 (M+H)⁺ (ES⁺). ¹H NMR (500 MHz, DMSO-d₆) δ 12.56 (s, 1H), 8.94 (s, 1H), 8.39 (s, 1H), 8.30 (s, 1H), 7.91 (d, J=8.1 Hz, 1H), 7.86 (d, J=1.5 Hz, 1H), 7.82 (dd, J=8.1, 1.5 Hz, 1H), 6.49 (s, 1H), 4.50 (q, J=7.0 Hz, 2H), 4.07 (s, 3H), 2.59-2.52 (m, 1H), 1.65 (s, 6H), 1.41 (t, J=7.0 Hz, 3H), 0.95-0.76 (m, 4H).

TABLE 6

| | | Synthesis Method, [LCMS Method], | |
|---|---|---|---|
| R | Name/Structure (All examples containing chiral centres are racemic unless stated) | m/z (M + H)+, (RT/Min) | ¹H NMR Chemical Shift Data (DMSO-d6 unless stated) |
| R8 | N-((2-(cyclopropanesulfon-amido)thiazol-4-yl)methyl)-5-phenylpicolinamide | Method 1a, Using INTE9 and commercial acid, [UPLC Basic], 415 (1.23) | 12.55 (s, 1H), 9.26 (t, J = 6.2 Hz, 1H), 8.99 (dd, J = 2.3, 0.8 Hz, 1H), 8.31 (dd, J = 8.2, 2.3 Hz, 1H), 8.13 (dd, J = 8.2, 0.8 Hz, 1H), 7.87-7.77 (m, 2H), 7.61-7.53 (m, 2H), 7.52-7.43 (m, 1H), 6.50 (s, 1H), 4.38 (dd, J = 6.3, 1.2 Hz, 2H), 2.62-2.55 (m, 1H), 0.96-0.81 (m, 4H). |
| R9 | N-((2-(cyclopropanesulfon-amido)thiazol-4-yl)methyl)-[1,1'-biphenyl]-4-carboxamide | Method 1a, Using INTE9 and commercial acid [HPLC Basic], 414, (1.72) | 12.58 (s, 1H), 8.97 (t, J = 5.6 Hz, 1H), 8.05-7.95 (m, 2H), 7.84-7.70 (m, 4H), 7.55-7.46 (m, 2H), 7.45-7.36 (m, 1H), 6.53 (s, 1H), 4.34 (d, J = 5.4 Hz, 2H), 2.63-2.54 (m, 1H), 0.93-0.86 (m, 4H). |
| R10 | N-((2-(cyclopropanesulfon-amido)thiazol-4-yl)methyl)-2-fluoro-4-(6-(trifluoromethyl)-pyrazin-2-yl)benzamide | Method 1a, Using INTE9 and INTF34, [UPLC Acidic], 502, (1.24) | 12.60 (s, 1H), 9.73 (s, 1H), 9.24 (s, 1H), 9.04-8.78 (m, 1H), 8.23-8.08 (m, 2H), 7.98-7.81 (m, 1H), 6.54 (s, 1H), 4.35 (d, J = 5.6 Hz, 2H), 2.62-2.55 (m, 1H), 0.94-0.79 (m, 4H). |
| R11 | N-((2-(cyclopropanesulfon-amido)thiazol-4-yl)methyl)-4-(6-ethoxypyrazin-2-yl)-2-fluorobenzamide | Method 1a, Using INTE9 and INTF35, [UPLC Acidic], 478, (1.22) | 12.58 (s, 1H), 8.93 (s, 1H), 8.88-8.83 (m, 1H), 8.32 (s, 1H), 8.11-8.04 (m, 2H), 7.88-7.79 (m, 1H), 6.54 (s, 1H), 4.50 (q, J = 7.0 Hz, 2H), 4.34 (d, J = 5.6 Hz, 2H), 2.62-2.54 (m, 1H), 1.41 (t, J = 7.0 Hz, 3H), 0.93-0.81 (m, 4H). |
| R12 | N-((2-(cyclopropanesulfon-amido)thiazol-4-yl)methyl)-4-(6-(trifluoromethyl)pyrazin-2-yl)benzamide | Method 1a, Using INTE9 and INTF28, [UPLC Acidic], 484, (1.21) | 12.60 (s, 1H), 9.71 (s, 1H), 9.20 (s, 1H), 9.14-9.01 (m, 1H), 8.35-8.31 (m, 2H), 8.11-8.06 (m, 2H), 6.55 (s, 1H), 4.35 (d, J = 5.5 Hz, 2H), 2.61-2.55 (m, 1H), 0.94-0.77 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R13 | N-((2-(cyclopropanesulfon-amido)thiazol-4-yl)methyl)-4-(6-isopropoxypyrazin-2-yl)benzamide | Method 1a, Using INTE9 and INTF30, [UPLC Acidic], 474, (1.28) | 12.59 (s, 1H), 9.05-8.99 (m, 1H), 8.87 (s, 1H), 8.26-8.19 (m, 3H), 8.05-8.01 (m, 2H), 6.54 (s, 1H), 5.48-5.37 (m, 1H), 4.35 (d, J = 5.4 Hz, 2H), 2.61-2.55 (m, 1H), 1.39 (d, J = 6.1 Hz, 6H), 0.92-0.82 (m, 4H). |
| R14 | N-((2-(cyclopropanesulfon-amido)thiazol-4-yl)methyl)-4-(6-ethoxypyrazin-2-yl)benzamide | Method 1a, Using INTE9 and INTE37, [UPLC Acidic], 460, (1.18) | 12.60 (s, 1H), 9.03 (t, J = 5.6 Hz, 1H), 8.90 (s, 1H), 8.30 (s, 1H), 8.28-8.22 (m, 2H), 8.08-8.00 (m, 2H), 6.54 (s, 1H), 4.51 (q, J = 7.1 Hz, 2H), 4.35 (d, J = 5.4 Hz, 2H), 2.61-2.55 (m, 1H), 1.42 (t, J = 7.0 Hz, 3H), 0.95-0.84 (m, 4H). |
| R15 | N-(3-(2-(cyclopropanesulfon-amido)thiazol-4-yl)pentan-3-yl)-4-(5-(trifluoromethyl)pyridin-3-yl)benzamide | Method 1b, Using INTE17 and INTF25, [HPLC acidic], 539, (2.13) | 12.52 (s, 1H), 9.30 (d, J = 2.1 Hz, 1H), 9.02 (dd, J = 2.1, 0.9 Hz, 1H), 8.56 (s, 1H), 8.12-7.95 (m, 5H), 6.50 (s, 1H), 2.60-2.53 (m, 1H), 2.27-2.13 (m, 2H), 1.91-1.70 (m, 2H), 0.93-0.85 (m, 4H), 0.77-0.69 (m, 6H). |
| R16 | N-(3-(2-(cyclopropanesulfon-amido)thiazol-4-yl)pentan-3-yl)-4-(5-fluoropyridin-3-yl)benzamide | Method 1b, Using INTE17 and INTF26, [HPLC Acidic], 489, (1.9) | 12.50 (s, 1H), 8.89 (t, J = 1.8 Hz, 1H), 8.62 (d, J = 2.7 Hz, 1H), 8.17 (ddd, J = 10.3, 2.8, 1.9 Hz, 1H), 8.07-7.98 (m, 3H), 7.97-7.86 (m, 2H), 6.48 (s, 1H), 2.60-2.52 (m, 1H), 2.29-2.15 (m, 2H), 1.87-1.71 (m, 2H), 0.92-0.82 (m, 4H), 0.73 (t, J = 7.3 Hz, 6H). |
| R17 | N-(3-(2-(cyclopropanesulfon-amido)thiazol-4-yl)pentan-3-yl)-4-(5-methylpyridin-3-yl)benzamide | Method 1b, Using INTE17 and INTF24, [HPLC acidic], 485, (1.36) | 12.50 (s, 1H), 8.77 (d, J = 2.2 Hz, 1H), 8.46 (dd, J = 2.0, 0.8 Hz, 1H), 8.08-7.96 (m, 4H), 7.89-7.79 (m, 2H), 6.49 (s, 1H), 2.61-2.55 (m, 1H), 2.40 (s, 3H), 2.29-2.12 (m, 2H), 1.88-1.75 (m, 2H), 0.94-0.83 (m, 4H), 0.73 (t, J = 7.2 Hz, 6H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
| --- | --- | --- | --- |
| R18 | N-(3-(2-(cyclopropanesulfon-amido)thiazol-4-yl)pentan-3-yl)-4-(pyridin-3-yl)benzamide | Method 1b, Using INTE17 and commercial acid, [HPLC Acidic], 471, (1.36) | 12.50 (s, 1H), 8.98 (dd, J = 2.4, 0.9 Hz, 1H), 8.62 (dd, J = 4.8, 1.6 Hz, 1H), 8.20-8.12 (m, 1H), 8.07-7.97 (m, 3H), 7.91-7.82 (m, 2H), 7.53 (ddd, J = 8.1, 4.8, 0.9 Hz, 1H), 6.49 (s, 1H), 2.61-2.54 (m, 1H), 2.28-2.12 (m, 2H), 1.89-1.73 (m, 2H), 0.94-0.82 (m, 4H), 0.74 (t, J = 7.3 Hz, 6H). |
| R19 | N-(3-(2-(cyclopropanesulfon-amido)thiazol-4-yl)pentan-3-yl)-4-(6-(trifluoromethyl)pyrazin-2-yl)benzamide | Method 1b, Using INTE17 and INTF28, [UPLC acidic], 540, (1.44) | 12.53 (s, 1H), 9.72 (s, 1H), 9.21 (s, 1H), 8.35-8.28 (m, 2H), 8.17-8.04 (m, 3H), 6.51 (s, 1H), 2.59-2.53 (m, 1H), 2.28-2.14 (m, 2H), 1.87-1.74 (m, 2H), 0.92-0.84 (m, 4H), 0.74 (t, J = 7.4 Hz, 6H). |
| | 4-(6-chloropyrazin-2-yl)-N-(3-(2-(cyclopropanesulfonamido)thiazol-4-yl)pentan-3-yl)benzamide | Method 1b, Using INTE17 and INTF27, [HPLC acidic], 506 ³⁵Cl isotope, (2.06) | 12.52 (s, 1H), 9.38 (s, 1H), 8.81 (s, 1H), 8.29-8.21 (m, 2H), 8.15-8.02 (m, 3H), 6.49 (s, 1H), 2.60-2.50 (m, 1H), 2.28-2.12 (m, 2H), 1.90-1.72 (m, 2H), 0.92-0.82 (m, 4H), 0.78-0.61 (m, 6H). |
| R21 | N-(3-(2-(cyclopropanesulfon-amido)thiazol-4-yl)pentan-3-yl)-4-(6-methylpyrazin-2-yl)benzamide | Method 1b, Using INTE17 and INTF29, [HPLC Acidic], 486, (1.89) | 12.52 (s, 1H), 9.15 (s, 1H), 8.57 (s, 1H), 8.28-8.20 (m, 2H), 8.08-8.01 (m, 3H), 6.50 (s, 1H), 2.60 (s, 3H), 2.60-2.54 (m, 1H), 2.26-2.16 (m, 2H), 1.86-1.76 (m, 2H), 0.92-0.84 (m, 4H), 0.74 (t, J = 7.4 Hz, 6H). |
| R22 | N-(3-(2-(cyclopropanesulfon-amido)thiazol-4-yl)pentan-3-yl)-4-(pyrazin-2-yl)benzamide | Method 1b, Using INTE17 and commercial acid, [HPLC Acidic], 472, (1.77) | 12.51 (s, 1H), 9.35 (d, J = 1.5 Hz, 1H), 8.77 (dd, J = 2.5, 1.5 Hz, 1H), 8.67 (d, J = 2.5 Hz, 1H), 8.28-8.22 (m, 2H), 8.08-8.00 (m, 3H), 6.49 (s, 1H), 2.59-2.51 (m, 1H), 2.26-2.14 (m, 2H), 1.86-1.72 (m, 2H), 0.92-0.84 (m, 4H), 0.73 (t, J = 7.3 Hz, 6H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | 1H NMR Chemical Shift Data (DMSO-d6 unless stated) |
|---|---|---|---|
| R23 | N-(2-(2-(cyclopropanesulfon-amido)thiazol-4-yl)propan-2-yl)-5-(6-ethoxypyrazin-2-yl)-3-fluoropicolinamide | Method 1a, Using INTE14 and INTF44 [HPLC Acidic], 507, (1.99) | 12.60 (s, 1H), 9.24 (d, J = 1.4 Hz, 1H), 9.02 (s, 1H), 8.59-8.46 (m, 2H), 8.39 (s, 1H), 6.54 (s, 1H), 4.52 (q, J = 7.0 Hz, 2H), 2.63-2.53 (m, 1H), 1.67 (s, 6H), 1.41 (t, J = 7.0 Hz, 3H), 0.93-0.85 (m, 4H). |
| R24 | N-(2-(2-(cyclopropanesulfon-amido)thiazol-4-yl)propan-2-yl)-5-(6-(trifluoromethyl)pyrazin-2-yl)picolinamide | Method 1a, Using INTE14 and INTF51 [HPLC Acidic], 513, (2.06) | 12.64 (s, 1H), 9.80 (s, 1H), 9.47 (d, J = 2.1 Hz, 1H), 9.29 (s, 1H), 8.76 (dd, J = 8.2, 2.2 Hz, 1H), 8.51 (s, 1H), 8.21 (d, J = 8.2 Hz, 1H), 6.58 (s, 1H), 2.60-2.53 (m, 1H), 1.71 (s, 6H), 0.94-0.79 (m, 4H). |
| R25 | 5-(6-chloropyrazin-2-yl)-N-(2-(2-(cyclopropanesulfonamido)thiazol-4-yl)propan-2-yl)picolinamide | Method 1a, Using INTE14 and INTF52, [HPLC Acidic], 479 35Cl isotope, (1.92) | 12.62 (s, 1H), 9.46 (s, 1H), 9.39 (d, J = 2.2 Hz, 1H), 8.89 (s, 1H), 8.69 (dd, J = 8.2, 2.2 Hz, 1H), 8.51 (s, 1H), 8.17 (d, J = 8.1 Hz, 1H), 6.55 (s, 1H), 2.60-2.53 (m, 1H), 1.70 (s, 6H), 0.91-0.81 (m, 4H). |
| R26 | N-(2-(2-(cyclopropanesulfon-amido)thiazol-4-yl)propan-2-yl)-5-(6-ethoxypyrazin-2-yl)picolinamide | Method 1a, Using INTE14 and INTF53 [HPLC Acidic], 489, (2.04) | 12.62 (s, 1H), 9.41 (d, J = 2.2 Hz, 1H), 8.99 (s, 1H), 8.69 (dd, J = 8.2, 2.2 Hz, 1H), 8.47 (s, 1H), 8.37 (s, 1H), 8.13 (d, J = 8.1 Hz, 1H), 6.56 (s, 1H), 4.51 (q, J = 7.0 Hz, 2H), 2.59-2.53 (m, 1H), 1.70 (s, 6H), 1.41 (t, J = 7.0 Hz, 3H), 0.95-0.83 (m, 4H). |
| R27 | N-(2-(2-(cyclopropanesulfon-amido)thiazol-4-yl)propan-2-yl)-[2,2'-bipyridine]-5-carboxamide | Method 1a, Using INTE14 and commercial acid [HPLC Acidic], 444, (1.39) | 12.59 (s, 1H), 9.13 (d, J = 2.2 Hz, 1H), 8.81-8.74 (m, 1H), 8.59 (s, 1H), 8.51-8.45 (m, 2H), 8.45 (s, 1H), 8.09-7.92 (m, 1H), 7.52 (ddd, J = 7.5, 4.7, 1.2 Hz, 1H), 6.52 (s, 1H), 2.62-2.54 (m, 1H), 1.65 (s, 6H), 0.96-0.84 (m, 4H). |

TABLE 6-continued

*The following final compounds were made according to general methods*

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R28 | 4-(5-chloropyridin-3-yl)-N-(2-(2-(cyclopropanesulfon-amido)thiazol-4-yl)propan-2-yl)benzamide | Method 1a, Using INTE14 and INTF31, [UPLC Acidic], 477 $^{35}$Cl isotope, (1.2) | 12.57 (s, 1H), 8.98-8.93 (m, 1H), 8.72-8.65 (m, 1H), 8.40-8.32 (m, 2H), 8.04-7.97 (m, 2H), 7.97-7.89 (m, 2H), 6.46 (s, 1H), 2.63-2.53 (m, 1H), 1.64 (s, 6H), 0.94-0.82 (m, 4H). |
| R29 | N-(2-(2-(cyclopropanesulfon-amido)thiazol-4-yl)propan-2-yl)-2-fluoro-4-(5-(trifluoromethyl)pyridin-3-yl)benzamide | Method 2a, Using INTE20 and commercial coupling partner, [UPLC Acidic], 529, (1.32) | 12.59 (s, 1H), 9.31 (d, J = 2.2 Hz, 1H), 9.04-9.01 (m, 1H), 8.60 (s, 1H), 8.39 (s, 1H), 7.92 (d, J = 11.9 Hz, 1H), 7.89-7.82 (m, 2H), 6.49 (s, 1H), 2.62-2.54 (m, 1H), 1.63 (s, 6H), 0.94-0.84 (m, 4H). |
| R30 | 4-(5-chloropyridin-3-yl)-N-(2-(2-(cyclopropanesulfon-amido)thiazol-4-yl)propan-2-yl)-2-fluorobenzamide | Method 1a, Using INTE14 and INTF33, [UPLC Acidic], 495 $^{35}$Cl isotope, (1.24) | 12.59 (s, 1H), 8.98 (d, J = 2.1 Hz, 1H), 8.69 (d, J = 2.2 Hz, 1H), 8.40 (t, J = 2.2 Hz, 1H), 8.37 (s, 1H), 7.87-7.81 (m, 2H), 7.78 (dd, J = 8.1, 1.7 Hz, 1H), 6.48 (s, 1H), 2.62-2.54 (m, 1H), 1.63 (s, 6H), 0.96-0.81 (m, 4H). |
| R31 | N-(2-(2-(cyclopropanesulfon-amido)thiazol-4-yl)propan-2-yl)-2-fluoro-4-(5-fluoropyridin-3-yl)benzamide | Method 2a, Using INTE20 and commercial coupling partner, [UPLC Acidic], 479, (1.15) | 12.58 (s, 1H), 8.91 (d, J = 1.9 Hz, 1H), 8.64 (d, J = 2.6 Hz, 1H), 8.37 (s, 1H), 8.27-8.15 (m, 1H), 7.88-7.74 (m, 3H), 6.49 (s, 1H), 2.65-2.51 (m, 1H), 1.62 (s, 6H), 0.94-0.81 (m, 4H). |
| R32 | N-(2-(2-(cyclopropanesulfon-amido)thiazol-4-yl)propan-2-yl)-2-methoxy-4-(5-(trifluoromethyl)pyridin-3-yl)benzamide | Method 2b, Using INTE18 and commercial coupling partner, [HPLC Acidic], 541, (2.16) | 12.56 (s, 1H), 9.31 (d, J = 2.2 Hz, 1H), 9.02 (dd, J = 2.1, 0.9 Hz, 1H), 8.59 (t, J = 2.3 Hz, 1H), 8.51-8.26 (m, 1H), 7.91 (d, J = 7.9 Hz, 1H), 7.61 (d, J = 1.7 Hz, 1H), 7.54 (dd, J = 8.1, 1.7 Hz, 1H), 6.48 (s, 1H), 4.08 (s, 3H), 2.59-2.53 (m, 1H), 1.65 (s, 6H), 0.94-0.78 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R33 | N-(2-(2-(cyclopropanesulfonamido)thiazol-4-yl)propan-2-yl)-4-(2-methylpyridin-3-yl)benzamide | Method 2a, Using INTE19 and commercial coupling partner, [HPLC acidic], 457, (1.04) | 12.55 (s, 1H), 8.49 (dd, J = 4.8, 1.8 Hz, 1H), 8.30 (s, 1H), 8.00-7.91 (m, 2H), 7.62 (dd, J = 7.7, 1.8 Hz, 1H), 7.53-7.47 (m, 2H), 7.33 (dd, J = 7.7, 4.8 Hz, 1H), 6.46 (s, 1H), 2.60-2.52 (m, 1H), 2.44 (s, 3H), 1.63 (s, 6H), 0.94-0.77 (m, 4H). |
| R34 | 4-(5-acetylpyridin-3-yl)-N-(2-(2-(cyclopropanesulfon-amido)thiazol-4-yl)propan-2-yl)benzamide | Method 2a, Using INTE19 and commercial coupling partner, [HPLC acidic], 485, (1.59) | 12.57 (s, 1H), 9.19 (d, J = 2.3 Hz, 1H), 9.14 (d, J = 2.0 Hz, 1H), 8.55 (t, J = 2.2 Hz, 1H), 8.34 (s, 1H), 8.08-8.00 (m, 2H), 7.98-7.91 (m, 2H), 6.47 (s, 1H), 2.72 (s, 3H), 2.61-2.51 (m, 1H), 1.64 (s, 6H), 0.93-0.82 (m, 4H). |
| R35 | N-(2-(2-(cyclopropanesulfon-amido)thiazol-4-yl)propan-2-yl)-4-(5-(trifluoromethyl)pyridin-3-yl)benzamide | Method 2a, Using INTE19 and commercial coupling partner, [HPLC Basic], 511, (1.79) | 12.57 (s, 1H), 9.29 (d, J = 2.1 Hz, 1H), 9.03-8.97 (m, 1H), 8.58-8.50 (m, 1H), 8.36 (s, 1H), 8.06-7.96 (m, 4H), 6.47 (s, 1H), 2.59-2.51 (m, 1H), 1.63 (s, 6H), 0.92-0.80 (m, 4H). |
| R36 | N-(2-(2-(cyclopropanesulfon-amido)thiazol-4-yl)propan-2-yl)-4-(5-fluoropyridin-3-yl)benzamide | Method 2a, Using INTE19 and commercial coupling partner, [HPLC Basic], 461, (1.54) | 12.56 (s, 1H), 8.91-8.84 (m, 1H), 8.62 (d, J = 2.7 Hz, 1H), 8.34 (s, 1H), 8.20-8.13 (m, 1H), 8.04-7.97 (m, 2H), 7.96-7.89 (m, 2H), 6.47 (s, 1H), 2.58-2.52 (m, 1H), 1.63 (s, 6H), 0.91-0.83 (m, 4H). |
| R37 | N-(2-(2-(cyclopropanesulfon-amido)thiazol-4-yl)propan-2-yl)-4-(5-methylpyridin-3-yl)benzamide | Method 1b, Using INTE14 and INTF24, [UPLC Acidic], 457, (0.74) | 12.55 (s, 1H), 8.77 (d, J = 2.2 Hz, 1H), 8.46 (dd, J = 2.1, 0.8 Hz, 1H), 8.31 (s, 1H), 8.02-7.93 (m, 3H), 7.89-7.81 (m, 2H), 6.48 (s, 1H), 2.61-2.53 (m, 1H), 2.40 (s, 3H), 1.64 (s, 6H), 0.97-0.71 (m, 4H). |

TABLE 6-continued

*The following final compounds were made according to general methods*

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R38 | N-(2-(2-(cyclopropanesulfon-amido)thiazol-4-yl)propan-2-yl)-4-(5-methoxypyridin-3-yl)benzamide | Method 1b, Using INTE14 and commercial acid, [UPLC Acidic], 473, (0.9) | 12.56 (s, 1H), 8.57 (d, J = 1.9 Hz, 1H), 8.34 (d, J = 2.8 Hz, 1H), 8.31 (s, 1H), 8.05-7.96 (m, 2H), 7.92-7.83 (m, 2H), 7.70 (dd, J = 2.8, 1.9 Hz, 1H), 6.48 (s, 1H), 3.94 (s, 3H), 2.63-2.50 (m, 1H), 1.64 (s, 6H), 0.96-0.82 (m, 4H). |
| R39 | N-(2-(2-(cyclopropanesulfon-amido)thiazol-4-yl)propan-2-yl)-4-(pyridin-3-yl)benzamide | Method 1b, Using INTE14 and commercial acid, [HPLC Acidic], 443, (1.18) | 12.56 (s, 1H), 8.98 (dd, J = 2.5, 0.9 Hz, 1H), 8.62 (dd, J = 4.7, 1.6 Hz, 1H), 8.31 (s, 1H), 8.17 (ddd, J = 8.0, 2.5, 1.6 Hz, 1H), 8.04-7.96 (m, 2H), 7.90-7.82 (m, 2H), 7.53 (ddd, J = 8.0, 4.8, 0.9 Hz, 1H), 6.48 (s, 1H), 1.64 (s, 6H), 1.00-0.78 (m, 4H), 1 × CH obscured |
| R40 | N-(2-(2-(cyclopropanesulfon-amido)thiazol-4-yl)propan-2-yl)-3'-(trifluoromethyl)-[1,1'-biphenyl]-4-carboxamide | Method 1a, Using INTE14 and commercial acid, [HPLC Acidic], 510, (2.35) | 12.57 (s, 1H), 8.33 (s, 1H), 8.11-8.04 (m, 2H), 8.04-7.99 (m, 2H), 7.91-7.85 (m, 2H), 7.80-7.69 (m, 2H), 6.48 (s, 1H), 2.60-2.54 (m, 1H), 1.64 (s, 6H), 0.93-0.84 (m, 4H). |
| R41 | N-(2-(2-(cyclopropanesulfon-amido)thiazol-4-yl)propan-2-yl)-4-(6-ethylpyrazin-2-yl)-2-fluorobenzamide | Method 1a, Using INTE14 and INTF39, [HPLC Acidic], 490, (1.97) | 12.59 (s, 1H), 9.19 (s, 1H), 8.62 (s, 1H), 8.38 (d, J = 2.5 Hz, 1H), 8.13-8.03 (m, 2H), 7.89-7.82 (m, 1H), 6.50 (s, 1H), 2.96-2.84 (m, 2H), 2.64-2.55 (m, 1H), 1.64 (s, 6H), 1.33 (t, J = 7.6 Hz, 3H), 0.97-0.82 (m, 4H). |
| R42 | N-(2-(2-(cyclopropanesulfonamido)thiazol-4-yl)propan-2-yl)-2-fluoro-4-(6-(trifluoromethyl)pyrazin-2-yl)benzamide | Method 2a, Using INTE20 and commercial coupling partner, [UPLC Acidic], 530, (1.36) | 12.60 (s, 1H), 9.73 (s, 1H), 9.23 (s, 1H), 8.47 (s, 1H), 8.17-8.08 (m, 2H), 7.95-7.86 (m, 1H), 6.50 (s, 1H), 2.63-2.53 (m, 1H), 1.63 (s, 6H), 0.97-0.73 (m, 4H). |
| R43 | N-(2-(2-(cyclopropanesulfonamido)thiazol-4-yl)propan-2-yl)-2-fluoro-4-(6-isopropoxypyrazin-2-yl)benzamide | Method 1a, Using INTE14 and INTF36, [UPLC Acidic], 520, (1.42) | 12.59 (s, 1H), 8.96-8.79 (m, 1H), 8.42-8.32 (m, 1H), 8.31-8.20 (m, 1H), 8.12-7.95 (m, 2H), 7.89-7.76 (m, 1H), 6.50 (s, 1H), 5.46-5.34 (m, 1H), 2.64-2.55 (m, 1H), 1.71-1.53 (m, 6H), 1.50-1.25 (m, 6H), 0.96-0.85 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R44 | N-(2-(2-(cyclopropanesulfon-amido)thiazol-4-yl)propan-2-yl)-2-fluoro-4-(6-(2,2,2-trifluoroethoxy)pyrazin-2-yl)benzamide | Method 1a, Using INTE14 and INTF40, [UPLC Acidic], 560, (1.4) | 12.59 (s, 1H), 9.09 (s, 1H), 8.52 (s, 1H), 8.40 (s, 1H), 8.18-8.09 (m, 2H), 7.92-7.82 (m, 1H), 6.50 (s, 1H), 5.24 (q, J = 9.0 Hz, 2H), 2.62-2.55 (m, 1H), 1.63 (s, 6H), 0.98-0.81 (m, 4H). |
| R45 | N-(2-(2-(cyclopropanesulfonamido)thiazol-4-yl)propan-2-yl)-2-methyl-4-(6-(trifluoromethyl)pyrazin-2-yl)benzamide | Method 1a, Using INTE14 and INTF43 [HPLC Acidic], 526, (2.09) | 12.61 (s, 1H), 9.66 (s, 1H), 9.17 (s, 1H), 8.46 (s, 1H), 8.14-8.02 (m, 2H), 7.71 (d, J = 7.9 Hz, 1H), 6.50 (s, 1H), 2.61-2.55 (m, 1H), 2.42 (s, 3H), 1.62 (s, 6H), 0.94-0.85 (m, 4H). |
| R46 | N-(2-(2-(cyclopropanesulfonamido)thiazol-4-yl)propan-2-yl)-4-(6-ethoxypyrazin-2-yl)-2-methylbenzamide | Method 1a, Using INTE14 and INTF38, [HPLC Acidic], 502, (2.04) | 12.58 (s, 1H), 8.84 (s, 1H), 8.38 (s, 1H), 8.26 (s, 1H), 8.01-7.93 (m, 2H), 7.64 (d, J = 8.0 Hz, 1H), 6.49 (s, 1H), 4.49 (q, J = 7.0 Hz, 2H), 2.56-2.51 (m, 1H), 2.40 (s, 3H), 1.61 (s, 6H), 1.41 (t, J = 7.0 Hz, 3H), 0.95-0.81 (m, 4H). |
| R47 | N-(2-(2-(cyclopropanesulfonamido)thiazol-4-yl)propan-2-yl)-4-(6-ethoxypyrazin-2-yl)-2-(trifluoromethyl)benzamide | Method 1a, Using INTE14 and INTF42, [HPLC Acidic], 556, (2.17) | 12.63 (s, 1H), 8.99 (s, 1H), 8.73 (s, 1H), 8.50 (dd, J = 8.1, 1.7 Hz, 1H), 8.43 (d, J = 1.6 Hz, 1H), 8.34 (s, 1H), 7.98 (d, J = 8.1 Hz, 1H), 6.53 (s, 1H), 4.50 (q, J = 7.0 Hz, 2H), 2.62-2.56 (m, 1H), 1.59 (s, 6H), 1.41 (t, J = 7.0 Hz, 3H), 0.95-0.85 (m, 4H). |
| R48 | N-(2-(2-(cyclopropanesulfonamido)thiazol-4-yl)propan-2-yl)-2-methoxy-4-(6-(trifluoromethyl)pyrazin-2-yl)benzamide | Method 2b, Using INTE18 and commercial coupling partner, [HPLC Acidic], 542, (2.2) | 12.55 (s, 1H), 9.75 (s, 1H), 9.21 (s, 1H), 8.38 (s, 1H), 7.95-7.70 (m, 3H), 6.51 (s, 1H), 4.07 (s, 3H), 2.59-2.54 (m, 1H), 1.65 (s, 6H), 0.96-0.80 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | 1H NMR Chemical Shift Data (DMSO-d6 unless stated) |
|---|---|---|---|
| R49 | 4-(6-chloropyrazin-2-yl)-N-(2-(2-(cyclopropanesulfonamido)thiazol-4-yl)propan-2-yl)-2-methoxybenzamide | Method 2b, Using INTE18 and commercial coupling partner, [HPLC Acidic], 508 35Cl isotope, (2.07) | 12.55 (s, 1H), 9.42 (s, 1H), 8.82 (s, 1H), 8.37 (s, 1H), 7.91 (d, J = 8.0 Hz, 1H), 7.86-7.81 (m, 2H), 6.51 (s, 1H), 4.06 (s, 3H), 2.60-2.51 (m, 1H), 1.64 (s, 6H), 1.02-0.74 (m, 4H). |
| R50 | 4-(6-cyanopyrazin-2-yl)-N-(2-(2-(cyclopropanesulfonamido)thiazol-4-yl)propan-2-yl)-2-methoxybenzamide | Method 2b, Using INTE18 and commercial coupling partner, [HPLC Acidic], 499, (1.94) | 12.55 (s, 1H), 9.70 (s, 1H), 9.23 (s, 1H), 8.39 (s, 1H), 7.96-7.82 (m, 3H), 6.51 (s, 1H), 4.07 (s, 3H), 2.62-2.53 (m, 1H), 1.64 (s, 6H), 0.96-0.74 (m, 4H). |
| R51 | N-(2-(2-(cyclopropanesulfon-amido)thiazol-4-yl)propan-2-yl)-4-(6-(trifluoromethyl)pyrazin-2-yl)benzamide | Method 1b, Using INTE14 and INF28, [UPLC Acidic], 512, (1.31) | 12.59 (s, 1H), 9.72 (s, 1H), 9.21 (s, 1H), 8.42 (s, 1H), 8.34-8.27 (m, 2H), 8.13-8.04 (m, 2H), 6.50 (s, 1H), 2.62-2.54 (m, 1H), 1.65 (s, 6H), 0.93-0.86 (m, 4H). |
| R52 | 4-(6-chloropyrazin-2-yl)-N-(2-(2-(cyclopropanesulfon-amido)thiazol-4-yl)propan-2-yl)benzamide | Method 1b, Using INTE14 and INTF27, [HPLC acidic], 478 35Cl isotope, (1.87) | 12.58 (s, 1H), 9.39 (s, 1H), 8.82 (s, 1H), 8.40 (s, 1H), 8.29-8.21 (m, 2H), 8.09-8.03 (m, 2H), 6.48 (s, 1H), 2.54-2.50 (m, 1H), 1.64 (s, 6H), 0.94-0.76 (m, 4H). |
| R53 | N-(2-(2-(cyclopropanesulfon-amido)thiazol-4-yl)propan-2-yl)-4-(6-methylpyrazin-2-yl)benzamide | Method 1b, Using INTE14 and INF29, [HPLC Acidic], 458, (1.68) | 12.58 (s, 1H), 9.15 (s, 1H), 8.56 (s, 1H), 8.35 (s, 1H), 8.28-8.20 (m, 2H), 8.06-7.98 (m, 2H), 6.49 (s, 1H), 2.63-2.55 (m, 4H), 1.64 (s, 6H), 0.96-0.79 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | 1H NMR Chemical Shift Data (DMSO-d6 unless stated) |
|---|---|---|---|
| R54 | N-(2-(2-(cyclopropanesulfon-amido)thiazol-4-yl)propan-2-yl)-4-(6-methoxypyrazin-2-yl)benzamide | Method 2a, Using INTE19 and commercial coupling partner, [HPLC Basic], 474, (1.63) | 12.57 (s, 1H), 8.93 (s, 1H), 8.34 (s, 1H), 8.32 (s, 1H), 8.27-8.23 (m, 2H), 8.06-7.94 (m, 2H), 6.48 (s, 1H), 4.04 (s, 3H), 2.54-2.51 (m, 1H), 1.63 (s, 6H), 0.93-0.82 (m, 4H). |
| R55 | N-(2-(2-(cyclopropanesulfon-amido)thiazol-4-yl)propan-2-yl)-4-(6-ethoxypyrazin-2-yl)benzamide | Method 2a, Using INTE19 and commercial coupling partner, [HPLC Basic], 488, (1.79) | 12.56 (s, 1H), 8.91 (s, 1H), 8.33 (s, 1H), 8.29 (s, 1H), 8.25-8.20 (m, 2H), 8.04-7.98 (m, 2H), 6.47 (s, 1H), 4.50 (q, J = 7.0 Hz, 2H), 2.59-2.53 (m, 1H), 1.63 (s, 6H), 1.41 (t, J = 7.0 Hz, 3H), 0.92-0.81 (m, 4H). |
| R56 | N-(2-(2-(cyclopropanesulfon-amido)thiazol-4-yl)propan-2-yl)-4-(6-isopropoxypyrazin-2-yl)benzamide | Method 1a, Using INTE14 and INTF30, [UPLC Basic], 502, (1.2) | 12.57 (s, 1H), 8.89 (s, 1H), 8.34 (s, 1H), 8.27-8.17 (m, 3H), 8.04-7.98 (m, 2H), 6.48 (s, 1H), 5.49-5.24 (m, 1H), 2.60-2.53 (m, 1H), 1.64 (s, 6H), 1.40 (d, J = 6.2 Hz, 6H), 0.92-0.78 (m, 4H). |
| R57 | N-(2-(2-(cyclopropanesulfon-amido)thiazol-4-yl)propan-2-yl)-4-(6-(2,2,2-trifluoroethoxy)pyrazin-2-yl)benzamide | Method 1a, Using INTE14 and INTF41, [UPLC Acidic], 542, (1.38) | 12.58 (s, 1H), 9.08 (s, 1H), 8.50 (s, 1H), 8.37 (s, 1H), 8.34-8.25 (m, 2H), 8.08-7.99 (m, 2H), 6.49 (s, 1H), 5.23 (q, J = 9.0 Hz, 2H), 2.60-2.54 (m, 1H), 1.64 (s, 6H), 0.96-0.83 (m, 4H). |
| R58 | N-(2-(2-(cyclopropanesulfon-amido)thiazol-4-yl)propan-2-yl)-4-(pyrazin-2-yl)benzamide | Method 1b, Using INTE14 and commercial acid, [HPLC Acidic], 444, (1.59) | 12.57 (s, 1H), 9.35 (d, J = 1.6 Hz, 1H), 8.76 (dd, J = 2.5, 1.5 Hz, 1H), 8.67 (d, J = 2.5 Hz, 1H), 8.36 (s, 1H), 8.29-8.22 (m, 2H), 8.09-7.95 (m, 2H), 6.48 (s, 1H), 2.60-2.52 (m, 1H), 1.63 (s, 6H), 0.91-0.83 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
| --- | --- | --- | --- |
| R59 | RACEMIC, N-(1-(2-(cyclopropanesulfonamido)thiazol-4-yl)propyl)-4-(5-fluoropyridin-3-yl)benzamide | Method 1b, Using INTE10 and INTF26, [HPLC acidic], 461, (1.74) | 12.60 (s, 1H), 8.91-88 (m, 1H), 8.72 (d, J = 8.3 Hz, 1H), 8.64 (d, J = 2.7 Hz, 1H), 8.21-8.16 (m, 1H), 8.08-8.02 (m, 2H), 7.99-7.92 (m, 2H), 6.56 (s, 1H), 4.94-4.85 (m, 1H), 2.64-2.55 (m, 1H), 1.97-1.72 (m 2H), 0.97-0.76 (m, 7H). |
| R60 | RACEMIC, N-(1-(2-(cyclopropanesulfonamido)thiazol-4-yl)propyl)-4-(5-methylpyridin-3-yl)benzamide | Method 1b, Using INTE10 and INTF24, [HPLC acidic], 457, (1.22) | 12.57 (s, 1H), 8.76 (d, J = 2.3 Hz, 1H), 8.68 (d, J = 8.2 Hz, 1H), 8.46 (dd, J = 2.0, 0.8 Hz, 1H), 8.06-7.95 (m, 3H), 7.90-7.82 (m, 2H), 6.54 (s, 1H), 4.94-4.83 (m, 1H), 2.62-2.55 (m, 1H), 2.39 (s, 3H), 1.97-1.71 (m, 2H), 0.97-0.81 (m, 7H). |
| R61 | RACEMIC, N-(1-(2-(cyclopropanesulfonamido)thiazol-4-yl)propyl)-4-(pyridin-3-yl)benzamide | Method 1b, Using INTE10 and commercial acid, [HPLC acidic], 443, (1.2) | 12.58 (s, 1H), 9.00-8.96 (m, 1H), 8.72-8.66 (m, 1H), 8.63 (dd, J = 4.7, 1.6 Hz, 1H), 8.20-8.14 (m, 1H), 8.05-8.01 (m, 2H), 7.91-7.85 (m, 2H), 7.53 (dd, J = 7.9, 4.6 Hz, 1H), 6.55 (s, 1H), 4.95-4.83 (m, 1H), 2.64-2.55 (m, 1H), 1.98-1.71 (m, 2H), 0.99-0.81 (m, 7H). |
| R62 | RACEMIC, N-(1-(2-(cyclopropanesulfonamido)thiazol-4-yl)propyl)-4-(6-ethoxypyrazin-2-yl)-2-fluorobenzamide | Method 1a, Using INTE10 and INTF35, [HPLC Acidic], 506, (2.12) | 12.63 (s, 1H), 8.93 (s, 1H), 8.71 (d, J = 8.3 Hz, 1H), 8.33 (s, 1H), 8.11-8.01 (m, 2H), 7.79 (t, J = 7.8 Hz, 1H), 6.55 (s, 1H), 4.93-4.82 (m, 1H), 4.51 (q, J = 7.0 Hz, 2H), 2.62-2.55 (m, 1H), 1.94-1.81 (m, 1H), 1.81-1.66 (m, 1H), 1.42 (t, J = 7.0 Hz, 3H), 1.01-0.83 (m, 7H). |
| R63 | RACEMIC, N-(1-(2-(cyclopropanesulfonamido)thiazol-4-yl)propyl)-4-(6-ethoxypyrazin-2-yl)-2-fluoro-N-methylbenzamide | Method 1a, Using INTE11 and INTF35, [HPLC Acidic], 520, (2.22) | 12.75 (s, 1H), 8.90 (d, J = 5.1 Hz, 1H), 8.31 (d, J = 4.7 Hz, 1H), 8.15-7.98 (m, 2H), 7.69 (s, 1H), 6.73 (s, 1H), 5.50 (s, 1H), 4.53-4.47 (m, 2H), 2.66-2.62 (m, 4H), 2.11-1.74 (m, 2H), 1.45-1.35 (m, 3H), 0.99-0.84 (m, 7H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R64 | RACEMIC, N-(1-(2-(cyclopropanesulfonamido)thiazol-4-yl)propyl)-2-fluoro-4-(6-isopropoxypyrazin-2-yl)benzamide | Method 1a, Using INTE10 and INF36 [HPLC Acidic], 520, (2.24) | 12.62 (s, 1H), 8.90 (s, 1H), 8.70 (d, J = 8.3 Hz, 1H), 8.27 (s, 1H), 8.10-7.97 (m, 2H), 7.78 (t, J = 7.8 Hz, 1H), 6.54 (s, 1H), 5.45-5.33 (m, 1H), 4.87 (q, J = 7.9 Hz, 1H), 2.62-2.54 (m, 1H), 1.96-1.83 (m, 1H), 1.81-1.64 (m, 1H), 1.39 (d, J = 6.1 Hz, 6H), 0.98-0.80 (m, 7H). |
| R65 | RACEMIC, 4-(6-chloropyrazin-2-yl)-N-(1-(2-(cyclopropanesulfonamido)thiazol-4-yl)propyl)benzamide | Method 1b, Using INTE10 and INTF27 [HPLC acidic], 478 ³⁵Cl isotope, (1.91) | 12.60 (s, 1H), 9.38 (d, J = 0.6 Hz, 1H), 8.82 (s, 1H), 8.76 (d, J = 8.2 Hz, 1H), 8.31-8.20 (m, 2H), 8.07 (d, J = 8.4 Hz, 2H), 6.55 (s, 1H), 4.90 (q, J = 8.5, 7.9 Hz, 1H), 2.62-2.52 (m, 1H), 2.00-1.60 (m, 2H), 0.97-0.81 (m, 7H). |
| R66 | RACEMIC, N-(1-(2-(cyclopropanesulfonamido)thiazol-4-yl)propyl)-4-(6-methylpyrazin-2-yl)benzamide | Method 1b, Using INTE10 and INTF29 [HPLC Acidic], 458, (1.73) | 12.59 (s, 1H), 9.13 (s, 1H), 8.72 (d, J = 8.2 Hz, 1H), 8.56 (s, 1H), 8.28-8.21 (m, 2H), 8.07-8.00 (m, 2H), 6.56 (s, 1H), 4.94-4.84 (m, 1H), 2.62-2.50 (m, 4H), 2.01-1.67 (m, 2H), 0.96-0.85 (m, 7H). |
| R67 | RACEMIC, N-(1-(2-(cyclopropanesulfonamido)thiazol-4-yl)propyl)-4-(pyrazin-2-yl)benzamide | Method 1b, Using INTE10 and commercial acid, [HPLC Acidic], 444, (1.81) | 12.59 (s, 1H), 9.35 (d, J = 1.5 Hz, 1H), 8.77 (dd, J = 2.5, 1.5 Hz, 1H), 8.74 (d, J = 8.2 Hz, 1H), 8.67 (d, J = 2.4 Hz, 1H), 8.30-8.24 (m, 2H), 8.11-7.99 (m, 2H), 6.56 (s, 1H), 4.89 (q, J = 7.8 Hz, 1H), 2.62-2.54 (m, 1H), 1.98-1.72 (m, 2H), 0.96-0.79 (m, 7H). |
| R68 | SINGLE ENANTIOMER-stereochemistry unassigned, N-(1-(2-(cyclopropanesulfon-amido)thiazol-4-yl)propyl)-4-(5-fluoropyridin-3-yl)benzamide | Method 1b, Using INTE10 and INTF26, Separation using chiral method A, [UPLC acidic], 461, (1.13) Chiral IA method 1: Peak 1 RT 21.4 mins | 12.60 (s, 1H), 8.89 (t, J = 1.8 Hz, 1H), 8.72 (d, J = 8.3 Hz, 1H), 8.64 (d, J = 2.7 Hz, 1H), 8.21-8.16 (m, 1H), 8.08-8.02 (m, 2H), 7.99-7.92 (m, 2H), 6.56 (s, 1H), 4.90 (q, J = 8.2 Hz, 1H), 2.64-2.55 (m, 1H), 1.97-1.72 (m, 2H), 0.97-0.76 (m, 7H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R69 | SINGLE ENANTIOMER-stereochemistry unassigned, N-(1-(2-(cyclopropanesulfon-amido)thiazol-4-yl)propyl)-4-(5-fluoropyridin-3-yl)benzamide | Method 1b, Using INTE10 and INTF26, Separation using chiral method A [UPLC acidic], 461, (1.13) Chiral IA method 1: Peak 2 RT 27.5 mins | 12.60 (s, 1H), 8.89 (t, J = 1.8 Hz, 1H), 8.72 (d, J = 8.3 Hz, 1H), 8.64 (d, J = 2.7 Hz, 1H), 8.21-8.16 (m, 1H), 8.08-8.02 (m, 2H), 7.99-7.92 (m, 2H), 6.56 (s, 1H), 4.90 (q, J = 8.2 Hz, 1H), 2.64-2.55 (m, 1H), 1.97-1.72 (m, 2H), 0.97-0.76 (m, 7H). |
| R70 | SINGLE ENANTIOMER-stereochemistry unassigned, N-(1-(2-(cyclopropanesulfon-amido)thiazol-4-yl)propyl)-4-(6-ethoxypyrazin-2-yl)-2-fluorobenzamide | Chiral Sep, Method 1a, Using INTE10 and INTF35, Separation using chiral method B, [HPLC Acidic], 506, (2.11) Chiral IA method 2: Peak 1 RT 16.0 mins | 12.62 (s, 1H), 8.93 (s, 1H), 8.70 (dd, J = 8.3, 1.4 Hz, 1H), 8.32 (s, 1H), 8.11-8.03 (m, 2H), 7.80-7.73 (m, 1H), 6.55 (s, 1H), 4.93-4.79 (m, 1H), 4.50 (q, J = 7.0 Hz, 2H), 2.62-2.55 (m, 1H), 1.94-1.82 (m, 1H), 1.80-1.67 (m, 1H), 1.41 (t, J = 7.0 Hz, 3H), 0.98-0.85 (m, 7H). |
| R71 | SINGLE ENANTIOMER-stereochemistry unassigned, N-(1-(2-(cyclopropanesulfon-amido)thiazol-4-yl)propyl)-4-(6-ethoxypyrazin-2-yl)-2-fluorobenzamide | Chiral Sep, Method 1a, Using INTE10 and INTF35, Separation using chiral method B, [HPLC Acidic], 506, (2.12) Chiral IA method 2: Peak 2 RT 30.2 mins | 12.62 (s, 1H), 8.93 (s, 1H), 8.75-8.67 (m, 1H), 8.32 (s, 1H), 8.11-8.01 (m, 2H), 7.83-7.72 (m, 1H), 6.54 (s, 1H), 4.93-4.79 (m, 1H), 4.50 (q, J = 7.0 Hz, 2H), 2.62-2.55 (m, 1H), 1.94-1.81 (m, 1H), 1.79-1.64 (m, 1H), 1.41 (t, J = 7.0 Hz, 3H), 0.98-0.86 (m, 7H). |
| R72 | N-(2-(2-(cyclopropanesulfon-amido)-5-methylthiazol-4-yl)propan-2-yl)-5-(6-ethoxypyrazin-2-yl)picolinamide | Method 1a using INTE32 and INTF53, [HPLC Acidic], 503, (2.12) | 12.07 (s, 1H), 9.40 (d, J = 2.1 Hz, 1H), 9.00 (s, 1H), 8.70 (dd, J = 8.2, 2.2 Hz, 1H), 8.66 (s, 1H), 8.38 (s, 1H), 8.15 (d, J = 8.2 Hz, 1H), 4.52 (q, J = 7.0 Hz, 2H), 2.57-2.53 (m, 1H), 2.19 (s, 3H), 1.75 (s, 6H), 1.42 (t, J = 7.0 Hz, 3H), 0.94-0.79 (m, 4H). |
| R73 | N-(2-(5-chloro-2-(cyclopropane-sulfonamido)thiazol-4-yl)propan-2-yl)-5-(6-ethoxypyrazin-2-yl)picolinamide | Method 1a using INTE33 and INTF53, [HPLC Acidic], 523 ³⁵Cl isotope, (2.35) | 12.52 (s, 1H), 9.40 (d, J = 2.1 Hz, 1H), 9.00 (s, 1H), 8.74-8.67 (m, 2H), 8.38 (s, 1H), 8.15 (d, J = 8.1 Hz, 1H), 4.52 (q, J = 7.0 Hz, 2H), 2.71-2.65 (m, 1H), 1.78 (s, 6H), 1.42 (t, J = 7.0 Hz, 3H), 0.98-0.74 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | $^1$H NMR Chemical Shift Data (DMSO-d6 unless stated) |
|---|---|---|---|
| R74 | N-(2-(2-(cyclopropanesulfon-amido)-5-methylthiazol-4-yl)propan-2-yl)-4-(6-ethoxypyrazin-2-yl)-2-fluorobenzamide | Method 1a using INTE32 and INTF35, [HPLC Acidic], 520, (2.16) | 11.94 (s, 1H), 8.92 (s, 1H), 8.59-8.52 (m, 1H), 8.32 (s, 1H), 8.08-8.02 (m, 2H), 7.80-7.75 (m, 1H), 4.50 (q, J = 7.0 Hz, 2H), 2.62-2.53 (m, 1H), 2.22 (s, 3H), 1.66 (s, 6H), 1.41 (t, J = 7.0 Hz, 3H), 0.95-0.80 (m, 4H). |
| R75 | N-(2-(5-chloro-2-(cyclopropane-sulfonamido)thiazol-4-yl)propan-2-yl)-4-(6-ethoxypyrazin-2-yl)-2-fluorobenzamide | Method 1a using INTE33 and INTF35, [HPLC Acidic], 540 $^{35}$Cl isotope, (2.36) | 12.44 (s, 1H), 8.92 (s, 1H), 8.71 (d, J = 1.8 Hz, 1H), 8.33 (s, 1H), 8.11-8.00 (m, 2H), 7.89-7.66 (m, 1H), 4.50 (q, J = 7.0 Hz, 2H), 2.76-2.61 (m, 1H), 1.69 (s, 6H), 1.41 (t, J = 7.0 Hz, 3H), 1.02-0.90 (m, 4H). |
| R76 | N-(2-(2-(cyclopropanesulfon-amido)-5-methylthiazol-4-yl)propan-2-yl)-2-methyl-4-(6-(trifluoromethyl)pyrazin-2-yl)benzamide | Method 1a using INTE32 and INTF43, [HPLC Acidic], 540, (2.16) | 11.96 (s, 1H), 9.66 (s, 1H), 9.18 (s, 1H), 8.63 (s, 1H), 8.11-8.01 (m, 2H), 7.66-7.56 (m, 1H), 2.61-2.54 (m, 1H), 2.42 (s, 3H), 2.26 (s, 3H), 1.66 (s, 6H), 0.95-0.86 (m, 4H). |
| R77 | N-(2-(5-chloro-2-(cycloproane-sulfonamido)thiazol-4-yl)propan-2-yl)-2-methyl-4-(6-(trifluoromethyl)pyrazin-2-yl)benzamide | Method 1a using INTE33 and INTF43, [HPLC Acidic], 560 $^{35}$Cl isotope, (2.33) | 12.45 (s, 1H), 9.66 (s, 1H), 9.18 (s, 1H), 8.79 (s, 1H), 8.18-7.97 (m, 2H), 7.70-7.49 (m, 1H), 2.70-2.66 (m, 1H), 2.43 (s, 3H), 1.69 (s, 6H), 1.02-0.92 (m, 4H). |
| R78 | N-(2-(2-(cyclopropanesulfon-amido)-5-methylthiazol-4-yl)propan-2-yl)-4-(6-(trifluoromethyl)pyrazin-2-yl)benzamide | Method 1a using INTE32 and INTF28, [HPLC Acidic], 526, (2.19) | 11.98 (s, 1H), 9.71 (s, 1H), 9.21 (s, 1H), 8.59 (s, 1H), 8.33-8.27 (m, 2H), 8.12-8.02 (m, 2H), 2.60-2.54 (m, 1H), 2.18 (s, 3H), 1.69 (s, 6H), 0.92-0.84 (m, 4H). |
| R79 | N-(2-(5-chloro-2-(cyclopropane-sulfonamido)thiazol-4-yl)propan-2-yl)-4-(6-(trifluoromethyl)pyrazin-2-yl)benzamide | Method 1a using INTE33 and INTF28, [HPLC Acidic], 546 $^{35}$Cl isotope, (2.29) | 12.47 (s, 1H), 9.71 (s, 1H), 9.21 (s, 1H), 8.74 (s, 1H), 8.39-8.25 (m, 2H), 8.15-7.98 (m, 2H), 2.69-2.64 (m, 1H), 1.72 (s, 6H), 0.97-0.90 (m, 4H). |

TABLE 6-continued

*The following final compounds were made according to general methods*

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R80 | N-(1-(2-(cyclopropanesulfon-amido)thiazol-4-yl)cyclo-propyl)-5-(6-ethoxypyrazin-2-yl)picolinamide | Method 1a using INTE38 and INTF53, [HPLC Acidic], 487, (1.97) | 12.41 (s, 1H), 9.40-9.32 (m, 2H), 9.00 (s, 1H), 8.69 (dd, J = 8.2, 2.2 Hz, 1H), 8.38 (s, 1H), 8.16 (d, J = 8.2 Hz, 1H), 6.44 (s, 1H), 4.52 (q, J = 7.0 Hz, 2H), 2.61-2.53 (m, 1H), 1.42 (t, J = 7.0 Hz, 3H), 1.40-1.34 (m, 2H), 1.29-1.23 (m, 2H), 0.93-0.83 (m, 4H). |
| R81 | N-(1-(2-(cyclopropanesulfon-amido)thiazol-4-yl)cyclo-propyl)-4-(pyridin-3-yl)benzamide | Method 1a using INTE38 and Commercial acid, [UPLC Basic], 441, (0.77) | 12.32 (s, 1H), 9.14 (s, 1H), 8.97 (d, J = 2.4 Hz, 1H), 8.62 (dd, J = 4.8, 1.6 Hz, 1H), 8.18-8.15 (m, 1H), 8.06-7.95 (m, 2H), 7.94-7.77 (m, 2H), 7.53 (dd, J = 7.9, 4.8 Hz, 1H), 6.40 (s, 1H), 2.62-2.54 (m, 1H), 1.43-1.34 (m, 2H), 1.29-1.21 (m, 2H), 0.98-0.78 (m, 4H). |
| R82 | N-(1-(2-(cyclopropanesulfon-amido)thiazol-4-yl)cyclo-propyl)-4-(6-ethoxypyrazin-2-yl)-2-fluorobenzamide | Method 1a using INTE38 and INTF35, [HPLC Acidic], 504, (2.05) | 12.32 (s, 1H), 9.02 (s, 1H), 8.94 (s, 1H), 8.33 (s, 1H), 8.12-8.00 (m, 2H), 7.86-7.78 (m, 1H), 6.44 (s, 1H), 4.51 (q, J = 7.0 Hz, 2H), 2.63-2.54 (m, 1H), 1.46-1.33 (m, 5H), 1.25-1.15 (m, 2H), 0.96-0.85 (m, 4H). |
| R83 | N-(1-(2-(cyclopropanesulfon-amido)thiazol-4-yl)cyclopropyl)-2-methyl-4-(6-(trifluoromethyl)pyrazin-2-yl)benzamide | Method 1a using INTE38 and INTF43, [HPLC Acidic], 524, (2.08) | 12.31 (s, 1H), 9.67 (s, 1H), 9.18 (s, 1H), 9.04 (s, 1H), 8.10-8.07 (m, 2H), 7.67 (d, J = 7.9 Hz, 1H), 6.47 (s, 1H), 2.63-2.57 (m, 1H), 2.44 (s, 3H), 1.43-1.34 (m, 2H), 1.25-1.18 (m, 2H), 1.00-0.81 (m, 4H). |
| R84 | N-(1-(2-(cyclopropanesulfon-amido)thiazol-4-yl)cyclopropyl)-4-(6-(trifluoromethyl)pyrazin-2-yl)benzamide | Method 1a using INTE38 and INTF28, [HPLC Acidic], 510, (2.04) | 12.37 (s, 1H), 9.72 (s, 1H), 9.29-9.06 (m, 2H), 8.39-8.28 (m, 2H), 8.15-7.96 (m, 2H), 6.40 (s, 1H), 2.61-2.54 (m, 1H), 1.42-1.35 (m, 2H), 1.32-1.22 (m, 2H), 0.96-0.84 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R85 | N-(1-(2-(cyclopropanesulfon-amido)thiazol-4-yl)-3-methoxypropyl)-4-(5-fluoropyridin-3-yl)benzamide | Method 1a using INTE39 and INTF26, [UPLC Acidic], 491, (1.09) | 12.60 (s, 1H), 8.89 (t, J = 1.9 Hz, 1H), 8.74 (d, J = 8.1 Hz, 1H), 8.64 (d, J = 2.7 Hz, 1H), 8.21-8.15 (m, 1H), 8.09-7.98 (m, 2H), 7.98-7.91 (m, 2H), 6.57 (s, 1H), 5.13-5.02 (m, 1H), 3.46-3.34 (m, 2H), 3.23 (s, 3H), 2.62-2.54 (m, 1H), 2.18-2.10 (m, 1H), 2.07-1.98 (m, 1H), 0.95-0.85 (m, 4H). |
| R86 | N-(1-(2-(cyclopropanesulfon-amido)thiazol-4-yl)-3-methoxypropyl)-4-(6-ethyl-pyrazin-2-yl)-2-fluorobenzamide | Method 1a using INTE39 and INTF39, [UPLC Acidic], 520, (1.24) | 12.64 (s, 1H), 9.18 (s, 1H), 8.71 (d, J = 8.2 Hz, 1H), 8.62 (s, 1H), 8.14-8.05 (m, 2H), 7.87-7.77 (m, 1H), 6.57 (s, 1H), 5.12-5.03 (m, 1H), 3.46-3.37 (m, 2H), 3.25 (s, 3H), 2.90 (q, J = 7.6 Hz, 2H), 2.63-2.55 (m, 1H), 2.18-2.05 (m, 1H), 2.05-1.91 (m, 1H), 1.33 (t, J = 7.6 Hz, 3H), 0.97-0.83 (m, 4H). |
| R87 | N-(1-(2-(cyclopropanesulfon-amido)thiazol-4-yl)-3-methoxypropyl)-2-fluoro-4-(6-(trifluoromethyl)pyrazin-2-yl)benzamide | Method 1a using INTE39 and INTF34, [UPLC Acidic], 560, (1.33) | 12.65 (s, 1H), 9.73 (s, 1H), 9.24 (s, 1H), 8.78 (d, J = 8.0 Hz, 1H), 8.21-8.12 (m, 2H), 7.92-7.83 (m, 1H), 6.57 (s, 1H), 5.12-5.03 (m, 1H), 3.49-3.36 (m, 2H), 3.25 (s, 3H), 2.64-2.55 (m, 1H), 2.19-2.07 (m, 1H), 2.05-1.92 (m, 1H), 0.98-0.83 (m, 4H). |
| R88 | N-(1-(2-(cyclopropanesulfon-amido)thiazol-4-yl)-3-methoxypropyl)-4-(6-ethoxypyrazin-2-yl)-2-fluorobenzamide | Method 1a using INTE39 and INTF35, [HPLC Acidic], 536, (2.08) | 12.63 (s, 1H), 8.93 (s, 1H), 8.66 (s, 1H), 8.33 (s, 1H), 8.11-8.03 (m, 2H), 7.85-7.73 (m, 1H), 6.52 (s, 1H), 5.13-4.96 (m, 1H), 4.51 (q, J = 7.0 Hz, 2H), 3.47-3.37 (m, 2H), 3.25 (s, 3H), 2.60-2.52 (m, 1H), 2.18-2.08 (m, 1H), 2.02-1.81 (m, 1H), 1.42 (t, J = 7.0 Hz, 3H), 0.99-0.65 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R89 | N-(1-(2-(cyclopropanesulfon-amido)thiazol-4-yl)-3-methoxypropyl)-2-fluoro-4-(6-isopropoxypyrazin-2-yl)benzamide | Method 1a using INTE39 and INTF36, [UPLC Acidic], 551, (1.42) | 12.64 (s, 1H), 8.91 (s, 1H), 8.71 (d, J = 9.1 Hz, 1H), 8.28 (s, 1H), 8.11-8.02 (m, 2H), 7.85-7.78 (m, 1H), 6.55 (s, 1H), 5.43 (h, J = 6.2 Hz, 1H), 5.12-5.03 (m, 1H), 3.47-3.38 (m, 2H), 3.25 (s, 3H), 2.63-2.56 (m, 1H), 2.17-2.10 (m, 1H), 2.03-1.93 (m, 1H), 1.40 (d, J = 6.2 Hz, 6H), 0.96-0.85 (m, 4H). |
| R90 | N-(1-(2-(cyclopropanesulfon-amido)thiazol-4-yl)-3-methoxypropyl)-4-(6-ethoxy-pyrazin-2-yl)benzamide | Method 1a using INTE39 and INTF37, [UPLC Acidic], 519, (1.27) | 12.61 (s, 1H), 8.91 (s, 1H), 8.74 (d, J = 8.1 Hz, 1H), 8.30 (s, 1H), 8.28-8.22 (m, 2H), 8.07-8.00 (m, 2H), 6.58 (s, 1H), 5.12-5.04 (m, 1H), 4.51 (q, J = 7.0 Hz, 2H), 3.46-3.35 (m, 2H), 3.23 (s, 3H), 2.63-2.55 (m, 1H), 2.18-2.09 (m, 1H), 2.09-1.99 (m, 1H), 1.42 (t, J = 7.0 Hz, 3H), 0.95-0.86 (m, 4H). |
| R91 | N-(1-(2-(cyclopropanesulfon-amido)thiazol-4-yl)ethyl)-4-(6-ethoxypyrazin-2-yl)-2-fluorobenzamide | Method 1a using INTE23 and INTF35, [HPLC Acidic], 492, (2.02) | 12.66 (s, 1H), 8.93 (s, 1H), 8.81 (d, J = 7.7 Hz, 1H), 8.33 (s, 1H), 8.09-8.01 (m, 2H), 7.84-7.73 (m, 1H), 6.54 (s, 1H), 5.06-4.96 (m, 1H), 4.51 (q, J = 7.0 Hz, 2H), 2.63-2.53 (m, 1H), 1.46 (d, J = 6.9 Hz, 3H), 1.42 (t, J = 7.0 Hz, 3H), 0.94-0.85 (m, 4H). |
| R92 | SINGLE ENANTIOMER-stereochemistry unassigned N-(1-(2-(cyclopropanesulfon-amido)thiazol-4-yl)-3-methoxypropyl)-4-(6-ethoxypyrazin-2-yl)-2-fluorobenzamide | Method 1a using INTE39 and INTF35, Chiral IC1 (17.4), [HPLC Acidic], 536, (2.08) | 12.64 (s, 1H), 8.94 (s, 1H), 8.74-8.67 (m, 1H), 8.33 (s, 1H), 8.15-7.99 (m, 2H), 7.86-7.72 (m, 1H), 6.58 (s, 1H), 5.16-5.02 (m, 1H), 4.51 (q, J = 7.0 Hz, 2H), 3.49-3.33 (m, 2H), 3.25 (s, 3H), 2.64-2.57 (m, 1H), 2.22-2.05 (m, 1H), 2.05-1.92 (m, 1H), 1.42 (t, J = 7.0 Hz, 3H), 0.97-0.81 (m, 4H). |

TABLE 6-continued

The following final compounds were made according to general methods

| R | Name/Structure (All examples containing chiral centres are racemic unless stated) | Synthesis Method, [LCMS Method], m/z (M + H)+, (RT/Min) | ¹H NMR Chemical Shift Data (DMSO-d6 unless stated) |
|---|---|---|---|
| R93 | SINGLE ENANTIOMER-stereochemistry unassigned N-(1-(2-(cyclopropanesulfon-amido)thiazol-4-yl)-3-methoxypropyl)-4-(6-ethoxypyrazin-2-yl)-2-fluorobenzamide | Method 1a using INTE39 and INTF35, Chiral IC1 (22.7), [HPLC Acidic], 536, (2.08) | 12.64 (s, 1H), 8.94 (s, 1H), 8.79-8.67 (m, 1H) 8.33 (s, 1H), 8.18-8.03 (m, 2H), 7.89-7.73 (m, 1H), 6.57 (s, 1H), 5.16-5.02 (m, 1H),, 4.51 (q, J = 7.0 Hz, 2H), 3.46-3.37 (m, 2H), 3.25 (s, 3H), 2.63-2.56 (m, 1H), 2.21-2.04 (m, 1H), 2.02-1.91 (m, 1H), 1.42 (t, J = 7.0 Hz, 3H), 0.96-0.80 (m, 4H). |

BIOLOGICAL EXAMPLES

Biological Example 1—Human CTPS1 Enzyme Inhibition

The enzyme inhibitory activities of compounds invented against the target of interest were determined using the ADP-Glo™ Max assay (Promega, UK). Assays for human CTPS1 were performed in 1× assay buffer containing 50 mM Tris, 10 mM MgCl$_2$, 0.01% Tween-20, pH to 8.0 accordingly. Finally, immediately before use, L-cysteine was added to the 1×assay buffer to a final concentration of 2 mM. All reagents are from Sigma-Aldrich unless specified otherwise. Human full length active C-terminal FLAG-Hiss-tag CTPS1 (UniProtKB—P17812, CTPS[1-591]-GGDYKDDDDKGGHHHHHHHH) was obtained from Proteros biostructures GmbH.

Assay Procedure

3× human CTPS1 protein was prepared in 1× assay buffer to the final working protein concentration required for the reaction. A 2 uL volume per well of 3× human CTPS1 protein was mixed with 2 uL per well of 3× test compound (compound prepared in 1× assay buffer to an appropriate final 3× compound concentration respective to the concentration response curve designed for the compounds under test) for 10 minutes at 25° C. The enzymatic reaction was then initiated by addition of a 2 uL per well volume of a pre-mixed substrate mix (UltraPure ATP from ADP-Glo™ Max kit (0.31 mM), GTP (0.034 mM), UTP (0.48 mM) and L-glutamine (0.186 mM)) and the mixture was incubated for an appropriate amount of time within the determined linear phase of the reaction at 25° C. under sealed plate conditions with constant agitation at 500 revolutions per minute (rpm). ADP-Glo™ Max reagent was added for 60 minutes (6 uL per well) and subsequently ADP-Glo™ Max development reagent was added for 60 minutes (12 uL per well) prior to signal detection in a microplate reader (EnVision® Multi-label Reader, Perkin Elmer). Following each reagent addition over the course of the assay, assay plates were pulse centrifuged for 30 seconds at 500 rpm.

In all cases, the enzyme converts ATP to ADP and the ADP-Glo™ Max reagent subsequently depletes any remaining endogenous ATP in the reaction system. The ADP-Glo™ Max detection reagent converts the ADP that has been enzymatically produced back into ATP and using ATP as a substrate together with luciferin for the enzyme luciferase, light is generated which produces a detectable luminescence. The luminescent signal measured is directly proportional to the amount of ADP produced by the enzyme reaction and a reduction in this signal upon compound treatment demonstrates enzyme inhibition. The percentage inhibition produced by each concentration of compound was calculated using the equation shown below:

$$\% \text{ Inhibition} = 1 - \frac{(Mean_{Min} - Mean_{inh})}{(Mean_{Min} - Mean_{Max})} \times 100$$

Percentage inhibition was then plotted against compound concentration, and the 50% inhibitory concentration (IC$_{50}$) was determined from the resultant concentration-response curve.

TABLE 7

Human CTPS1 Enzyme Inhibition data grouped by potency range
(± indicates IC$_{50}$ in the range of >10 to 21 micromolar,
+ indicates IC$_{50}$ in the range >1 to 10 micromolar,
++ indicates IC$_{50}$ in the range >0.1 to 1 micromolar,
+++ indicates IC$_{50}$ of <0.1 micromolar)

| R | CTPS1 |
|---|---|
| R1 | ++ |
| R2 | ++ |
| R3 | ++ |
| R4 | +++ |
| R5 | +++ |
| R6 | +++ |
| R7 | ++ |
| R8 | + |
| R9 | + |
| R10 | +++ |
| R11 | +++ |
| R12 | +++ |
| R13 | +++ |
| R14 | +++ |
| R15 | +++ |
| R16 | ++ |
| R17 | ++ |
| R18 | ++ |
| R19 | +++ |
| R20 | +++ |
| R21 | +++ |
| R22 | ++ |

TABLE 7-continued

Human CTPS1 Enzyme Inhibition data grouped by potency range
(± indicates IC$_{50}$ in the range of >10 to 21 micromolar,
+ indicates IC$_{50}$ in the range >1 to 10 micromolar,
++ indicates IC$_{50}$ in the range >0.1 to 1 micromolar,
+++ indicates IC$_{50}$ of <0.1 micromolar)

| R | CTPS1 |
|---|---|
| R23 | ++ |
| R24 | ++ |
| R25 | ++ |
| R26 | ++ |
| R27 | ± |
| R28 | +++ |
| R29 | +++ |
| R30 | ++ |
| R31 | ++ |
| R32 | ++ |
| R33 | + |
| R34 | + |
| R35 | +++ |
| R36 | ++ |
| R37 | +++ |
| R38 | ++ |
| R39 | ++ |
| R40 | ++ |
| R41 | ++ |
| R42 | +++ |
| R43 | +++ |
| R44 | ++ |
| R45 | ++ |
| R46 | ++ |
| R47 | ++ |
| R48 | ++ |
| R49 | ++ |
| R50 | + |
| R51 | +++ |
| R52 | +++ |
| R53 | ++ |
| R54 | +++ |
| R55 | +++ |
| R56 | +++ |
| R57 | ++ |
| R58 | ++ |
| R59 | ++ |
| R60 | ++ |
| R61 | ++ |
| R62 | ++ |
| R63 | ++ |
| R64 | ++ |
| R65 | +++ |
| R66 | ++ |
| R67 | ++ |
| R68 | + |
| R69 | +++ |
| R70 | ++ |
| R71 | +++ |
| R72 | + |
| R73 | + |
| R74 | ++ |
| R75 | ++ |
| R76 | ++ |
| R77 | + |
| R78 | ++ |
| R79 | ++ |
| R80 | +++ |
| R81 | ++ |
| R82 | +++ |
| R83 | +++ |
| R84 | +++ |
| R85 | ++ |
| R86 | ++ |
| R87 | ++ |
| R88 | ++ |
| R89 | +++ |
| R90 | +++ |
| R91 | +++ |
| R92 | +++ |
| R93 | +++ |

Biological Example 2—RapidFire/MS-based Enzyme Selectivity Assays

Human CTPS1 Versus CTPS2 Selectivity Assessment by RapidFire/MS Analysis.

The enzyme inhibitory activities against each target isoform of interest were determined for the compounds of the invention using an optimised RapidFire high-throughput mass spectrometry (RF/MS) assay format. RF/MS assays for both human CTPS1 and CTPS2 were performed in assay buffer consisting of 50 mM HEPES (Merck), 20 mM MgCl$_2$, 5 mM KCl, 1 mM DTT, 0.01% Tween-20, pH to 8.0 accordingly. All reagents were from Sigma-Aldrich unless specified otherwise. Human full-length active C-terminal FLAG-His-tag CTPS1 (UniProtKB—P17812, CTPS[1-591]-GGDYKDDDDKGGHHHHHHHH) was obtained from Proteros biostructures GmbH. Human full length active C-terminal FLAG-His-Avi tagged CTPS2 (UniProtKB—Q9NRF8, CTPS2 [1-586]-DYKDDDDKHHHHHHGLNDIFEAQKIEWHE) was obtained from Harker Bio.

Assay Procedure

Human CTPS (1 or 2) protein was prepared in 1× assay buffer to the final working protein concentration required for the reaction. A 2 uL volume per well of 2×CTPS (1 or 2) protein was mixed with 40 nL of compound using acoustic (ECHO) delivery and incubated for 10 minutes at 25° C. Each isoform enzymatic reaction was subsequently initiated by addition of 2 uL per well of a 2× substrate mix in assay buffer. For hCTPS1: ATP (0.3 mM), UTP (0.2 mM), GTP (0.07 mM) and L-glutamine (0.1 mM). For hCTPS2: ATP (0.1 mM), UTP (0.04 mM), GTP (0.03 mM) and L-glutamine (0.1 mM). Each mixture was incubated for an appropriate amount of time per isoform within the determined linear phase of the reaction at 25° C. A 60 uL volume of stop solution (1% formic acid with 0.5 uM $^{13}C_9$-$^{15}N_3$-CTP in H$_2$O) was added and the plate immediately heat-sealed and centrifuged for 10 minutes at 4,000 rpm. Following centrifugation, plates were loaded onto the Agilent RapidFire microfluidic solid phase extraction system coupled to an API4000 triple quadrupole mass spectrometer (RF/MS) for analysis.

In all cases, the enzyme converts UTP to CTP. Highly specific and sensitive multiple reaction monitoring (MRM) MS methods were optimised for the detection of the enzymatic reaction product, CTP, and the stable isotope labelled product standard $^{13}C_9$-$^{15}N_3$-CTP. Readout for data analysis was calculated as the ratio between the peak area of the product CTP and the internal standard $^{13}C_9$-$^{15}N_3$-CTP. For data reporting, the following equation was used:

$$R = \frac{P}{IS}$$

(R=ratio/readout, P=product signal area, IS=internal standard signal area)

For each screening plate, the means of the negative (DMSO) and positive control values were used for the calculation of the respective assay window (S/B) and Z' values. The median of the respective control values was used for calculation of percent inhibition according to the following equation:

$$I = \frac{R_{neg} - R_{sample}}{[R_{neg} - R_{pos}]} \%$$

(I=Inhibition, $R_{neg}$=median of negative control readout values, $R_{pos}$=median of positive control readout values, $R_{sample}$=sample readout value)

Percentage inhibition was then plotted against compound concentration, and the 50% inhibitory concentration ($IC_{50}$) was determined from the resultant concentration-response curve.

Fold selectivity between CTPS1 and CTPS2 was subsequently calculated according to the following equation:

$$\text{Fold selectivity} = \frac{CTPS2\ IC_{50}}{CTPS1\ IC_{50}}$$

Certain compounds were tested in the assay above. The data for all compounds tested are presented below.

TABLE 8

Selectivity data split into grouping of 2-30 fold (+), >30-60 fold (++) or >60 fold (+++)

| R | Selectivity |
|---|---|
| R5 | + |
| R6 | ++ |
| R7 | ++ |
| R11 | ++ |
| R19 | ++ |
| R23 | ++ |
| R25 | ++ |
| R26 | +++ |
| R41 | ++ |
| R42 | ++ |
| R43 | ++ |
| R45 | ++ |
| R46 | + |
| R47 | + |
| R48 | ++ |
| R51 | ++ |
| R52 | +++ |
| R54 | + |
| R55 | +++ |
| R56 | +++ |
| R62 | +++ |
| R63 | + |
| R64 | ++ |
| R68 | ++ |
| R69 | +++ |
| R70 | +++ |
| R71 | +++ |
| R73 | + |
| R74 | ++ |
| R75 | +++ |
| R76 | + |
| R78 | ++ |
| R79 | + |
| R80 | +++ |
| R82 | +++ |
| R83 | +++ |
| R84 | +++ |
| R86 | +++ |
| R87 | ++ |
| R88 | +++ |
| R89 | +++ |
| R90 | ++ |
| R91 | +++ |
| R92 | +++ |
| R93 | +++ |

All compounds of the invention which have been tested were found to demonstrate inhibition of CTPS1 enzyme in this assay. Consequently, these compounds may be expected to have utility in the inhibition of CTPS1.

All compounds tested in the assay described in Biological Assay 2 were found to have at least 2 fold selectivity for CTPS1 over CTPS2, with many compounds having a selectivity for CTPS1 of over 60 fold. In particular, these compounds may be expected to have utility in the treatment of diseases whereby a selective CTPS1 compound is beneficial.

The compounds of the invention are also expected to have utility as research tools, for example, for use in CTPS assays.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

All publications, including but not limited to patents and patent applications, cited in this specification are herein incorporated by reference as if each individual publication were specifically and individually indicated to be incorporated by reference herein as though fully set forth.

Clauses of the Invention

Clause 1. A compound of formula (I):

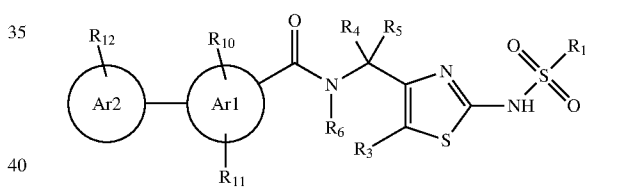

wherein
$R_1$ is $C_{1-5}$alkyl, $C_{0-2}$alkylene$C_{3-5}$cycloalkyl which cycloalkyl is optionally substituted by $CH_3$, $C_{1-3}$alkyleneOC$_{1-2}$alkyl, or $CF_3$;
$R_3$ is H, $CH_3$, halo, $OC_{1-2}$alkyl or $CF_3$;
$R_4$ and $R_5$ are each independently H, $C_{1-6}$alkyl, $C_{0-2}$alkylene$C_{3-6}$cycloalkyl, $C_{0-2}$alkylene$C_{3-6}$heterocycloalkyl, $C_{1-3}$alkyleneOC$_{1-3}$alkyl, $C_{1-6}$alkylOH or $C_{1-6}$haloalkyl,
or $R_4$ and $R_5$ together with the carbon atom to which they are attached form a $C_{3-6}$cycloalkyl or $C_{3-6}$heterocycloalkyl ring;
$R_6$ is H or $C_{1-3}$alkyl;
Ar1 is a 6-membered aryl or heteroaryl;
Ar2 is a 6-membered aryl or heteroaryl and is attached to Ar1 in the para position relative to the amide;
$R_{10}$ is H, halo, $C_{1-3}$alkyl, $OC_{1-2}$alkyl, $C_{1-2}$haloalkyl, $OC_{1-2}$ haloalkyl or CN;
$R_{11}$ is H, F, $C_1$, $CH_3$, ethyl, $OCH_3$, $CF_3$, $OCF_3$ or CN;
$R_{12}$ is attached to Ar2 in the meta or ortho position relative to Ar1 and $R_{12}$ is H, halo, $C_{1-4}$alkyl, $C_{2-4}$alkynyl, C(=O)$C_{1-2}$alkyl, $C_{0-2}$alkylene$C_{3-5}$cycloalkyl, $OC_{1-4}$alkyl, $C_{1-3}$alkyleneOC$_{1-3}$alkyl, $C_{1-4}$haloalkyl, $OC_{1-4}$haloalkyl, CN, $OC_{0-2}$alkylene$C_{3-5}$cycloalkyl, $OCH_2CH_2N(CH_3)_2$, OH, $C_{1-4}$alkylOH, $NR_{23}R_{24}$, SO$_2$CH$_3$, C(O)N(CH$_3$)$_2$, NHC(O)C$_{1-3}$alkyl, or a C$_{3-6}$heterocycloalkyl comprising one nitrogen located at the point of attachment to Ar2, or R$_{12}$ together with a nitrogen atom to which it is attached forms an N-oxide (N$^+$—O$^-$);

R$_{23}$ is H or C$_{1-2}$alkyl; and

R$_{24}$ is H or C$_{1-2}$alkyl;

or a salt and/or solvate thereof and/or derivative thereof.

Clause 2. The compound according to clause 1 which is a compound of formula (I):

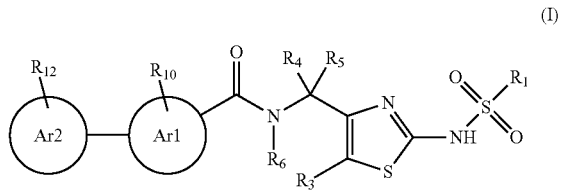

(I)

wherein

R$_1$ is C$_{1-4}$alkyl, C$_{1-2}$alkyleneOC$_{1-2}$alkyl or C$_{0-1}$alkyleneC$_{3-4}$cycloalkyl which cycloalkyl is optionally substituted by CH$_3$;

R$_3$ is H, CH$_3$, F or Cl;

R$_4$ and R$_5$ are each independently H, C$_{1-4}$alkyl, C$_{0-2}$alkyleneC$_{3-5}$cycloalkyl, C$_{1-3}$alkyleneOC$_{1-3}$alkyl, C$_{1-4}$alkylOH or C$_{1-4}$haloalkyl;

R$_6$ is H or C$_{1-3}$alkyl;

Ar1 is a 6-membered aryl or heteroaryl;

Ar2 is a 6-membered aryl or heteroaryl and is attached to Ar1 in the para position relative to the amide;

R$_{10}$ is H, halo, C$_{1-3}$alkyl, OC$_{1-2}$alkyl, C$_{1-2}$haloalkyl, OC$_{1-2}$haloalkyl or CN; and R$_{12}$ is attached to Ar2 in the meta position relative to Ar1 and R$_{12}$ is H, halo, C$_{1-4}$alkyl, C$_2$alkynyl, C(=O)C$_{1-2}$alkyl, C$_{0-2}$alkyleneC$_{3-5}$cycloalkyl, OC$_{1-4}$alkyl, C$_{1-3}$alkyleneOC$_{1-3}$alkyl, C$_{1-4}$haloalkyl, OC$_{1-4}$haloalkyl or CN; or a salt and/or solvate thereof and/or derivative thereof.

Clause 3. The compound according to clause 1 which is a compound of formula (I):

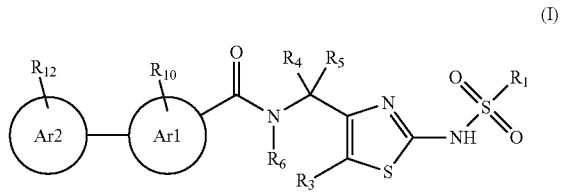

(I)

wherein

R$_1$ is C$_{0-1}$alkyleneC$_{3-4}$cycloalkyl;

R$_3$ is H, CH$_3$ or C$_1$;

R$_4$ and R$_5$ are each independently H, C$_{1-4}$alkyl or C$_{1-3}$alkyleneOC$_{1-3}$alkyl;

or R$_4$ together with R$_5$ form a C$_{3-6}$cycloalkyl ring

R$_6$ is H or C$_{1-3}$alkyl;

Ar1 is a 6-membered aryl or heteroaryl;

Ar2 is a 6-membered aryl or heteroaryl and is attached to Ar1 in the para position relative to the amide;

R$_{10}$ is H, halo, C$_{1-3}$alkyl, OC$_{1-2}$alkyl or C$_{1-2}$haloalkyl; and

R$_{12}$ is attached to Ar2 in the meta position relative to Ar1 and R$_{12}$ is H, halo, C$_{1-4}$alkyl, C(=O)C$_{1-2}$alkyl, OC$_{1-4}$alkyl, C$_{1-4}$haloalkyl, OC$_{1-4}$haloalkyl or CN; or a salt and/or solvate thereof and/or derivative thereof.

Clause 4. The compound according to any one of clauses 1 to 3 wherein R$_1$ is C$_{1-5}$alkyl.

Clause 5. The compound according to clause 4 wherein R$_1$ is C$_{1-4}$alkyl.

Clause 6. The compound according to any one of clauses 1 to 3 wherein R$_1$ is C$_{1-3}$alkyleneOC$_{1-2}$alkyl.

Clause 7. The compound according to any one of clauses 1 to 3 wherein R$_1$ is C$_{1-2}$alkyleneOC$_{1-2}$alkyl.

Clause 8. The compound according to any one of clauses 1 to 3 wherein R$_1$ is C$_{0-2}$alkyleneC$_{3-5}$cycloalkyl which cycloalkyl is optionally substituted by CH$_3$.

Clause 9. The compound according to clause 8 wherein R$_1$ is C$_{0-1}$alkyleneC$_{3-4}$cycloalkyl which cycloalkyl is optionally substituted by CH$_3$.

Clause 10. The compound according to clause 9 wherein R$_1$ is C$_{0-1}$alkyleneC$_{3-4}$cycloalkyl.

Clause 11. The compound according to any one of clauses 9 or 10 wherein R$_1$ is C$_3$-4cycloalkyl.

Clause 12. The compound according to clause 11 wherein R$_1$ is cyclopropyl.

Clause 13. The compound according to clause 9 wherein R$_1$ is C$_{0-1}$alkyleneC$_{3-4}$cycloalkyl which cycloalkyl is substituted by CH$_3$.

Clause 14. The compound according to any one of clauses 1 to 13 wherein R$_3$ is H.

Clause 15. The compound according to any one of clauses 1 to 13 wherein R$_3$ is Me.

Clause 16. The compound according to any one of clauses 1 to 13 wherein R$_3$ is halo.

Clause 17. The compound according to clause 16 wherein R$_3$ is F.

Clause 18. The compound according to clause 16 wherein R$_3$ is Cl.

Clause 19. The compound according to any one of clauses 1 to 13 wherein R$_3$ is OC$_{1-2}$alkyl.

Clause 20. The compound according to any one of clauses 1 to 13 wherein R$_3$ is OCF$_3$.

Clause 21. The compound according to any one of clauses 1 to 13 wherein R$_3$ is CF$_3$.

Clause 22. The compound according to any one of clauses 1 to 21 wherein R$_4$ is H.

Clause 23. The compound according to any one of clauses 1 to 21 wherein R$_4$ is C$_{1-6}$alkyl.

Clause 24. The compound according to clause 23 wherein R$_4$ is C$_{1-4}$alkyl.

Clause 25. The compound according to clause 24 wherein R$_4$ is methyl or ethyl.

Clause 26. The compound according to any one of clauses 1 to 21 wherein R$_4$ is C$_{0-2}$alkyleneC$_{3-6}$cycloalkyl.

Clause 27. The compound according to clause 26 wherein R$_4$ is C$_{0-2}$alkyleneC$_{3-5}$cycloalkyl.

Clause 28. The compound according to any one of clauses 1 to 21 wherein R$_4$ is C$_{1-3}$alkyleneOC$_{1-3}$alkyl such as CH$_2$CH$_2$OCH$_3$.

Clause 29. The compound according to any one of clauses 1 to 21 wherein R$_4$ is C$_{0-2}$alkyleneC$_{3-6}$heterocycloalkyl.

Clause 30. The compound according to any one of clauses 1 to 21 wherein R$_4$ is C$_{1-6}$alkylOH.

Clause 31. The compound according to clause 30 wherein R$_4$ is C$_{1-4}$alkylOH.

Clause 32. The compound according to clause 1 to 21 wherein R$_4$ is C$_{1-6}$haloalkyl.

Clause 33. The compound according to clause 32 wherein R$_4$ is C$_{1-4}$haloalkyl.

Clause 34. The compound according to any one of clauses 1 to 33 wherein $R_5$ is H.

Clause 35. The compound according to any one of clauses 1 to 33 wherein $R_5$ is $C_{1-6}$alkyl.

Clause 36. The compound according to clause 35 wherein $R_5$ is $C_{1-4}$alkyl.

Clause 37. The compound according to clause 36 wherein $R_5$ is methyl or ethyl.

Clause 38. The compound according to any one of clauses 1 to 33 wherein $R_5$ is $C_0$-2alkylene$C_{3-6}$cycloalkyl.

Clause 39. The compound according to clause 38 wherein $R_5$ is $C_{0-2}$alkylene$C_{3-5}$cycloalkyl.

Clause 40. The compound according to any one of clauses 1 to 33 wherein $R_5$ is $C_{0-2}$alkylene$C_{3-6}$heterocycloalkyl.

Clause 41. The compound according to any one of clauses 1 to 33 wherein $R_5$ is $C_{1-3}$alkyleneO$C_{1-3}$alkyl such as $CH_2CH_2OCH_3$.

Clause 42. The compound according to any one of clauses 1 to 33 wherein $R_5$ is $C_1$-6alkylOH.

Clause 43. The compound according to clause 42 wherein $R_5$ is $C_{1-4}$alkylOH.

Clause 44. The compound according to any one of clauses 1 to 33 wherein $R_5$ is $C_{1-6}$haloalkyl.

Clause 45. The compound according to clause 44 wherein $R_5$ is $C_{1-4}$haloalkyl.

Clause 46. The compound according to any one of clauses 1 to 21 wherein $R_4$ and $R_5$ together with the carbon atom to which they are attached form a $C_{3-6}$cycloalkyl such as cyclopropyl.

Clause 47. The compound according to any one of clauses 1 to 21 wherein $R_4$ and $R_5$ together with the carbon atom to which they are attached form a $C_{3-6}$heterocycloalkyl such as tetrahydropyranyl or piperidinyl.

Clause 48. The compound according to any one of clauses 1 to 47 wherein at least one, such as one, nitrogen atom of a $C_{3-6}$heterocycloalkyl ring is substituted, for example by $C_{1-4}$alkyl, C(O)H, C(O)$C_{1-4}$alkyl, C(O)O$C_{1-4}$alkyl, C(O)O$C_{1-4}$alkylaryl such as C(O)OBz, C(O)NH$C_{1-4}$ alkyl, C(O)NH$C_{1-4}$alkylaryl such as C(O)NHBz, an Fmoc group, C(O)$C_{1-4}$haloalkyl, C(O)O$C_{1-4}$ haloalkyl or C(O)NH$C_{1-4}$ haloalkyl such as C(O)OtBu.

Clause 49. The compound according to any one of clauses 1 to 47 wherein any nitrogen atom in the $C_{3-6}$heterocycloalkyl ring is not substituted.

Clause 50. The compound according to any one of clauses 1 to 49 wherein at least one, such as one, sulphur atom of a $C_{3-6}$heterocycloalkyl ring is substituted, for example by one oxygen atom to form S=O or by two oxygen atoms to form $S(O)_2$.

Clause 51. The compound according to any one of clauses 1 to 49 wherein any sulphur atom in the $C_{3-6}$heterocycloalkyl ring is not substituted.

Clause 52. The compound according to any one of clauses 1 to 34 wherein $R_4$ and $R_5$ are both H.

Clause 53. The compound according to any one of clauses 1 to 37 wherein $R_4$ and $R_5$ are both methyl.

Clause 54. The compound according to any one of clauses 1 to 37 wherein $R_4$ and $R_5$ are both ethyl.

Clause 55. The compound according to any one of clauses 1 to 34 wherein $R_4$ is ethyl and $R_5$ is H.

Clause 56. The compound according to clause 55 wherein $R_4$ and $R_5$ are arranged in an S configuration.

Clause 57. The compound according to any one of clauses 1 to 56 wherein $R_6$ is H.

Clause 58. The compound according to any one of clauses 1 to 56 wherein $R_6$ is $C_{1-3}$alkyl.

Clause 59. The compound according to clause 58 wherein $R_6$ is methyl.

Clause 60. The compound according to any one of clauses 1 to 59 wherein Ar1 is phenyl.

Clause 61. The compound according to any one of clauses 1 to 59 wherein Ar1 is 2-pyridyl.

Clause 62. The compound according to any one of clauses 1 to 61 wherein Ar2 is 3-pyridyl.

Clause 63. The compound according to any one of clauses 1 to 61 wherein Ar2 is 2,5-pyrazinyl.

Clause 64. The compound according to any one of clauses 1 to 63 wherein $R_{10}$ is H.

Clause 65. The compound according to any one of clauses 1 to 63 wherein $R_{10}$ is halo such as F.

Clause 66. The compound according to any one of clauses 1 to 63 wherein $R_{10}$ is $C_{1-3}$alkyl such as methyl.

Clause 67. The compound according to any one of clauses 1 to 63 wherein $R_{10}$ is $OC_{1-2}$ alkyl such as $OCH_3$.

Clause 68. The compound according to any one of clauses 1 to 63 wherein $R_{10}$ is $C_{1-2}$haloalkyl such as $CF_3$.

Clause 69. The compound according to any one of clauses 1 to 63 wherein $R_{10}$ is $OC_{1-2}$haloalkyl.

Clause 70. The compound according to any one of clauses 1 to 63 wherein $R_{10}$ is CN.

Clause 71. The compound according to any one of clauses 65 to 70 wherein $R_{10}$ ortho to the amide.

Clause 72. The compound according to any one of clauses 1 to 71 wherein $R_{11}$ is H.

Clause 73. The compound according to any one of clauses 1 to 71 wherein $R_{11}$ is F.

Clause 74. The compound according to any one of clauses 1 to 71 wherein $R_{11}$ is $C_1$.

Clause 75. The compound according to any one of clauses 1 to 71 wherein $R_{11}$ is $CH_3$.

Clause 76. The compound according to any one of clauses 1 to 71 wherein $R_{11}$ is ethyl.

Clause 77. The compound according to any one of clauses 1 to 71 wherein $R_{11}$ is $OCH_3$.

Clause 78. The compound according to any one of clauses 1 to 71 wherein $R_{11}$ is $CF_3$.

Clause 79. The compound according to any one of clauses 1 to 71 wherein $R_{11}$ is $OCF_3$.

Clause 80. The compound according to any one of clauses 1 to 71 wherein $R_{11}$ is CN.

Clause 81. The compound according to any one of clauses 1 to 80 wherein $R_{12}$ is H.

Clause 82. The compound according to any one of clauses 1 to 80 wherein $R_{12}$ is halo such as fluoro or chloro.

Clause 83. The compound according to any one of clauses 1 to 80 wherein $R_{12}$ is $C_{1-4}$alkyl such as $CH_3$ or ethyl.

Clause 84. The compound according to any one of clauses 1 to 80 wherein $R_{12}$ is $C_2$-4alkynyl.

Clause 85. The compound according to clause 84 wherein $R_{12}$ is $C_2$alkynyl.

Clause 86. The compound according to any one of clauses 1 to 80 wherein $R_{12}$ is $C(=O)C_{1-2}$ alkyl such as $C(=O)CH_3$.

Clause 87. The compound according to any one of clauses 1 to 80 wherein $R_{12}$ is $C_{0-2}$alkylene$C_{3-5}$cycloalkyl.

Clause 88. The compound according to any one of clauses 1 to 80 wherein $R_{12}$ is $OC_{1-4}$alkyl such as $OCH_3$, OEt or OiPr.

Clause 89. The compound according to any one of clauses 1 to 80 wherein $R_{12}$ is $C_{1-3}$alkyleneO$C_{1-3}$alkyl.

Clause 90. The compound according to any one of clauses 1 to 80 wherein $R_{12}$ is $C_{1-4}$ haloalkyl such as $CF_3$.

Clause 91. The compound according to any one of clauses 1 to 80 wherein $R_{12}$ is $OC_{1-4}$ haloalkyl such as $OCH_2CF_3$.

Clause 92. The compound according to any one of clauses 1 to 80 wherein $R_{12}$ is CN.

Clause 93. The compound according to any one of clauses 1 to 80 wherein $R_{12}$ is $OC_{0-2}$alkylene$C_{3-5}$cycloalkyl.

Clause 94. The compound according to any one of clauses 1 to 80 wherein $R_{12}$ is $OCH_2CH_2N(CH_3)_2$.

Clause 95. The compound according to any one of clauses 1 to 80 wherein $R_{12}$ is OH.

Clause 96. The compound according to any one of clauses 1 to 80 wherein $R_{12}$ is $C_{1-4}$alkylOH.

Clause 97. The compound according to any one of clauses 1 to 80 wherein $R_{12}$ is $NR_{23}R_{24}$.

Clause 98. The compound according to clause 97 wherein $R_{23}$ is H.

Clause 99. The compound according to clause 97 wherein $R_{23}$ is $C_{1-2}$alkyl such as $CH_3$.

Clause 100. The compound according to any one of clauses 97 to 99 wherein $R_{24}$ is H.

Clause 101. The compound according to any one of clauses 97 to 99 wherein $R_{24}$ is $C_{1-2}$alkyl such as $CH_3$.

Clause 102. The compound according to any one of clauses 1 to 80 wherein $R_{12}$ is $SO_2CH_3$.

Clause 103. The compound according to any one of clauses 1 to 80 wherein $R_{12}$ is $C(O)N(CH_3)_2$.

Clause 104. The compound according to any one of clauses 1 to 80 wherein $R_{12}$ is $NHC(O)C_{1-3}$alkyl.

Clause 105. The compound according to any one of clauses 1 to 80 wherein $R_{12}$ is a $C_{3-6}$heterocycloalkyl comprising one nitrogen located at the point of attachment to Ar2.

Clause 106. The compound according to any one of clauses 1 to 80 wherein $R_{12}$ together with a nitrogen atom to which it is attached forms an N-oxide ($N^+$—$O^-$).

Clause 107. The compound according to any one of clauses 82 to 106 wherein $R_{12}$ is attached at the meta position of Ar2.

Clause 108. The compound according to any one of clauses 82 to 106 wherein $R_{12}$ is attached at the ortho position of Ar2.

Clause 109. A compound of the examples R1 to R71.

Clause 110. A compound of the examples R72 to R93.

Clause 111. A compound of INTE1 to INTE20 or INTF1 to INTF53.

Clause 112. A compound of INTE21 to INTE39.

Clause 113. A compound of formula (II):

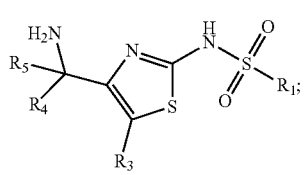

(II)

wherein $R_1$, $R_3$, $R_4$ and $R_5$ are as defined in any one of clauses 1 to 3.

Clause 114. A compound of formula (III):

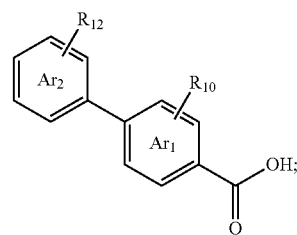

(III)

wherein $R_{10}$, $R_{12}$, $Ar_1$ and $Ar_2$ are as defined in any one of clauses 1 to 3.

Clause 115. A compound of formula (III-A):

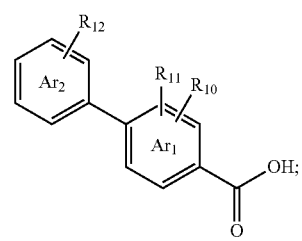

(III-A)

wherein $R_{10}$, $R_{11}$, $R_{12}$, $Ar_1$ and $Ar_2$ are as defined in any one of clauses 1 to 3.

Clause 116. A compound of formula (VIII):

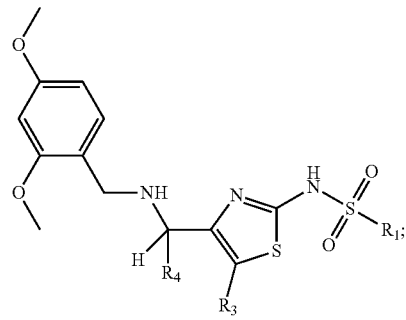

(VIII)

wherein $R_1$, $R_3$ and $R_4$ are as defined in any one of clauses 1 to 3.

Clause 117. A compound according to any one of clauses 113 to 116 which is in the form of a salt.

Clause 118. A compound according to any one of clauses 1 to 110, for use as a medicament.

Clause 119. The compound according to clause 118, for use in the inhibition of CTPS1 in a subject.

Clause 120. The compound according to clause 118, for use in the reduction of T-cell and/or B-cell proliferation in a subject.

Clause 121. The compound according to clause 118, for use in the treatment or prophylaxis of: inflammatory skin diseases such as psoriasis or lichen planus; acute and/or chronic GVHD such as steroid resistant acute GVHD; acute lymphoproliferative syndrome (ALPS); systemic lupus erythematosus, lupus nephritis or cutaneous lupus; or transplantation.

Clause 122. The compound according to clause 118, for use in the treatment or prophylaxis of myasthenia gravis, multiple sclerosis or scleroderma/systemic sclerosis.

Clause 123. A compound according to clause 118, for use in the treatment of cancer.

Clause 124. A method for treating cancer in a subject, by administering to a subject in need thereof a compound according to any one of clauses 1 to 110.

Clause 125. Use of a compound according to any one of clauses 1 to 110, in the manufacture of a medicament for the treatment of cancer in a subject.

Clause 126. The compound according to clause 123, the method according to clause 124 or the use according to clause 125 wherein the cancer is a haematological cancer.

Clause 127. The compound, method or use according to clause 126 wherein the haematological cancer is selected from the group consisting of Acute myeloid leukemia, Angioimmunoblastic T-cell lymphoma, B-cell acute lymphoblastic leukemia, Sweet Syndrome, T-cell Non-Hodgkins lymphoma (including natural killer/T-cell lymphoma, adult T-cell leukaemia/lymphoma, enteropathy type T-cell lymphoma, hepatosplenic T-cell lymphoma and cutaneous T-cell lymphoma), T-cell acute lymphoblastic leukemia, B-cell Non-Hodgkins lymphoma (including Burkitt lymphoma, diffuse large B-cell lymphoma, Follicular lymphoma, Mantle cell lymphoma, Marginal Zone lymphoma), Hairy Cell Leukemia, Hodgkin lymphoma, Lymphoblastic lymphoma, Lymphoplasmacytic lymphoma, Mucosa-associated lymphoid tissue lymphoma, Multiple myeloma, Myelodysplastic syndrome, Plasma cell myeloma, Primary mediastinal large B-cell lymphoma, chronic myeloproliferative disorders (such as chronic myeloid leukemia, primary myelofibrosis, essential thrombocytemia, polycytemia vera) and chronic lymphocytic leukemia.

Clause 128. The compound according to clause 123, the method according to clause 124 or the use according to clause 125 wherein the cancer is a non-haematological cancer such as bladder cancer, breast cancer, melanoma, neuroblastoma, malignant pleural mesothelioma and sarcoma, such as breast cancer and melanoma.

Clause 129. The compound according to clause 118, for use in enhancing recovery from vascular injury or surgery and reducing morbidity and mortality associated with neointima and restenosis in a subject.

Clause 130. A method for enhancing recovery from vascular injury or surgery and reducing morbidity and mortality associated with neointima and restenosis in a subject, by administering to a subject in need thereof a compound according to any one of clauses 1 to 110.

Clause 131. Use of a compound according to any one of clauses 1 to 110, in the manufacture of a medicament for enhancing recovery from vascular injury or surgery and reducing morbidity and mortality associated with neointima and restenosis in a subject.

Clause 132. A method for the inhibition of CTPS1 in a subject, which comprises administering to the subject an effective amount of a compound according to any one of clauses 1 to 110.

Clause 133. Use of a compound according to any one of clauses 1 to 110, in the manufacture of a medicament for the inhibition of CTPS1 in a subject.

Clause 134. A pharmaceutical composition comprising a compound according to any one of clauses 1 to 110.

Clause 135. The compound, method or use according to any one of clauses 118 to 133, for administration to a human subject.

Clause 136. The compound, method, use or composition according to any one of clauses 118 to 135, for administration in conjunction with a further pharmaceutically acceptable active ingredient or ingredients.

Clause 137. The compound, method, use or composition according to any one of clauses 118 to 136, for topical administration to the skin, eye or gut.

Clause 138. The compound according to any one of clauses 1 to 137, which is in natural isotopic form.

REFERENCES

Cheng, D. et al. Discovery of Pyridinyl Acetamide Derivatives as Potent, Selective, and Orally Bioavailable Porcupine Inhibitors. Medicinal Chemistry Letters, 7(7), 676-680; (2016).

Evans, D. R. & Guy, H. I. Mammalian pyrimidine biosynthesis: fresh insights into an ancient pathway. J. Biol. Chem. 279, 33035-33038; (2004).

Fairbanks, L. D., Bofill, M., Ruckemann, K. & Simmonds, H. A. Importance of ribonucleotide availability to proliferating T-lymphocytes from healthy humans. Disproportionate expansion of pyrimidine pools and contrasting effects of de novo synthesis inhibitors. J. Biol. Chem. 270, 29682-29689; (1995).

Higgins, M. J., Graves, P. R. & Graves, L. M. Regulation of human cytidine triphosphate synthetase 1 by glycogen synthase kinase 3. J. Biol. Chem. 282, 29493-29503; (2007).

Kursula, P., Flodin, S., Ehn, M., Hammarström, M., Schüler, H., Nordlund, P. and Stenmarka, P. Structure of the synthetase domain of human CTP synthetase, a target for anticancer therapy. Acta Crystallogr Sect F Struct Biol Cryst Commun. 62 (Pt7): 613-617; (2006).

Lieberman I. Enzymatic amination of uridine triphosphate to cytidine triphosphate. The J. Biol. Chem. 222 (2): 765-75; (1956).

Lübbers, T et al. Aminothiazoles as γ-secretase modulators. Bioorganic & Medicinal Chemistry Letters, 21(21), 6554-6558; 2011

Martin E. et al.; CTP synthase 1 deficiency in humans reveals its central role in lymphocytes proliferation. Nature. June 12; 510(7504):288-92 (2014). Erratum in: Nature. July 17; 511(7509):370 (2014).

McCluskey G D et al., Exploring the Potent Inhibition of CTP Synthase by Gemcitabine-5'-Triphosphate. Chembiochem. 17, 2240-2249 (2016).

Ostrander, D. B., O'Brien, D. J., Gorman, J. A. & Carman, G. M. Effect of CTP synthetase regulation by CTP on phospholipid synthesis in Saccharomyces cerevisiae. J. Biol. Chem. 273, 18992-19001; (1998).

Sakamoto K, Ishibashi Y, Adachi R, et al. Identification of cytidine-5-triphosphate synthasel-selective inhibitory peptide from random peptide library displayed on T7 phage. Peptides, 94:56-63 (2017).

Salu et al. Drug-eluting stents: a new treatment in the prevention of restenosis Part I: experimental studies. Acta Cardiol, 59, 51-61 (2004).

Sousa J. E. et al. Drug-Eluting Stents. Circulation, 107 (2003) 2274 (Part I), 2283 (Part II). van den Berg, A. A. et al. Cytidine triphosphate (CTP) synthetase activity during cell cycle progression in normal and malignant T-lymphocytic cells. Eur. J. Cancer 31, 108-112 (1995).

van Kuilenburg, A. B. P, Meinsma, R., Vreken, P., Waterham, H. R., van Gennip, A. H. Identification of a cDNA encoding an isoform of human CTP synthetase. Biochimica et Biophysica Acta 1492548-552 (2000).

Xing-Li F. et al. Efficient Diphosphane-Based Catalyst for the Palladium-Catalyzed Suzuki Cross-Coupling Reaction of 3-Pyridylboronic Acids. European Journal of Organic Chemistry, (13), 2051-2054; (2009).
The invention claimed is:
1. A compound of the following formula:
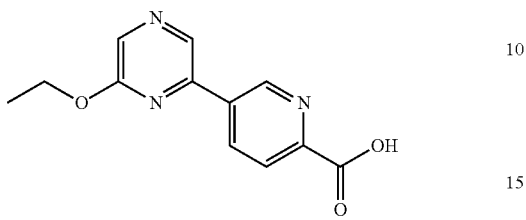
or salts thereof.